(12) United States Patent
Dalli et al.

(10) Patent No.: US 11,555,006 B2
(45) Date of Patent: Jan. 17, 2023

(54) ELUCIDATION OF NOVEL 13-SERIES RESOLVINS THAT INCREASE WITH ATORVASTATIN AND CLEAR INFECTIONS

(71) Applicant: The Brigham and Women's Hospital, Inc., Boston, MA (US)

(72) Inventors: Jesmond Dalli, Brookline, MA (US); Nan Chiang, Somerville, MA (US); Charles N. Serhan, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/579,227

(22) Filed: Sep. 23, 2019

(65) Prior Publication Data

US 2020/0048177 A1 Feb. 13, 2020

Related U.S. Application Data

(63) Continuation of application No. 15/746,214, filed as application No. PCT/US2016/042932 on Jul. 19, 2016, now abandoned.

(60) Provisional application No. 62/194,485, filed on Jul. 20, 2015.

(51) Int. Cl.
 C07C 59/42 (2006.01)
 A61K 31/202 (2006.01)
 A61P 31/04 (2006.01)
 A61K 31/40 (2006.01)

(52) U.S. Cl.
 CPC ............ *C07C 59/42* (2013.01); *A61K 31/202* (2013.01); *A61K 31/40* (2013.01); *A61P 31/04* (2018.01); *Y02A 50/30* (2018.01)

(58) Field of Classification Search
 CPC .......... C07C 59/42; C07C 69/86; C07C 57/03
 See application file for complete search history.

(56) References Cited

U.S. PATENT DOCUMENTS

| 8,853,437 | B2 | 10/2014 | Arita | |
| 2009/0291916 | A1* | 11/2009 | Petasis | C07C 67/303 514/63 |
| 2011/0178047 | A1 | 7/2011 | Arterburn | |
| 2011/0190389 | A1* | 8/2011 | Arterburn | A61K 31/202 514/475 |
| 2012/0059061 | A1 | 3/2012 | Arita | |
| 2015/0119591 | A1 | 4/2015 | Fortin | |

FOREIGN PATENT DOCUMENTS

| JP | 2012-503001 | 2/2012 |
| WO | 2010033509 A2 | 3/2010 |
| WO | 2014193652 | 12/2014 |

OTHER PUBLICATIONS

Atar, S., et al. Atorvastatin-induced cardioprotection is mediated by increasing inducible nitric oxide synthase and consequent S-nitrosylation of cyclooxygenase-2. American journal of physiology. Heart and circulatory physiology 290, H1960-1968 (2006).
Berge S. M., et al., "Pharmaceutical Salts," J. Pharm. Sci., 1977; 66:1 19.
Borregaard, N. Neutrophils, from marrow to microbes. Immunity 33, 657-670 (2010).
Cederberg, H., et al. Increased risk of diabetes with statin treatment is associated with impaired insulin sensitivity and insulin secretion: a 6 year follow-up study of the METSIM cohort. Diabetologia 58, 1109-1117 (2015).
Chiang, N., et al. Infection regulates pro-resolving mediators that lower antibiotic requirements. Nature 484, 524-528 (2012).
Claria, J. & Serhan, C. N. Aspirin triggers previously undescribed bioactive eicosanoids by human endothelial cell-leukocyte interactions. Proceedings of the National Academy of Sciences of the United States of America 92, 9475-9479 (1995).
Colas, R. A., Shinohara, M., Dalli, J., Chiang, N. & Serhan, C. N. Identification and signature profiles for pro-resolving and inflammatory lipid mediators in human tissue. American journal of physiology. Cell physiology (2014).
Corej, E. J. Bakshi, R. K. & Shibata, S. Highly Enantioselective Borane Reduction of Ketones Catalyzed by Chiral Oxazaborolidines. Mechanism and Synthetic Implications. J Am Chem Soc 109, 5551-5553 (1987).
Dalli, J., Colas, R. A. & Serhan, C. N. Novel n-3 immunoresolvents: structures and actions. Sci Rep 3, 1940 (2013).
European Patent Office, Extended European Search Report for application 16828406.5, dated Marc. 1, 2019, 7 pages.

(Continued)

*Primary Examiner* — Pancham Bakshi
(74) *Attorney, Agent, or Firm* — Haukaas Fortius PLLC; Colin L. Fairman

(57) ABSTRACT

New host-protective molecules containing conjugated triene and diene double bonds with each carrying a 13-carbon position alcohol and were derived from n-3 docosapentaenoic acid (DPA, C22:5) were produced in neutrophil-endothelial co-cultures, and they are present in human and mouse tissues after sterile inflammation or infection. These compounds, termed 13-series resolvins (RvT), demonstrated potent protective actions increasing mice survival during *Escherichia coli* infections. Their biosynthesis during neutrophil-endothelial cell interactions was initiated by endothelial cyclooxygenase-2 (COX-2) and increased by atorvastatin via S-nitrosylation of COX-2. Atorvastatin and RvT were additive in *E. coli* infections in mice where they accelerated resolution of inflammation and increased survival >60%. Results documented novel host protective molecules in bacterial infections, namely RvT, derived from n-3 DPA via transcellular biosynthesis and increased by atorvastatin. RvT also regulated human and mouse phagocyte responses stimulating bacterial phagocytosis and regulating inflammasome components to regulate key innate protective responses in the resolution of infectious-inflammation.

3 Claims, 28 Drawing Sheets

(56) References Cited

OTHER PUBLICATIONS

Fullerton, J. N., O'Brien, A. J. & Gilroy, D. W. Lipid mediators in immune dysfunction after severe inflammation. Trends in immunology 35, 12-21 (2014).
Gangemi, S., et al. Physical exercise increases urinary excretion of lipoxin A4 and related compounds. Journal of applied physiology 94, 2237-2240 (2003).
Gryglewski, R. J. & Mackiewicz, Z. Vane's blood-bathed organ technique adapted to examine the endothelial effects of cardiovascular drugs in vivo. Pharmacological reports: PR 62, 462-467 (2010).
Hemler, M. E. & Lands, W. E. Protection of cyclooxygenase activity during heme-induced destabilization. Archives of biochemistry and biophysics 201, 586-593 (1980).
Henriksbo, B. D., et al. Fluvastatin causes NLRP3 inflammasome-mediated adipose insulin resistance. Diabetes (2014).
Http://www.rxlist.com/lipitor-drug/side-effects-interactions.htm.
Ji, Y., Akerboom, T. P., Sies, H. & Thomas, J. A. S-nitrosylation and S-glutathiolation of protein sulfhydryls by S-nitroso glutathione. Archives of biochemistry and biophysics 362, 67-78 (1999).
Kandasamy, K., et al. Atorvastatin prevents vascular hyporeactivity to norepinephrine in sepsis: role of nitric oxide and alpha(1)-adrenoceptor mRNA expression. Shock 36, 76-82 (2011).
Lemaitre, R. N., et al. Genetic loci associated with plasma phospholipid n-3 fatty acids: a meta-analysis of genome-wide association studies from the CHARGE Consortium. PLoS genetics 7, e1002193 (2011).
Lins, R. L., et al. Pharmacokinetics of atorvastatin and its metabolites after single and multiple dosing in hypercholesterolaemic hemodialysis patients. Nephrology, dialysis, transplantation: official publication of the European Dialysis and Transplant Association—European Renal Association 18, 967-976 (2003).
Magill, S. S., et al. Multistate point-prevalence survey of health care-associated infections. The New England journal of medicine 370, 1198-1208 (2014).
Markworth, J. F., et al. Human inflammatory and resolving lipid mediator responses to resistance exercise and ibuprofen treatment. American journal of physiology. Regulatory, integrative and comparative physiology 305, R1281-1296 (2013).
Morikawa, S., et al. The effect of statins on mRNA levels of genes related to inflammation, coagulation, and vascular constriction in HUVEC. Human umbilical vein endothelial cells. Journal of atherosclerosis and thrombosis 9, 178-183 (2002).
Oh, S. F., Pillai, P. S., Recchiuti, A., Yang, R. & Serhan, C. N. Pro-resolving actions and stereoselective biosynthesis of 18S E-series resolvins in human leukocytes and murine inflammation. The Journal of clinical investigation 121, 569-581 (2011).
Sadik, C. D., Kim, N. D. & Luster, A. D. Neutrophils cascading their way to inflammation. Trends in immunology 32, 452-460 (2011).
Samuelsson, B. Role of basic science in the development of new medicines: examples from the eicosanoid field. The Journal of biological chemistry 287, 10070-10080 (2012).
Serhan, C. N. Pro-resolving lipid mediators are leads for resolution physiology. Nature 510, 92-101 (2014).
Serhan, C. N., et al. Resolvins: a family of bioactive products of omega-3 fatty acid transformation circuits initiated by aspirin treatment that counter proinflammation signals. The Journal of experimental medicine 196, 1025-1037 (2002).
Tabas, I. & Glass, C. K. Anti-inflammatory therapy in chronic disease: challenges and opportunities. Science 339, 166-172 (2013).
Von Moltke, J., et al. Rapid induction of inflammatory lipid mediators by the inflammasome in vivo. Nature 490, 107-111 (2012).
Ward, P. A. New approaches to the study of sepsis. EMBO molecular medicine 4, 1234-1243 (2012).
Ye, Y., et al. Activation of peroxisome proliferator-activated receptor-gamma (PPAR-gamma) by atorvastatin is mediated by 15-deoxy-delta-12, 14-PGJ2. Prostaglandins & other lipid mediators 84, 43-53 (2007).
Ye, Y., et al. Phosphorylation of 5-lipoxygenase at ser523 by protein kinase A determines whether pioglitazone and atorvastatin induce proinflammatory leukotriene B4 or anti-inflammatory 15-epi-lipoxin a4 production. Journal of immunology 181, 3515-3523 (2008).
Dalli et al., Elucidation of Novel 13-Series Resolvins that Increase with Atorvastatin and Clear Infections., Nature Medicine, (Aug. 3, 2015).
Primdahl et al., Synthesis of 13(R)-Hydroxy-7Z,10Z,13R,14E,16Z,19Z, Docosapentaenoic Acid (13R-HDPA) and its Biosynthetic Conversion to the 13-Series Resolvins., Journal of Natural Products, 79(10), 2693-2702, (Oct. 5, 2016).
Spite et al., Novel Lipid Mediators Promote Resolution of Acute Inflammation: Impact of Aspirin and Statins, Circulation Research, 107(10), 1170-1184 (2010).
Office Action from Corresponding Japanese Patent Application No. 2018-502764, Dated Jun. 16, 2020, 10 Pages.

\* cited by examiner

ELUCIDATION OF NOVEL 13-SERIES RESOLVINS THAT INCREASE WITH ATORVASTATIN AND CLEAR INFECTIONS

CROSS-REFERENCE TO RELATED APPLICATIONS

This application is a continuation of U.S. patent application Ser. No. 15/746,214, filed Jan. 19, 2018; which represents the national stage entry of PCT International Application PCT/US2016/042932, filed Jul. 19, 2016, which claims priority U.S. Provisional Patent Application 62/194,485, filed Jul. 20, 2015. The contents of these applications is hereby incorporated by reference as if set forth in their entirety herein.

STATEMENT REGARDING FEDERALLY SPONSORED RESEARCH

This invention was made with government support under grant P01GM095467 awarded by The National Institutes of Health. The government has certain rights in the invention.

FIELD OF THE INVENTION

The present invention provides new bioactive compounds derived from n-3 docosapentaenoic acid (DPA, C22:5) that demonstrate potent protective action against infection and active in resolving inflammation.

BACKGROUND OF THE INVENTION

Infections are a leading cause of mortality worldwide, with bacterial infections, including those caused by *Escherichia coli*, posing an urgent health concern[1,2]. The prevalent approach for treating bacterial infections is administration of antibiotics, but with the rise in antibiotic-resistant bacteria, there is a pressing need for new treatment strategies[1,2]. In response to infection, the host mounts inflammatory responses that when self-resolving are protective[3-5]. We previously characterized potent endogenous anti-inflammatory and pro-resolving mediators namely resolvins, protectins and maresins known as specialized pro-resolving mediators (SPM)[4]. These are biosynthesized from n-3 essential fatty acids eicosapentaenoic acid (EPA) and docosahexaenoic acid (DHA)[4]. Docosapentaenoic acid (n-3, DPA), the intermediate in DHA biosynthesis from EPA, accumulates in individuals[6] with single nucleotide polymorphisms in the gene encoding for fatty acid elongase-2 and is also the precursor for three new SPM families[7].

During the resolution phase of a self-resolving acute inflammation, SPM are produced locally and exert protective actions on leukocytes stimulating clearance of apoptotic cells, debris and bacteria as well as promote tissue regeneration[4,8]. Signals produced in the early phase of infectious-inflammation can determine the amplitude and duration of the inflammatory response[9]. Hence, novel mediators that may be produced during early phases of self-resolving infections to fine-tune the initial response and promote resolution are of general interest.

Therefore, a need exists to identify mediators produced during the early phases of self-resolving infections, to characterize such mediators in both their structural formulae and their bioactive effects.

SUMMARY OF THE INVENTION

Endogenous mechanisms leading to host protection and resolution of infections without immunosuppression are of wide interest[1,2]. Here we elucidated the structures of four new host-protective molecules produced in neutrophil-endothelial co-cultures, and present in human and mouse tissues after sterile inflammation or infection. These bioactive molecules contained conjugated triene and diene double bonds with each carrying a 13-carbon position alcohol and were derived from n-3 docosapentaenoic acid (DPA, C22:5). These compounds, termed 13-series resolvins (RvT), demonstrated potent protective actions increasing mice survival during *Escherichia coli* infections. RvT also regulated human and mouse phagocyte responses stimulating bacterial phagocytosis and regulating inflammasome components. Their biosynthesis during neutrophil-endothelial cell interactions was initiated by endothelial cyclooxygenase-2 (COX-2) and increased by atorvastatin via S-nitrosylation of COX-2. The actions of atorvastatin and RvT were additive in *E. coli* infections in mice where they accelerated resolution of inflammation and increased survival >60%. These results document novel host protective molecules in bacterial infections, namely 13-series resolvins, derived from n-3 DPA via transcellular biosynthesis and increased by atorvastatin. These novel molecules regulate key innate protective responses in the resolution of infectious-inflammation.

The present invention surprisingly provides novel compounds, compositions and methods of use of novel dihydroxy and trihydroxy analogues of docosapentaenoic is (DPA) all having a hydroxyl group at one or more of the 7 and 13 positions of the 22 carbon chain. These materials are biogenically derived and/or isolated from inflammatory exudates.

In one embodiment, the invention pertains to a new and useful DPA analogue such as a compound comprising the formula (I):

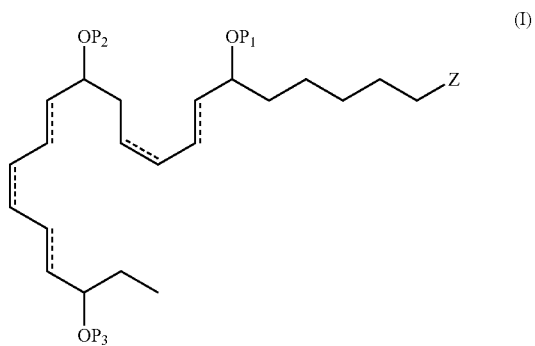

wherein each of $P_1$, $P_2$ and $P_3$ individually is a protecting group or a hydrogen atom;

wherein ===== is a double bond;

wherein each double bond ===== is independently in either the Z or the E configuration;

wherein the carbons at 7, 13 and 20 are independently in the R or S configuration;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each $R^c$, is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^b$ is independently selected from =O, $OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ or —$[NR^aC(NR^a)]_nNR^cR^c$;

each n, independently is an integer from 0 to 3; and
each $R^d$, independently is a protecting group or $R^a$;

or a pharmaceutically acceptable salt thereof, in various aspects, when Z is —$C(O)OR^d$, then $R^d$ for Z is not a hydrogen when $P_1$, $P_2$ and $P_3$ are all hydrogen atoms. In one aspect, $P_1$, $P_2$ and $P_3$ are all hydrogen atoms. In another aspect, the double bond at the 8 position is E. In still another aspect, the double bond at the 10 position is Z. In yet another aspect, the double bond at the 8 position is E and the double bond position at the 10 position is Z.

In one embodiment, one or more of $P_1$, $P_2$ and $P_3$ are hydrogen atoms and the double bond at the 8 position is E.

In another embodiment, one or more of $P_1$, $P_2$ and $P_3$ are hydrogen atoms and the double bond at the 10 position is Z.

In still another embodiment, one or more of $P_1$, $P_2$ and $P_3$ are hydrogen atoms, the double bond at the 8 position is E and the double bond at the 10 position is Z.

In still yet another embodiment, all $P_1$, $P_2$ and $P_3$ are hydrogen atoms, the double bond at the 8 position is E and the double bond at the 10 position is Z.

A particular isomer of interest of the DPA analogue (I) is (Ia) comprising the formula:

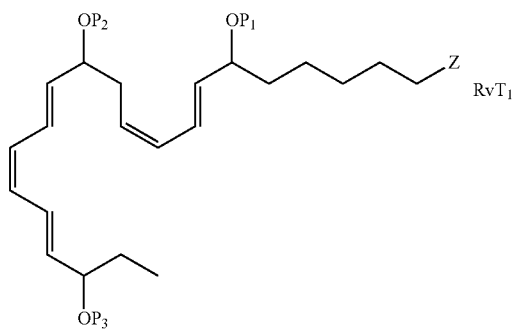

(Ia)

wherein $P_1$, $P_2$, $P_3$, Z, $R^a$, $R^b$, $R^c$, $R^d$ and n are as previously defined and C7, C13 and C20 are independently in the R or S configuration.

In another aspect, the present invention provides new and useful DPA analogues such as purified compounds comprising the formulae (I) or (Ia):

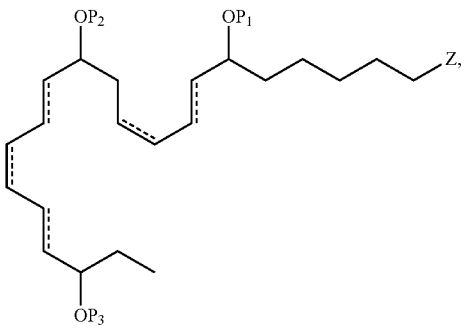

(I)

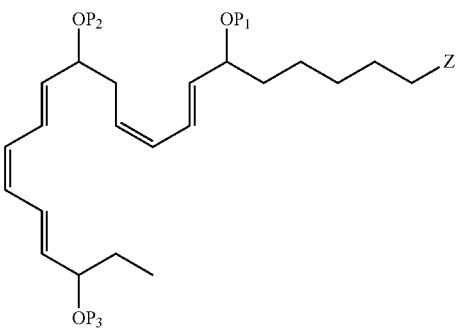

(Ia)

wherein $P_1$, $P_2$, and $P_3$, ======, Z, $R^a$, $R^b$, $R^c$, $R^d$ and n are as previously defined and wherein the carbons at position 7, 13 and 20 are independently in either the R or S configuration. In one aspect, $P_1$, $P_2$ and $P_3$ are all hydrogen atoms. In one aspect, Z is —$C(O)OR^d$ and $R^d$ of Z is a hydrogen atom. In another embodiment, $P_1$, $P_2$ and $P_3$ are all hydrogen atoms, Z is —$C(O)OR^d$ and $R^d$ of Z is a hydrogen atom.

In one aspect, the double bond at the 8 position is E. In still another aspect, the double bond at the 10 position is Z. In yet another aspect, the double bond at the 8 position is E and the double bond position at the 10 position is Z.

In one embodiment, one or more of $P_1$, $P_2$ and $P_3$ are hydrogen atoms and the double bond at the 8 position is E.

In another embodiment, one or more of $P_1$, $P_2$ and $P_3$ are hydrogen atoms and the double bond at the 10 position is Z.

In still another embodiment, one or more of $P_1$, $P_2$ and $P_3$ are hydrogen atoms, the double bond at the 8 position is E and the double bond at the 10 position is Z.

In still yet another embodiment, each $P_1$, $P_2$ and $P_3$ is a hydrogen atom, the double bond at the 8 position is E and the double bond at the 10 position is Z.

In all of the above embodiments, in a particular aspect, Z is —$C(O)OR^d$ and $R^d$ of Z is a hydrogen atom. In other embodiments when compounds I and Ia are purified, then $P_1$, $P_2$ and $P_3$ are hydrogen atoms. In one aspect, Z is —$C(O)OR^d$ and $R^d$ of Z is a hydrogen atom. In another embodiment, $P_1$, $P_2$ and $P_3$ are hydrogen atoms, Z is —$C(O)OR^d$ and $R^d$ of Z is a hydrogen atom.

It should be understood that compounds (I) and (Ia) include all pharmaceutically acceptable salts, esters thereof, the purified/isolated forms, as well as compounds wherein one or both of the possible hydroxyl groups are converted into a protecting group as described herein.

In another aspect, the invention pertains to a new and useful DPA analogue such as a compound comprising the formula (II):

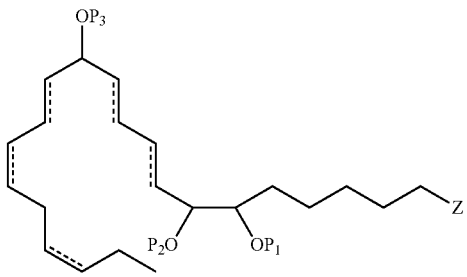

wherein $P_1$, $P_2$, $P_3$, ˉˉˉˉˉ , Z, $R^a$, $R^b$, $R^c$, $R^d$ and n are as previously defined and wherein the carbons at the 7, 8 and 13 position are independently in either the R or S configuration, or a pharmaceutically acceptable salt thereof. In some aspects, when Z is —C(O)OR$^d$, then $R^d$ for Z is not a hydrogen when $P_1$, $P_2$ and $P_3$ are all hydrogen atoms In one embodiment, $P_1$, $P_2$ and $P_3$ are all hydrogen atoms.

In one aspect, the double bond at the 11 position is E. In another aspect, the double bond at the 16 position is Z. In yet another aspect, the double bond at the 11 position is E and the double bond at the 16 position is Z.

In one embodiment, one or more of $P_1$, $P_2$ and $P_3$ are hydrogen atoms and the double bond at the 11 position is E.

In another embodiment, one or more of $P_1$, $P_2$ and $P_3$ are hydrogen atoms and the double bond at the 16 position is Z.

In still another embodiment, one or more of $P_1$, $P_2$ and $P_3$ are hydrogen atoms, the double bond at the 11 position is E and the double bond at the 16 position is Z.

In still yet another embodiment, each $P_1$, $P_2$ and $P_3$ is a hydrogen atom, the double bond at the 14 position is E and the double bond at the 16 position is Z.

A particular isomer of interest of the DPA analogue (II) is (IIa) comprising the formula.

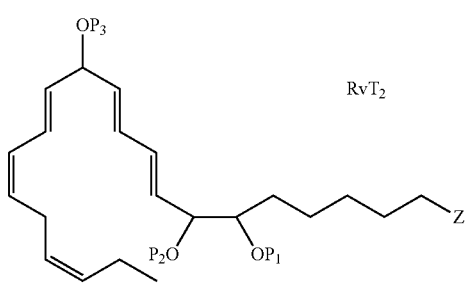

wherein $P_1$, $P_2$, $P_3$, Z, $R^a$, $R^b$, $R^c$, $R^d$ and n are as previously defined and carbons 7, 8 and 13 are independently in either the R or S configuration.

In another aspect, the present invention provides new and useful DPA analogues such as purified compounds comprising the formulae (II) or (IIa):

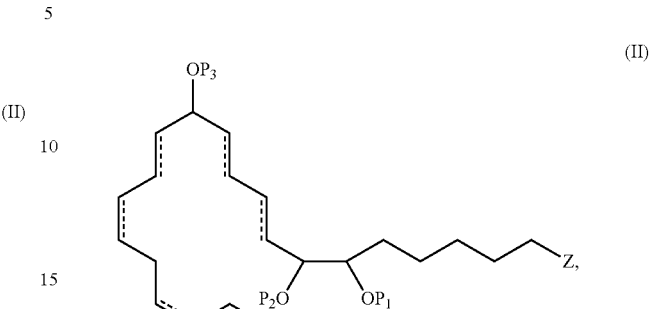

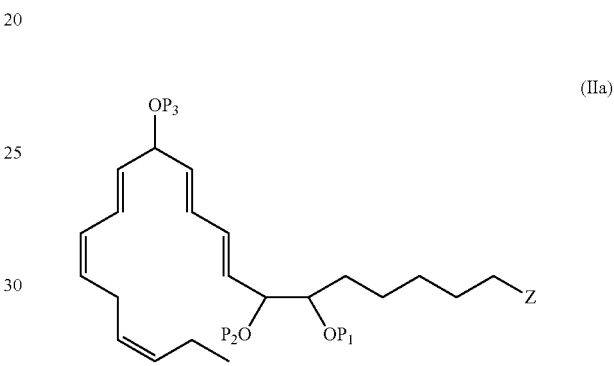

wherein $P_1$, $P_2$, $P_3$, ˉˉˉˉˉ , Z, $R^a$, $R^b$, $R^c$, $R^d$ and n are as previously defined. In one aspect, $P_1$, $P_2$ and $P_3$ are all hydrogen atoms. In one aspect, Z is —C(O)OR$^d$ and $R^d$ of Z is a hydrogen atom. In another embodiment, $P_1$, $P_2$ and $P_3$ are all hydrogen atoms, Z is —C(O)OR$^d$ and $R^d$ of Z is a hydrogen atom.

In one embodiment, one or more of $P_1$, $P_2$, and $P_3$ are hydrogen atoms and the double bond at the 11 position is E.

In another embodiment, one or more of $P_1$, $P_2$ and $P_3$ are hydrogen atoms and the double bond at the 16 position is Z.

In still another embodiment, one or more of $P_1$, $P_2$ and $P_3$ are hydrogen atoms, the double bond at the 11 position is E and the double bond at the 16 position is Z.

In still yet another embodiment, each of $P_1$, $P_2$ and $P_3$ are hydrogen atoms, the double bond at the 11 position is E and the double bond at the 16 position is Z.

In all of the above embodiments, in a particular aspect, Z is —C(O)OR$^d$ and $R^d$ of Z is a hydrogen atom.

In other embodiments when compounds II and IIa are purified, then $P_1$, $P_2$ and/or $P_3$ are both hydrogen atoms. In one aspect, Z is —C(O)OR$^d$ and $R^d$ of Z is a hydrogen atom. In another embodiment, $P_1$, $P_2$ and/or $P_3$ are hydrogen atoms, Z is —C(O)OR$^d$ and $R^d$ of Z is a hydrogen atom.

It should be understood that compounds (II) and (IIa) include all pharmaceutically acceptable salts, esters thereof, the purified/isolated forms, as well as compounds wherein one or both of the possible hydroxyl groups are converted into a protecting group as described herein.

In another aspect, the present invention provides new and useful DPA analogues such as a compound comprising formula (III):

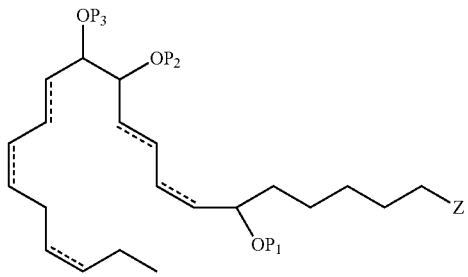

(III)

wherein $P_1$, $P_2$, $P_3$, ------, Z, $R^a$, $R^b$, $R^c$, $R^d$ and n are as previously defined and the carbons at positions 7, 12 and 13 are independently in either the R or S configuration, or a pharmaceutically acceptable salt thereof. In various aspects, when Z is —C(O)OR$^d$, then $R^d$ for Z is not a hydrogen when $P_1$, $P_2$ and $P_3$ are all hydrogen atoms.

In one embodiment, $P_1$, $P_2$, and $P_3$ are all hydrogen atoms.

In one aspect, the double bond at the 16 position is Z. In another aspect, the double bond at the 19 position is Z. In still another aspect, the double bond at the 16 position is Z and the double bond at the 19 position is Z.

In one embodiment, one or more of $P_1$, $P_2$, and $P_3$ are hydrogen atoms and the double bond at the 16 position is Z.

In another embodiment, one or more of $P_1$, $P_2$, and $P_3$ are hydrogen atoms and the double bond at the 19 position is Z.

In still another embodiment, one or more of $P_1$, $P_2$, and $P_3$ are hydrogen atoms, the double bond at the 16 position is Z and the double bond at the 19 position is Z.

In yet another embodiment, both $P_1$, $P_2$, and $P_3$ are hydrogen atoms, the double bond at the 16 position is Z and the double bond at the 19 position is Z.

A particular isomer of interest of the DPA analogue (III) is (IIIa) comprising the formula:

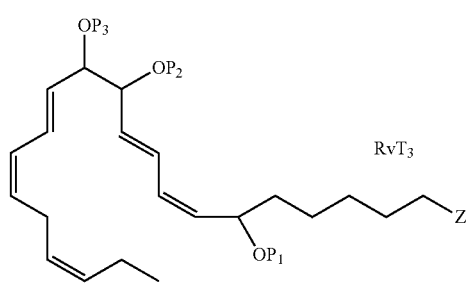

(IIIa)

wherein $P_1$, $P_2$, $P_3$, Z, $R^a$, $R^b$, $R^c$, $R^d$ and n are as previously defined and the carbons at positions 7, 12 and 13 are independently in either the R or S configuration.

In another aspect, the present invention provides new and useful DPA analogues such as purified compounds comprising the formulae (III) or (IIIa):

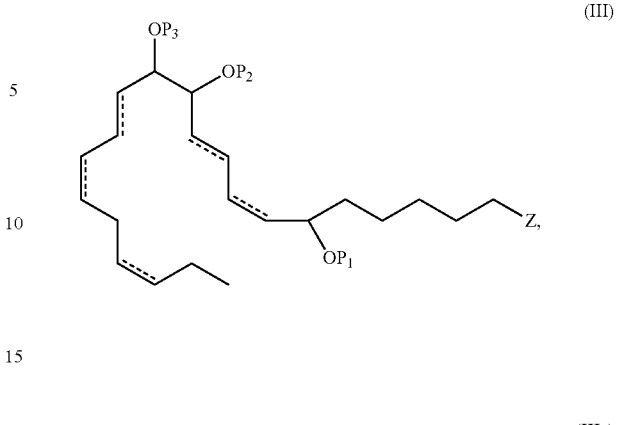

(III)

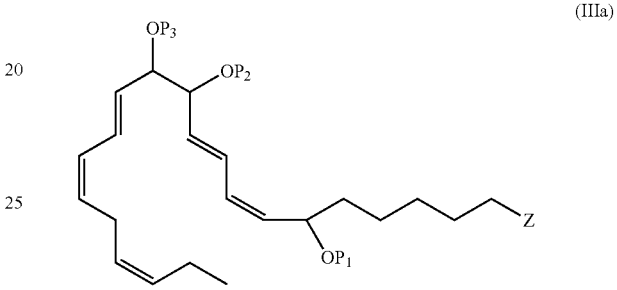

(IIIa)

wherein $P_1$, $P_2$, $P_3$, ------, Z, $R^a$, $R^b$, $R^c$, $R^d$ and n are as previously defined and the carbons at positions 7, 12 and 13 are independently in either the R or S configuration. In one aspect, $P_1$, $P_2$, and $P_3$ are all hydrogen atoms. In one aspect, Z is —C(O)OR$^d$ and $R^d$ of Z is a hydrogen atom. In another embodiment, $P_1$, $P_2$, and $P_3$ are all hydrogen atoms, Z is —C(O)OR$^d$ and $R^d$ of Z is a hydrogen atom.

In one aspect, the double bond at the 16 position is Z. In another aspect, the double bond at the 19 position is Z. In still another aspect, the double bond at the 16 position is Z and the double bond at the 19 position is Z.

In one embodiment, one or more of $P_1$, $P_2$, and $P_3$ are hydrogen atoms and the double bond at the 16 position is Z.

In another embodiment, one or more of $P_1$, $P_2$, and $P_3$ are hydrogen atoms and the double bond at the 19 position is Z.

In still another embodiment, one or more of $P_1$, $P_2$, and $P_3$ are hydrogen atoms, the double bond at the 16 position is Z and the double bond at the 19 position is Z.

In yet another embodiment, $P_1$, $P_2$, and $P_3$ are hydrogen atoms, the double bond at the 16 position is Z and the double bond at the 19 position is Z.

In all of the above embodiments, in a particular aspect, Z is —C(O)OR$^d$ and $R^d$ of Z is a hydrogen atom.

In other embodiments when compounds III and IIIa are purified, then $P_1$, $P_2$ and/or $P_3$ are hydrogen atoms. In one aspect, Z is —C(O)OR$^d$ and $R^d$ of Z is a hydrogen atom. In another embodiment, $P_1$, $P_2$ and $P_3$ are hydrogen atoms, Z is —C(O)OR$^d$ and $R^d$ of Z is a hydrogen atom.

It should be understood that compounds (III) and (IIIa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (IV):

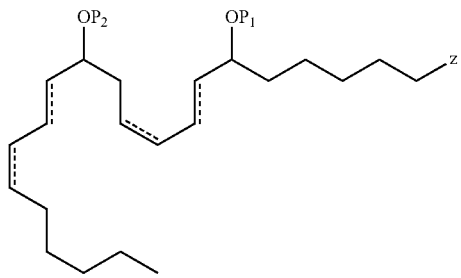

(IV)

wherein $P_1$, $P_2$, ======, Z, $R^a$, $R^b$, $R^c$, $R^d$ and n are as previously defined and C7 and C13 are independently either R or S, or a pharmaceutically acceptable salt thereof. In some aspects when Z is —C(O)OR$^d$, then $R^d$ for Z is not a hydrogen when $P_1$ and $P_2$ are both hydrogen atoms.

In one embodiment, $P_1$ and $P_2$ are both hydrogen atoms.

In one aspect, the double bond at the 16 position is Z. In another aspect, the double bond at the 19 position is Z. In still another aspect, the double bond at the 16 position is Z and the double bond at the 19 position is Z.

In one embodiment, one or more of $P_1$ and $P_2$ are hydrogen atoms and the double bond at the 16 position is Z.

In another embodiment, one or more of $P_1$ and $P_2$ are hydrogen atoms and the double bond at the 19 position is Z.

In still another embodiment, one or more of $P_1$ and $P_2$ are hydrogen atoms, the double bond at the 16 position is Z and the double bond at the 19 position is Z.

In yet another embodiment, both $P_1$ and $P_2$ are hydrogen atoms, the double bond at the 16 position is Z and the double bon at the 19 position is Z.

A particular isomer of interest of the DPA analogue (IV) is (IVa) comprising the formula:

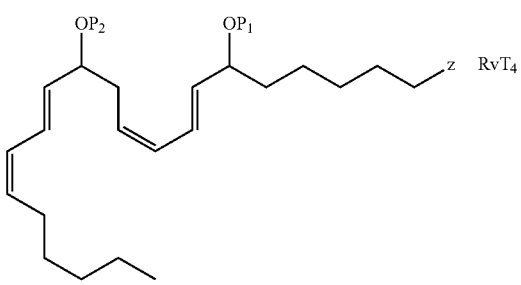

(IVa)

wherein $P_1$, $P_2$, Z, $R^a$, $R^b$, $R^c$, $R^d$, and n and are as previously defined and C7 and C13 are independently either R or S.

In another aspect, the present invention provides new and useful DPA analogues such as purified compounds comprising the formulae (IV) or (IVa):

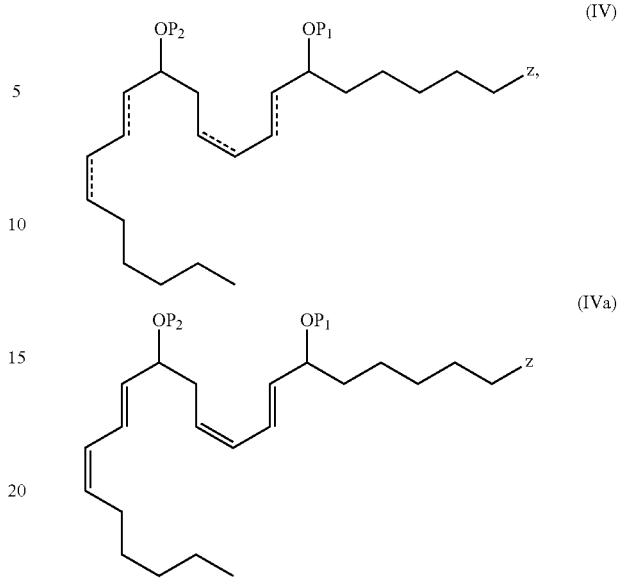

wherein $P_1$, $P_2$, ======, Z, $R^a$, $R^b$, $R^c$, $R^d$ and n are as previously defined and the carbon at positions 7 and 13 are independently in either the R or S configuration. In one aspect, $P_1$ and $P_2$ are both hydrogen atoms. In one aspect, Z is —C(O)OR$^d$ and $R^d$ of Z is a hydrogen atom. In another embodiment, $P_1$ and $P_2$ are both hydrogen atoms, Z is —C(O)OR$^d$ and $R^d$ of Z is a hydrogen atom.

In one aspect, the double bond at the 8 position is Z. In another aspect, the double bond at the 16 position is Z. In yet another aspect, the double bond at the 19 position is Z. In still other aspects, the double bond at the 14 position is E, the double bond at the 10 position is Z.

In one embodiment, one or more of $P_1$ and $P_2$ are hydrogen atoms and the double bond at the 8 position is E.

In another embodiment, one or more of $P_1$ and $P_2$ are hydrogen atoms and the double bond at the 16 position is Z.

In still another embodiment, one or more of $P_1$ and $P_2$ are hydrogen atoms and the double bond at the 19 position is Z.

In still yet another embodiment, one or more of $P_1$ and $P_2$ are hydrogen atoms and at least two of the double bonds at the 10, 16 and/or 19 positions are Z.

In yet another embodiment, both $P_1$ and $P_2$ are hydrogen atoms and at least two of the double bonds at the 10, 16 and/or 19 positions are Z.

In still another embodiment, both $P_1$ and $P_2$ are hydrogen atoms and two of the double bonds at the 7, 16 and 19 positions are Z.

In all of the above embodiments, in a particular aspect, Z is —C(O)OR$^d$ and $R^d$ of Z is a hydrogen atom.

In other embodiments when compounds IV and IV are purified, then $P_1$ and $P_2$ are both hydrogen atoms. In one aspect, Z is —C(O)OR$^d$ and $R^d$ of Z is a hydrogen atom. In another embodiment, $P_1$ and $P_2$ are both hydrogen atoms, Z is —C(O)OR$^d$ and $R^d$ of Z is a hydrogen atom.

It should be understood that compounds (IV) and (IVa) include all pharmaceutically acceptable salts, esters thereof, the purified/isolated forms, as well as compounds wherein one or both of the possible hydroxyl groups are converted into a protecting group as described herein.

It should also be understood that any of the compounds described herein can be used for treatment or prevention of any of the ailments, diseases, or afflictions noted throughout the specification.

In another aspect, the present invention provides pharmaceutical compositions comprising one or more compounds of the invention, with or without other active pharmaceutical ingredients, in admixture with a pharmaceutically acceptable vehicle. Such a preparation can be administered according to the methods of the current invention.

In yet another aspect, the present invention is drawn to methods for treating or preventing inflammation or inflammatory disease in a mammal. The method involves administering a prophylactically or therapeutically effective amount of at least one compound of the invention, or a pharmaceutical composition thereof. For example, the compounds of the invention can be used to treat or prevent inflammation, cancer, neurodegeneration, memory loss, wrinkles, psoriasis, dandruff or dermatitis by administering to an individual in need thereof, an effective amount of any of the compounds described herein.

In yet another aspect, the present invention is drawn to methods for treating or preventing bacterial infection or disease in a mammal. The method involves administering a prophylactically or therapeutically effective amount of at least one compound of the invention, or a pharmaceutical composition thereof.

In yet another aspect, the present invention is drawn to methods to decrease the amount of statin required for health. The method involves administering a prophylactically or therapeutically effective amount of at least one compound of the invention or to pharmaceutical composition thereof. In other embodiments, the invention provides a method to augment statin therapy comprising providing to a subject in need thereof a therapeutically effective amount of a compound according to claims 1-5 in addition to a statin compound to a subject in need of statin therapy.

In yet other embodiments, the invention provides method to treat or prevent a bacterial infections comprising administering to a subject in need thereof a compound or composition comprising any of RvT 1, 1a, 2, 2a, III, IIIa, IV or IVa as disclosed above.

In yet another embodiment, the invention provides a method to increase the survival rate of a subject suffering from bacterial infections comprising administering to the subject a therapeutic amount of a compound comprising any of RvT 1, 1a, 2, 2a, III, IIIa, IV or IVa as disclosed above.

In still another embodiment, the invention provides a method to promote phagocytosis, efferocytosis, wound healing or tissue regeneration in a subject in need thereof comprising, administering to a patient in need thereof a therapeutically effective amount of a compound comprising any of RvT 1, 1a, 2, 2a, III IIIa, IV or IVa as disclosed above.

In still a further embodiment, the invention provides a method of stimulating reactive oxygen species production in leukocytes comprising administering to a subject in need of leukocyte stimulation a therapeutic amount of a compound according to any of claims 1-5.

Additionally, the compounds of the invention can be used to augment neural development, fetal development, homeostasis, tissue remodeling, or wound repair by administering to an individual in need thereof, an effective amount of any of the compounds described herein.

Additional features and advantages of the invention will become more apparent from the following detailed description and claims.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

Figure 1:
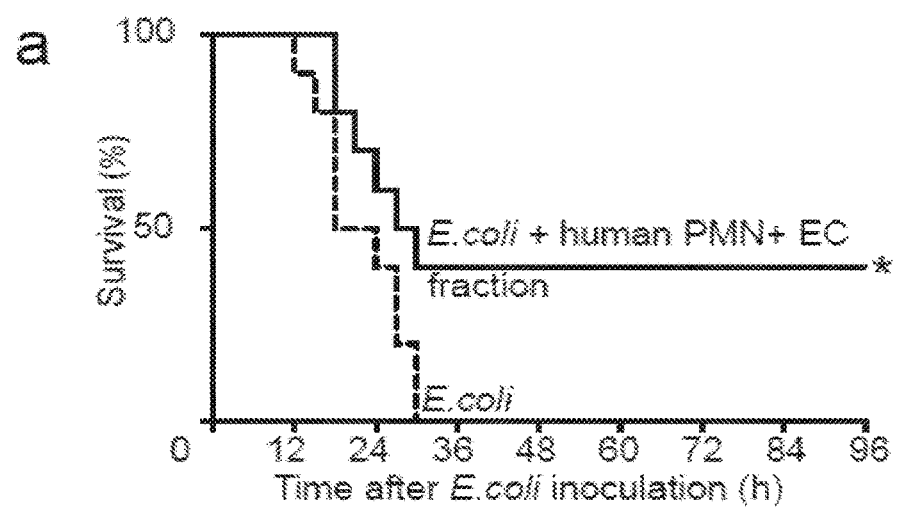
FIG. 1: Novel 13-series resolvins (RvT) from neutrophil-endothelial cell interactions are elevated in self-resolving inflammation. (a) Fractions were extracted from human neutrophil (PMN)-endothelial cell (EC) co-incubations (see methods), administered to mice via i.v. injection 5 min prior to $E.\ coli$ ($2.5 \times 10^7$ CFU/mouse) inoculation and survival assessed. n=10 mice/group from three independent experiments. *p<0.05 vs. $E.\ coli$ group. (b) Proposed structures from the novel 13-series resolvins (RvT) identified in human PMN-EC co-incubations. (c) Blood was collected from healthy volunteers pre- and post-exercise (see methods) and amounts of RvT assessed using LC-MS-MS. n=4 healthy volunteers from four independent experiments. *p<0.05 vs. pre-exercise values. (d) Plasma was obtained from the NIST repository (SRM 1950, d=3), collected from healthy volunteers (n=4) or patients diagnosed with sepsis (n=9), and RvT assessed using LC-MS-MS. Results are expressed as mean±s.e.m, from two independent experiments. *p<0.05, **p<0.01 vs. SRM 1950, #p<0.05, ##p<0.01 vs. healthy volunteers. (e) Mice were inoculated with $E.\ coli$ ($1 \times 10^5$ CFU/mouse), blood was collected at the indicated intervals and RvT amounts assessed using LC-MS-MS. (f) Mice were inoculated with $1 \times 10^5$ CFU/mouse $E.\ coli$ (self-resolving) or $1 \times 10^7$ CFU/mouse $E.\ coli$ (delayed-resolving), blood was collected after 4 h and RvT assessed using LC-MS-MS. Results for e, f are expressed as mean±s.e.m. n=4 mice per group from two independent experiments. *p<0.05 vs 0 h blood levels (e) or vs. mice receiving a self-resolving inoculum (f).
Figure 1:
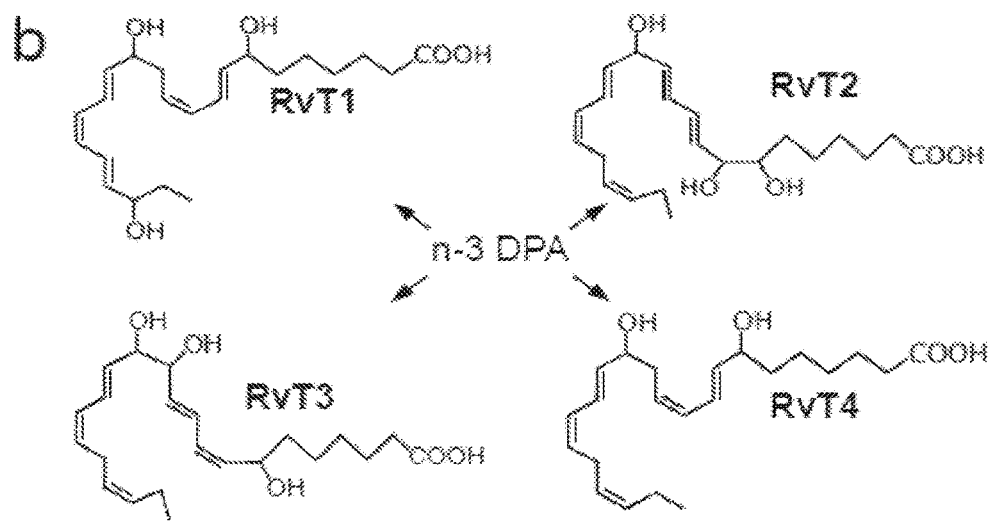
Figure 1:
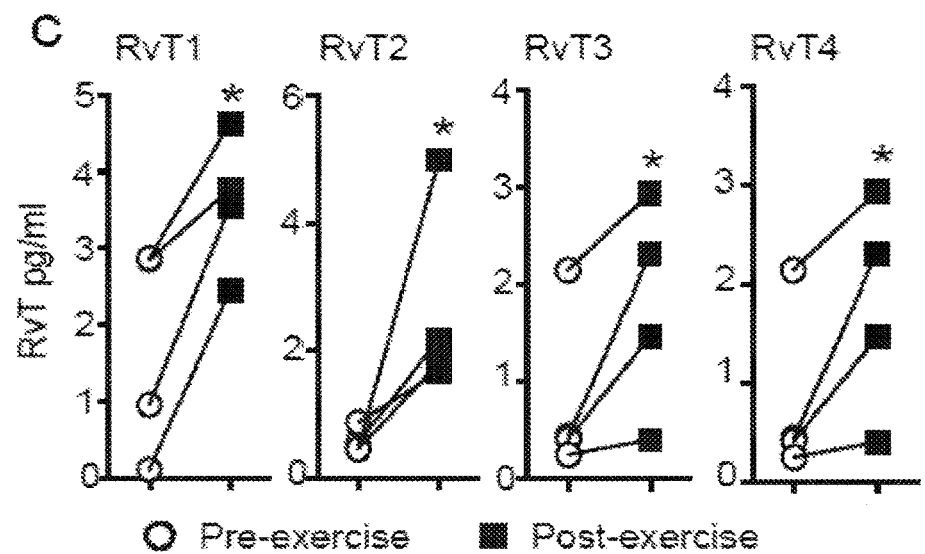
Figure 1:
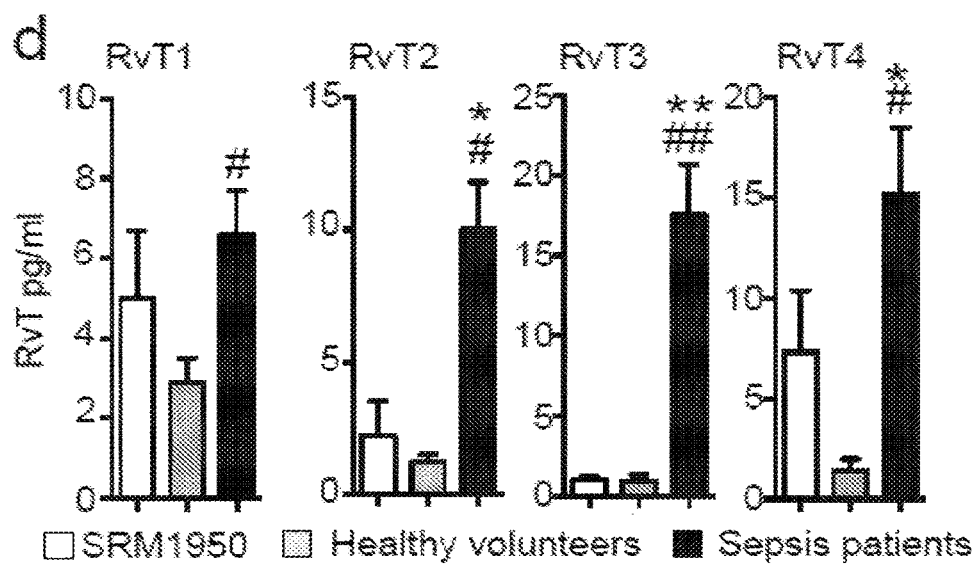
Figure 1:
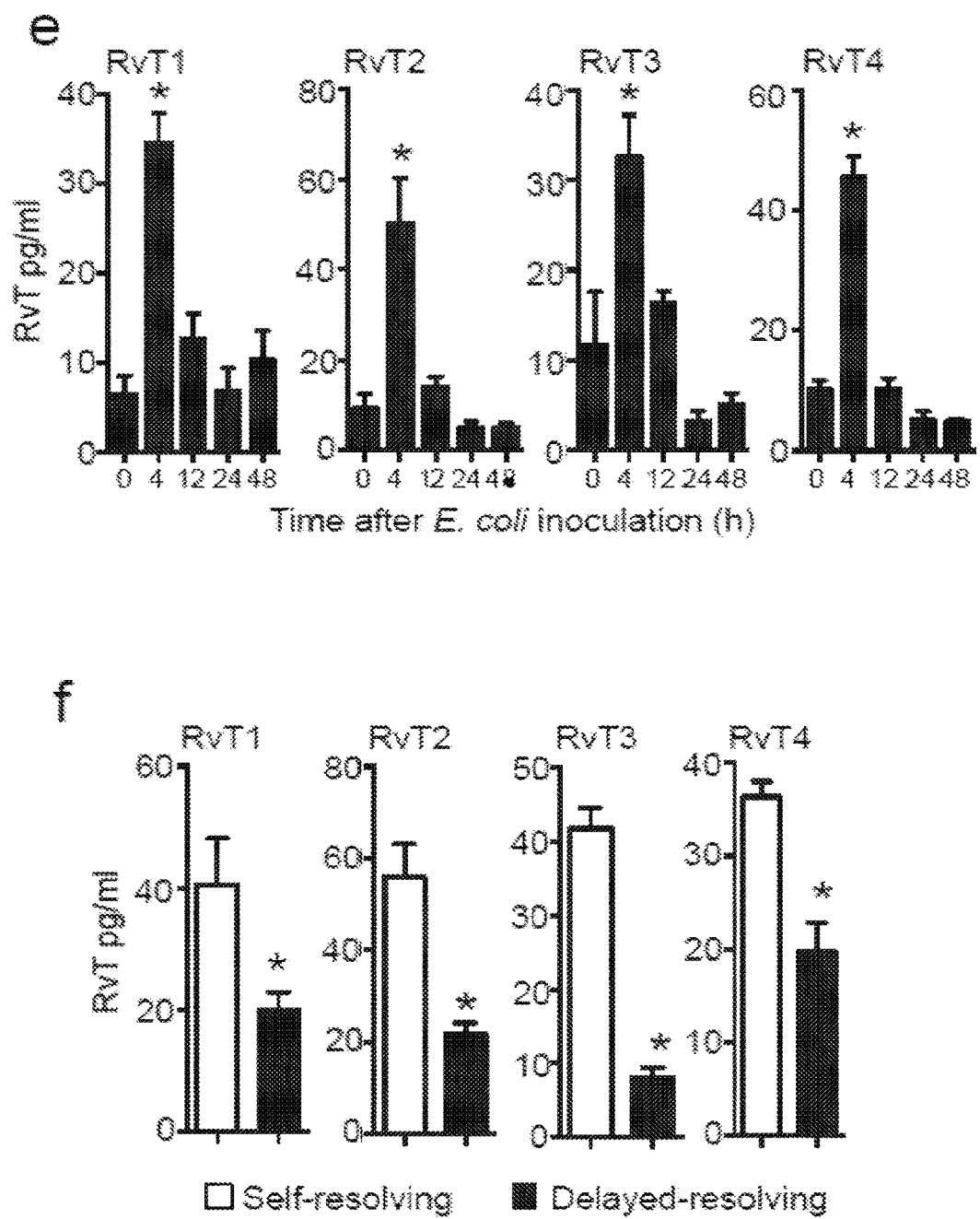

Endogenous mechanisms leading to host protection and resolution of infections without immunosuppression are of wide interest[1,2]. Here the inventors elucidated the structures of four new host-protective molecules produced in neutrophil-endothelial co-cultures, and present in human and mouse tissues after sterile inflammation or infection. These bioactive molecules contained conjugated triene and diene double bonds with each carrying a 13-carbon position alcohol and were derived from n-3 acid (DPA, C22:5). These compounds, termed 13-series resolvins (RvT), demonstrated potent protective actions increasing mice survival during *Escherichia coli* infections. RvT also regulated human and mouse phagocyte responses stimulating bacterial phagocytosis and regulating inflammasome components. Their biosynthesis during neutrophil-endothelial cell interactions was initiated by endothelial cyclooxygenase-2 (COX-2) and increased by atorvastatin via S-nitrosylation of COX-2. The actions of atorvastatin and RvT were additive in *E. coli* infections in mice where they accelerated resolution of inflammation and increased survival >60%. These results document novel host protective molecules in bacterial infections, namely 13-series resolvins, derived from n-3 DPA via transcellular biosynthesis and increased by atorvastatin. These novel molecules regulate key innate protective responses in the resolution of infectious-inflammation.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by", "contain(s)" and "having" and variants thereof can be used interchangeably and are intended to be open-ended transitional phrases, terms, or words that do not preclude the possibility of additional acts or structures.

"Compounds of the invention" refers to the di-hydroxy and/or trihydroxy, DPA analogues and compounds encompassed by generic formulae disclosed herein and includes any specific compounds within those formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention also include isotopically labeled compounds where one or more atoms have an atomic mass different from the atomic mass conventionally found in nature.

The compounds depicted throughout the specification contain ethylenically unsaturated sites. Where carbon carbon double bonds exist, the configurational chemistry can be either cis (Z) or trans (E) and the depictions throughout the specification are not meant to be limiting. The depictions are, in general, presented based upon the configurational chemistry of DPA compounds, and although not to be limited by theory, are believed to possess similar configuration chemistry. The use of ≈≈≈≈≈ reflects this throughout the specification and claims so that both cis (Z) and trans (E) isomers are contemplated. In certain embodiments the configuration of the ethylenic bond is known and is particularly described.

In one aspect of the invention, the compound(s) of the invention are substantially purified and/or isolated by techniques known in the art. The purity of the purified compounds is generally at least about 90%, preferably at least about 95%, and most preferably at least about 99% by weight.

Thus, the term "purified" as used herein does not require absolute purity; rather, it is intended as a relative term. For example, a purified DPA analogue can be one in which the subject DPA analogue is at a higher concentration than the analogue would be in its natural environment within an organism. For example, a DPA analogue of the invention can be considered purified if the analogue content in the preparation represents at least 50%, 60%, 70%, 80%, 85%, 90%, 92%, 95%, 98%, or 99% of the total analogue content of the preparation.

"Biological activity" and its contextual equivalents "activity" and "bioactivity" means that a compound elicits a statistically valid effect in any one biological test assays. Preferably, the threshold for defining an "active" compound will be reproducible and statistically valid effects of at least 25% deviation from untreated control at concentrations at or lower than 1 µM.

"Biological test assay" means a specific experimental procedure. Non-limiting examples of biological test assays include: 1) ligand binding, either direct or indirect, to a purified target, subcellular fraction, intact cell, or cell or tissue extract; 2) metabolic protection with enhanced half-life when exposed to a purified target, subcellular fraction, intact cell, cell or tissue extract, or administered to intact organism by any route; 3) prevention, reversal, or amelioration of cell- and tissue-based functional responses recognized by skilled artisans to represent surrogates for anti-inflammatory action (e.g., altered cytokine production and release); and 4) prevention, reversal, or amelioration of symptoms and/or disease processes in animal models of inflammation and inflammatory disease.

"Detectable label" means any chemical or biological modality which can be used to track, trace, localize, quantify, immobilize, purify, or identify compounds through appropriate means of detection known in the art. Non-limiting examples of detectable labels include fluorescence, phosphorescence, luminescence, radioactive or biospecific affinity capture labels.

"Electronegative group" is a chemical group that tends to acquire rather than lose electrons in its chemical interactions. Examples of electronegative groups include, but are not limited to, —$NO_2$, ammonium salts, sulfonyl groups, carbonyl groups, halogens, esters, carboxylic acids, nitrites, etc.

"In Situ" refers to and includes the terms "in vivo," "ex vivo" and "in vitro" as these terms are commonly recognized and understood by the skilled artisan. Moreover, the phrase "in situ" is employed herein in its broadest connotative and denotative context to identify an entity, cell, or tissue as found or in place, without regard to its source or origin, its condition or status or its duration or longevity at that location or position.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) salts formed when an basic proton is present in the parent compound such as acid addition salts, formed with inorganic acids such as hydrochloric acid, hydrobromic acid, sulfuric acid, nitric add, phosphoric acid, and the like; or those formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, naphthaienesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton is present in the parent compound and either is replaced by a metal ion, e.g., an alkali metal ion, an alkaline earth ion, or an aluminum ion; or coordinates with an organic base such as ethanolamine, diethanolamine, triethanolamine, N-methylglucamine, triethylamine, propylamino, diazabicycloundecane and the like.

"Pharmaceutically acceptable vehicle" refers to a diluent, adjuvant, excipient or carrier with which a compound of the invention is administered.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

"Prodrug" refers to a derivative of a drug molecule that requires a transformation within the body to release the active drug. Prodrugs are frequently (though not necessarily) pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, imine, phosphoryl, phosphoryl or sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which contain different functional groups other than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2.sup.nd ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl. ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated (e.g., methyl and ethyl esters, acetate or propionate groups or glycol esters) or alkylated such as benzyl, and trityl ethers as well as alkyl ethers, tetrahydropyranyl ethers, trialkylsilyl ethers (e.g., TMS or TIPPS groups) and allyl ethers.

"Subject" means living organisms susceptible to conditions or diseases caused or contributed to by infection, inflammation, inflammatory responses, vasoconstriction and myeloid suppression. Examples of subjects include humans, dogs cats, cows, goats and mice. The term subject is further intended to include transgenic species such as, for example, transgenic mice.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but- 1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl-, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In a preferred embodiment, the alkdiyl group is (C1-C6) alkdiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkdiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkdiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl-, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkane groups, e.g., methano, ethano, propano, butano, and the like.

"Heteroalkyl," Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where the specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrene and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrene, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrene, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripyridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipyridyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyis, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula "—OR", "alkylamine" refers to a group of the formula "—NHR" and "dialkylamine" refers to a group of the formula "—NRR", where each "R" is independently an alkyl. As another example, "haloalkoxy" or "haloalkyloxy" refers to a group of the formula "—OR", where "R" is a haloalkyl.

The present invention is also drawn to methods for treating inflammasome activation, diabetes, nasopharyngitis, arthralgia, diarrhea, pain in the extremities, bacterial infection, dyspepsia, nausea, musculoskeletal pain, muscle spasms, myalgia, insomnia, pharyngolaryngia pain, inflammation, arterial inflammation, arthritis, psoriasis, urticara, vasculitis, asthma, ocular inflammation, pulmonary inflammation, pulmonary fibrosis, seborrheic dermatitis, pustular dermatosis, cardiovascular diseases, recruitment of neutrophils, leukocytes and/or cytokines, allergy, Alzheimer's disease, asthma, atherosclerosis, cancer, cardiovascular diseases, diabetes, genitourinary disorders, hypertension, infectious diseases, neuromuscular disorders, renal disorders, oral infections or periodontal disease The pharmaceutical compositions of the invention include a "therapeutically effective amount" or a "prophylactically effective amount" of one or more of the DPA analogs of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the DPA analog may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the DPA analog and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a DPA analog of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one DPA analog, in combination with a pharmaceutically acceptable carrier.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1 19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patients system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The invention features an article of manufacture that contains packaging material and DPA analog formulation contained within the packaging material. This formulation contains an at least one DPA analog and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable DPA analogs are described herein.

The present invention surprisingly provides novel compounds, compositions and methods of use pertaining to, dihydroxy and/or trihydroxy analogues of new and useful DPA analogue such as a compound comprising the formula (I):

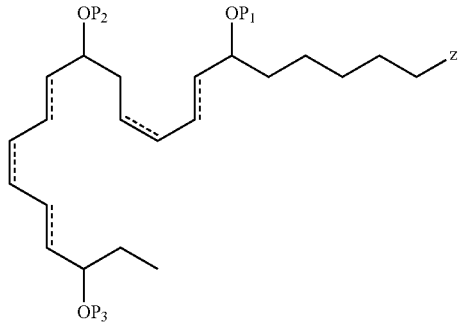

wherein each of $P_1$, $P_2$ and $P_3$ individually is a protecting group or a hydrogen atom;

wherein ═════ is a double bond;

wherein each double bond ═════ is independently in either the Z or the E configuration;

wherein the carbons at 7, 13 and 20 are independently in the R or S configuration;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from ═O, —OR$^d$, (C1-C3) haloalkyloxy, —OCF$_3$, ═S, —SR$^d$, ═NR$^d$, ═NOR$^d$, —NR$^c$R$^c$, halogen, —CF$_3$, —CN, —NC, —OCN, —SCN, —NO, —NO$_2$, ═N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$R$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof, in various aspects, when Z is —C(O)OR$^d$, then R$^d$ for Z is not a hydrogen when $P_1$, $P_2$ and $P_3$ are all hydrogen atoms. In other aspects, $P_1$, $P_2$ and $P_3$ are all hydrogen atoms. In other aspects, one or more of $P_1$, $P_2$ and $P_3$ are hydrogen atoms and Z is —C(O)OR$^d$, and R$^d$ for Z is a hydrogen.

A particular isomer of interest of the DPA analogue (I) is (Ia) comprising the formula:

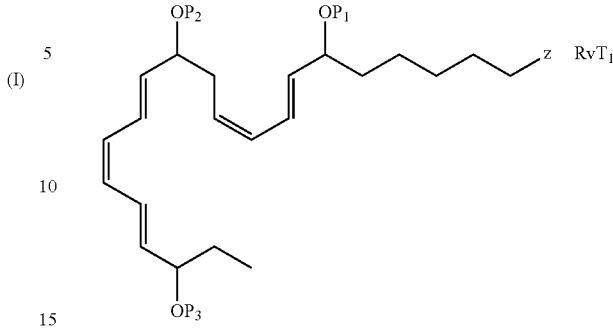

wherein $P_1$, $P_2$, $P_3$, Z, R$^a$, R$^b$, R$^c$, R$^d$ and n are as previously defined and C7, C13 and C20 are independently in the R or S configuration.

In another aspect, the present invention provides new and useful DPA analogues such as purified compounds comprising the formulae (I) or (Ia):

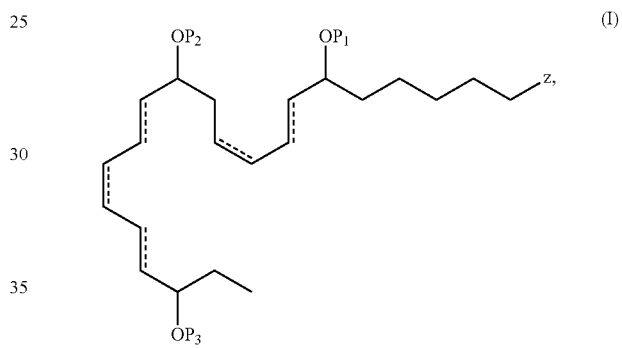

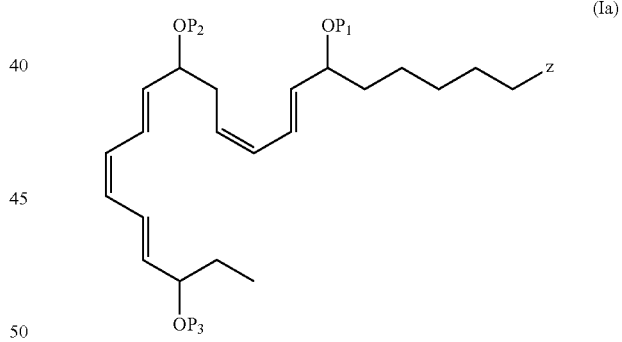

wherein $P_1$, $P_2$, and $P_3$, ═════ , Z, R$^a$, R$^b$, R$^c$, R$^d$ and n are as previously defined and wherein the carbons at position 7, 13 and 20 are independently in either the R or S configuration. In one aspect, $P_1$, $P_2$ and $P_3$ are all hydrogen atoms. In one aspect, Z is —C(O)OR$^d$ and R$^d$ of Z is a hydrogen atom. In another embodiment, $P_1$, $P_2$ and $P_3$ are all hydrogen atoms, Z is —C(O)OR$^d$ and R$^d$ of Z is a hydrogen atom.

In all of the above embodiments, in a particular aspect, Z is —C(O)OR$^d$ and R$^d$ of Z is a hydrogen atom. In other embodiments when compounds I and Ia are purified, then $P_1$, $P_2$ and $P_3$ are hydrogen atoms. In one aspect, Z is —C(O)OR$^d$ and R$^d$ of Z is a hydrogen atom. In another embodiment, $P_1$, $P_2$ and $P_3$ are hydrogen atoms, Z is —C(O)OR$^d$ and R$^d$ of Z is a hydrogen atom.

It should be understood that compounds (I) and (Ia) include all pharmaceutically acceptable salts, esters thereof, the purified/isolated forms, as well as compounds wherein one or both of the possible hydroxyl groups are converted into a protecting group as described herein.

In another aspect, the invention pertains to a new and useful DPA analogue such as a compound comprising the formula (II):

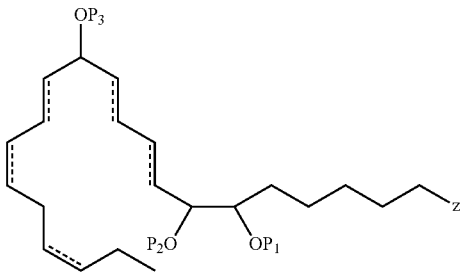

(II)

wherein $P_1$, $P_2$, $P_3$, ======, Z, $R^a$, $R^b$, $R^c$, $R^d$ and n are as previously defined and wherein the carbons at the 7, 8 and 13 position are independently in either the R or S configuration, or a pharmaceutically acceptable salt thereof. In some aspects, when Z is —C(O)OR$^d$, then $R^d$ for Z is not a hydrogen when $P_1$, $P_2$ and $P_3$ are all hydrogen atoms. In yet other aspects when Z is —C(O)OR$^d$, then $R^d$ for Z is a hydrogen when $P_1$, $P_2$ and $P_3$ are all hydrogen atoms.

In one embodiment, $P_1$, $P_2$, and $P_3$ are all hydrogen atoms.

A particular isomer of interest of the DPA analogue (II) is (IIa) comprising the formula:

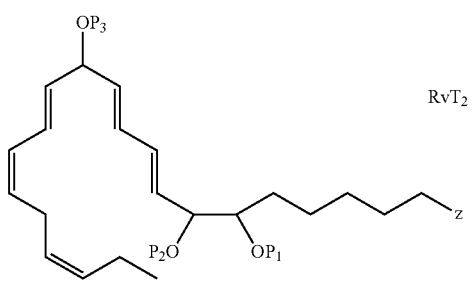

(IIa)

wherein $P_1$, $P_2$, $P_3$, Z, $R^a$, $R^b$, $R^c$, $R^d$ and n are as previously defined and carbons 7, 8 and 13 are independently in either the R or S configuration.

In another aspect, the present invention provides new and useful DPA analogues such as purified compounds comprising the formulae (II) or (IIa):

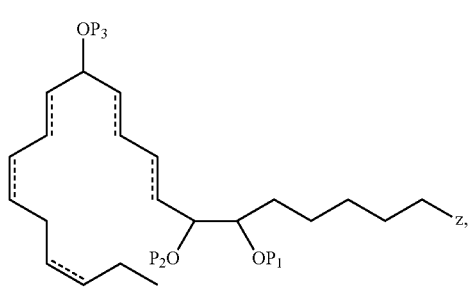

(II)

(IIa)

wherein $P_1$, $P_2$, $P_3$, ======, Z, $R^a$, $R^b$, $R^c$, $R^d$ and n are as previously defined. In one aspect, $P_1$, $P_2$ and $P_3$ are all hydrogen atoms. In one aspect, Z is —C(O)OR$^d$ and $R^d$ of Z is a hydrogen atom. In another embodiment, $P_1$, $P_2$ and $P_3$ are all hydrogen atoms. Z is —C(O)OR$^d$ and $R^d$ of Z is a hydrogen atom.

In all of the above embodiments, in a particular aspect, Z is —C(O)OR$^d$ and $R^d$ of Z is a hydrogen atom.

In other embodiments when compounds II and IIa are purified, then $P_1$, $P_2$ and/or $P_3$ are both hydrogen atoms. In one aspect, Z is —C(O)OR$^d$ and $R^d$ of Z is a hydrogen atom. In another embodiment, $P_1$, $P_2$ and $P_3$ are hydrogen atoms, Z is —C(O)OR$^d$ and $R^d$ of Z is a hydrogen atom.

It should be understood that compounds (II) and (IIa) include all pharmaceutically acceptable salts, esters thereof, the purified/isolated forms, as well as compounds wherein one or both of the possible hydroxyl groups are converted into a protecting group as described herein.

In another aspect, the present invention provides new and useful DPA analogues such as a compound comprising formula (III):

(III)

wherein $P_1$, $P_2$, $P_3$, ======, Z, $R^a$, $R^b$, $R^c$, $R^d$ and n are as previously defined and the carbons at positions 7, 12 and 13 are independently in either the R or S configuration, or a pharmaceutically acceptable salt thereof. In various aspects, when Z is —C(O)OR$^d$, then $R^d$ for Z is not a hydrogen when $P_1$, $P_2$ and $P_3$ are all hydrogen atoms. In yet other aspects, when Z is —C(O)OR$^d$, then $R^d$ for Z is a hydrogen when $P_1$, $P_2$ and $P_3$ are all hydrogen atoms.

In one embodiment, $P_1$, $P_2$, and $P_3$ are all hydrogen atoms.

A particular isomer of interest of the DPA analogue (III) is (IIIa) comprising the formula:

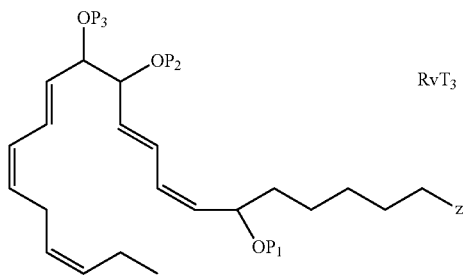

(IIIa)

wherein $P_1$, $P_2$, $P_3$, Z, $R^a$, $R^b$, $R^c$, $R^d$ and n are as previously defined and the carbons at positions 7, 12 and 13 are independently in either the R or S configuration.

In another aspect, the present invention provides new and useful DPA analogues such as purified compounds comprising the formulae (III) or (IIIa):

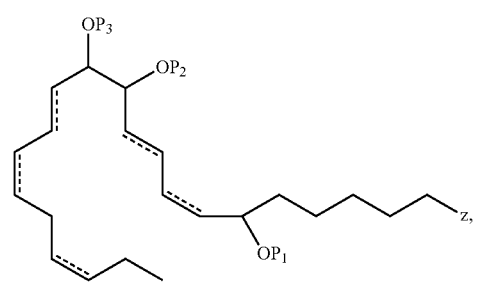

(II)

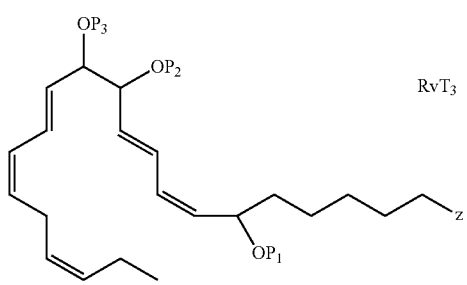

(IIIa)

wherein $P_1$, $P_2$, $P_3$, ------- , Z, $R^a$, $R^b$, $R^c$, $R^d$ and n are as previously defined and the carbons at positions 7, 12 and 13 are independently in either the R or S configuration. In one aspect, $P_1$, $P_2$, and $P_3$ are all hydrogen atoms. In one aspect, Z is —C(O)OR$^d$ and $R^d$ of Z is a hydrogen atom. In another embodiment, $P_1$, $P_2$, and $P_3$ are all hydrogen atoms, Z is —C(O)OR$^d$ and $R^d$ of Z is a hydrogen atom.

In all of the above embodiments, in a particular aspect, Z is —C(O)OR$^d$ and $R^d$ of Z is a hydrogen atom.

In other embodiments when compounds III and IIIa are purified, then $P_1$, $P_2$ and/or $P_3$ are hydrogen atoms. In one aspect, Z is —C(O)OR$^d$ and $R^d$ of Z is a hydrogen atom. In another embodiment, $P_1$, $P_2$ and $P_3$ are hydrogen atoms, Z is —C(O)OR$^d$ and $R^d$ of Z is a hydrogen atom.

It should be understood that compounds (III) and (IIIa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (IV):

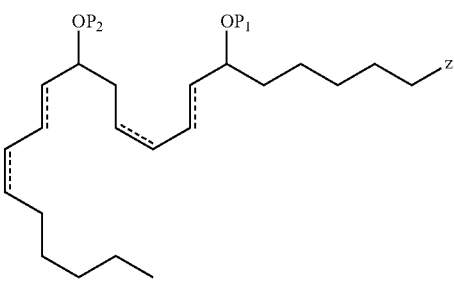

wherein $P_1$, $P_2$, ------- , Z, $R^a$, $R^b$, $R^c$, $R^d$ and n are as previously defined and C7 and C13 are independently either R or S, or a pharmaceutically acceptable salt thereof. In some aspects when Z is —C(O)OR$^d$, then $R^d$ for Z is not a hydrogen when $P_1$ and $P_2$ are both hydrogen atoms. In other aspects when Z is —C(O)OR$^d$, then $R^d$ for Z is a hydrogen when $P_1$ and $P_2$ are both hydrogen atoms.

In one embodiment, $P_1$ and $P_2$ are both hydrogen atoms.

A particular isomer of interest of the DPA analogue (IV) is (IVa) comprising the formula:

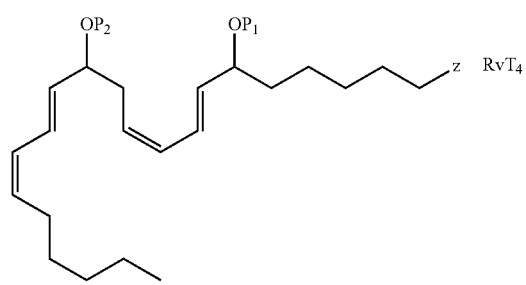

(IVa)

wherein $P_1$, $P_2$, Z, $R^a$, $R^b$, $R^c$, $R^d$, and n and are as previously defined and C7 and C13 are independently either R or S.

In another aspect, the present invention provides new and useful DPA analogues such as purified compounds comprising the formulae (IV) or (IVa):

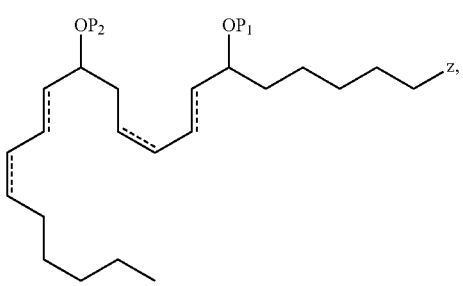

(IV)

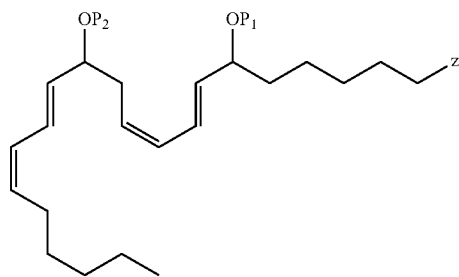

(IVa)

wherein $P_1$, $P_2$, ======, Z, $R^a$, $R^b$, $R^c$, $R^d$ and n are as previously defined and the carbon at positions 7 and 13 are independently in either the R or S configuration. In one aspect, $P_1$ and $P_2$ are both hydrogen atoms. In one aspect, Z is —C(O)OR$^d$ and R$^d$ of Z is a hydrogen atom. In another embodiment, $P_1$ and $P_2$ are both hydrogen atoms, Z is —C(O)OR$^d$ and R$^d$ of Z is a hydrogen atom.

In all of the above embodiments, in a particular aspect, Z is —C(O)OR$^d$ and R$^d$ of Z is a hydrogen atom.

In other embodiments when compounds IV and IV are purified, then $P_1$ and $P_2$ are both hydrogen atoms. In one aspect, Z is —C(O)OR$^d$ and R$^d$ of Z is a hydrogen atom. In another embodiment, $P_1$ and $P_2$ are both hydrogen atoms, Z is —C(O)OR$^d$ and R$^d$ of Z is a hydrogen atom.

It should be understood that compounds (IV) and (IVa) include all pharmaceutically acceptable salts, esters thereof, the purified/isolated forms, as well as compounds wherein one or both of the possible hydroxyl groups are converted into a protecting group as described herein.

Materials and Methods

E. coli Peritonitis

All animal experiments were conducted in accordance with the Harvard Medical Area Standing Committee on Animals (protocol no. 02570). Mice (male FvB, 6-8 weeks old, Charles River, fed lab diet containing essential fatty acids as from supplier) were anesthetized with isoflurane and microbial peritonitis initiated. Briefly, test compounds or vehicle were injected i.p. or i.v. 5 min prior to live E. coli (serotype 06:K2:H1; $1 \times 10^5$ or $1 \times 10^7$ CFU/mouse). At designated time intervals mice were harvested, blood was collected via cardiac puncture in heparin, and peritoneal exudates were collected in 4 ml of PBS. The cellular composition in the exudates was determined using Turks solution and light microscopy, and by flow cytometry. For flow cytometry, exudate cells were incubated with anti-mouse CD16/CD32 (eBiosciences, 20 min, 4° C., in PBS containing 5% fetal calf serum-staining solution), followed by incubation with FITC-conjugated anti-mouse Ly6G antibody (clone: 1A8, eBiosciences), PE-conjugated anti-mouse F4/80 antibody (clone:BM8, eBiosciences) and PerCP-Cy5.5-conjugated anti-mouse CD11b antibody (clone:M1/70, eBiosciences) for 30 min (4° C., in staining solution). To assess bacterial phagocytosis in peritoneal exudate leukocytes, exudate cells were incubated with PerCP-Cy5.5-conjugated anti-mouse CD11b antibody (30 min, 4° C., in staining solution), then fixed and permeabilized using BD Perm/Wash™ Buffer (BD Biosciences) following manufacturer's instructions and incubated with FITC-conjugated anti-E. coli antibody (GenTex, 30 min, 4° C., in BD Perm/Wash™ Buffer). Efferocytosis in infectious exudates was assessed by incubating exudate leukocytes with PE-conjugated anti-mouse F4/80 antibody (30 min, 4° C., in staining solution), then fixed and permeabilized using BD Perm/Wash™ Buffer (BD Biosciences) and incubated with FITC-conjugated anti-mouse Ly6G antibody (30 min, 4° C., in BD Perm/Wash™ Buffer). Body temperatures were assessed using an Infrared thermometer (Fluke). Bacterial counts in peripheral blood and inflammatory exudates were determined by overnight cultures (37° C.) of serially diluted samples on LB agar plates. Caspase 1 levels were assessed by incubation of exudate cells with PerCP-Cy5.5-conjugated anti-mouse CD11b antibody (30 min, 4° C., in staining solution), then fixed and permeabilized using BD Perm/Wash™ Buffer (BD Biosciences), incubated with anti-caspase 1 antibody (Abcam, 30 min, 4° C., in BD Perm/Wash™ Buffer) followed by anti-rabbit Alexa 488 conjugated antibody (Life Technologies, 30 min, 4° C., in BD Perm/Wash™ Buffer). IL-1β levels were determined in cell-free supernatants using an anti-mouse IL-1β ELISA (Abcam) following manufacturer's instructions. Lactate dehydrogenase activity was measured in cell-free supernatants assessing the formation of NADH from NAD+ using a Lactate Dehydrogenase Assay kit (Sigma) following manufacturer's instructions.

In select experiments resolution indices were calculated as in [27]. $\Psi_{max}$, maximal PMN numbers in exudates; $T_{max}$, time point when PMN numbers reach maximum; $R_{50}$, 50% of maximal PMN numbers; $T_{50}$, time point when PMN numbers reduce to 50% of maximum; $R_i$ (resolution interval), $T_{50}$-$T_{max}$, time period when 50% PMN are lost from the exudates. To assess the proresolving actions of the test products, these were administered 12 h after E. coli ($10^5$ CFU) inoculation, and resolution indices were assessed.

For some experiments, mice were administered via i.p. injection RvT1, RvT2, RvT3 and RvT4 (that were isolated as detailed below and combined as a mixture at a ratio of 2:1:1:8 respectively) 2 h after E. coli inoculation. Blood and lungs were harvested 6 h after E. Coli inoculation. Blood was employed to determine peripheral blood eicosanoid levels as detailed below. Lungs were placed in TriReagent (Invitrogen), RNA isolated following manufacturer's instructions and relative mRNA expression for mouse endothelin-1 and plasminogen activator inhibitor-1 determined using Qiagen SYBR® Green ROX qPCR mastermix and QuantiTect® Primer assays following manufacturer's instruction and using mouse Glyceraldehyde 3-phosphate dehydrogenase as housekeeping gene. mRNA expression was determined using an ABI PRISM 7900HT system (Applied Biosystems). In determined experiments, peritoneal exudates were obtained from mice 12 h after E. coli inoculation and bacterial loads along with leukocyte counts determined as detailed above.

For survival studies, mice were administered test compounds or biological isolates from neutrophil-endothelial cell (HUVEC) co-incubations via i.p. injection 5 min prior to inoculation with E. coli ($2.5 \times 10^7$ CFU), and survival was assessed. In designated experiments, RvT1, RvT2, RvT3 and RvT4 were isolated as detailed below, combined as a mixture at a ratio of 2:1:1:8 respectively, and were administered via i.p. injection 2 h after E. coli ($2.5 \times 10^7$ CFU); survival was assessed for the subsequent 94 h. In separate experiments, 0.5 µg (lower dose) or 5 µg (higher dose) of atorvastatin was administered via i.p. with or without RvT1, RvT2, RvT3 and RvT4, which were isolated and quantified as detailed below, combined as a mixture (at a ratio of 2:1:1:8) at the indicated concentrations 3 h after E. coli ($2.5 \times 10^7$ CFU) inoculation, and survival assessed for the next 93 h.

In a separate set of experiments, mice were inoculated with E. coli; after 60 min they were given L-NAME (24 mg/kg) and 5 min later atorvastatin (5 μg) via i.v. injection. Plasma was obtained after 5 h via cardiac puncture and LM levels were investigated by lipid mediator metabololipidomics. For all animal experiments mice were randomized to vehicle or treatment groups without blinding.

Biosynthesis and Lipid Mediator Metabololipidomics

Isolated n-3 DPA (Cayman Chemicals) was incubated with human recombinant COX-2 (Cayman Chemicals; in 0.1 M Tris-HCl, pH 8.0, 20 μM porcine hematin, 0.67 mM phenol) for 30 min at RT. Incubations were stopped with 1 volume of methanol and products extracted using diethyl ether as in [28]. 13-HDPA was isolated using RP-HPLC (1100 Series; Agilent Technologies) and an Agilent C18 Poroshell column (2.7 μm×4.6 mm×150 mm) with a mobile phase consisting of methanol/water (60:40, vol:vol) at 0.5 ml/min that was ramped up to 98:2 (vol:vol) for 20 min. 13-HDPA (10 μM) was incubated with potato 5-LOX (Cayman Chemicals) for 30 min (4° C., 0.1 M phosphate buffer, pH 6.3, 0.03% Tween 20). Incubations were stopped with 1 volume of ice-cold methanol, products were reduced using $NaBH_4$ (Sigma-Aldrich) and extracted as in [28].

Methanol (2 volumes) was added to cell incubations, plasma (mouse and human) and infectious exudates, and samples stored at −20° C. until extraction. All samples for LC-MS-MS-based metabololipidomics were extracted with solid-phase extraction columns as previously reported [29]. Prior to sample extraction, deuterated internal standards ($d_4$-$PGE_2$, $d_5$-$LXA_4$, $d_4$-RvD2, $d_4$-$LTB_4$ and $d_8$-5S-HETE) representing regions of interest in the chromatographic analysis (500 pg each) were added to facilitate quantification. Extracted samples were analyzed by a LC-MS-MS system, Qtrap 6500 (AB Sciex) equipped with a Shimadzu SIL-20AC autoinjector and LC-20AD binary pump (Shimadzu Corp.). An Agilent Eclipse Plus C18 column (100× 4.6 mm×1.8 μm) was used with a gradient of methanol/water/acetic acid of 55:45:0.01 (vol:vol:vol) that was ramped to 85:15:0.01 (vol:vol:vol) over 10 min and then to 98:2:0.01 (vol:vol:vol) for the next 8 min. This was subsequently maintained at 98:2:0.01 (vol:vol:vol) for 2 min. The flow rate was maintained at 0.4 ml/min. To monitor and quantify the levels of lipid mediators, a multiple reaction monitoring (MRM) method was developed with signature ion fragments (m/z) for each molecule monitoring the parent ion (Q1) and a characteristic daughter ion (Q3). Identification was conducted using published criteria where a minimum of 6 diagnostic ions were employed [29]. Calibration curves were determined using a mixture of lipid mediators obtained via total organic synthesis, where these lipid mediators were not available (RvT1, RvT2, RvT3, RvT4 and 13-HDPA); known mediators with similar chromatographic properties (RvD2 for RvT1, RvD1 for RvT2 and RvT3; RvD5 for RvT4; 13-HDHA for 13-HDPA) were used. Linear calibration curve for each compound was obtained with $r^2$ values ranging from 0.98 to 0.99. Detection limit was ~0.1 pg. Quantification was carried out as in [29]. To measure 6-keto-$PGF_{1\alpha}$ levels, samples were extracted as outlined above, suspended in water, and 6-keto-$PGF_{1\alpha}$ levels measured using a 6-keto-$PGF_{1\alpha}$ ELISA (Neogen).

For chiral lipidomic analysis, a Chiralpak AD-RH column (150 mm×2.1 mm×5 μm) was used with isocratic methanol/water/acetic acid 95:5:0.01 (v/v/v) at 0.15 ml/min. To monitor isobaric monohydroxy docosapentaenoic acid levels, a multiple reaction monitoring (MRM) method was developed using signature ion fragments for each molecule as in [30].

In select experiments, RvT1, RvT2, RvT3 and RvT4 were incubated with diazomethane in ether, prepared as in [28] for 30 min at 37° C. and products assessed by LC-MS-MS, operating the mass spectrometer in positive ion mode.

In order to extract products from neutrophil-endothelial cell co-incubations for biological evaluation, 2 volumes of ice-cold methanol were added to stop the incubations and the samples placed at −20° C. for at least 30 min to allow for protein precipitation. Products were then extracted using C18 SPE as detailed above and eluted using methyl formate. The solvent was then evaporated under nitrogen and products suspended in ethanol for biological evaluation.

13R-HDPA and 13S-HDPA were obtained by incubating 13-HDPA with Dess Martin Periodinane (0.03 M in methylene chloride, 30 min, RT); the resulting 13-oxo-DPA was then incubated with either (R)-2-methyl-CBS-oxazaborolidine or (S)-2-methyl-CBS-oxazaborolidine as in [31].

In some experiments, human peripheral neutrophils ($5 \times 10^7$ cells/ml) were incubated with 13R-HDPA (1 μM, 37° C., PBS pH 7.45) and ($1 \times 10^9$ CFU/ml, 2 min, 37° C.). Incubations were stopped with 2 volumes of acidified methanol (apparent pH 3), products extracted and profiled using LM metabololipidomics.

Human neutrophils ($4 \times 10^7$ cells/ml) were incubated with 13R-HDPA (300 nM) in PBS (pH 7.45, 37° C.) in an $^{18}O_2$ enriched environment; E. coli ($2 \times 10^9$ CFU/ml) were then added. The incubations were quenched after 30 min using 2 volumes of ice-cold methanol, then incubated with sodium borohydride (1 μg/ml, 15 min, 4° C.), products extracted and profiled using LM metabololipidomics. The following MRM transitions were employed to monitor each of the new products: RvT1-381>145, RvT2-379>145, RvT3-227 and RvT4-363-145.

Whole blood from healthy volunteers (HV), who declared to exercise for at least 45 mins 2-3 times per week and that they had not taken medications including nonsteroidal anti-inflammatory drugs, ASA-containing products or statins 10-14 days before venipuncture, was obtained after obtaining written consent in accordance with the Declaration of Helsinki and Partners Human Research Committee Protocol 1999P001279 for discarded materials (CNS). Participants rested for 5-10 min in a seated position prior to peripheral blood sampling pre-exercise. Immediately after, the exercise protocol commenced involving 10 min warming up and stretching exercises followed by 30-45 min vigorous intensity continuous cycling or cross-training terminating the exercise when subjects reached ~90% of their theoretical maximum. This was calculated using the formula 220—age in years as in [32]. Blood was collected from these subjects within 15 min of exercise termination. All bloods were collected in heparin, then placed in 4 volumes of ice-cold methanol containing internal standards, and mediator levels were assessed by LC-MS-MS as detailed above.

Plasma from patients diagnosed with sepsis was obtained from Dx Biosamples (see Tables 1 and 2 for demographics). Plasma from healthy volunteers (HV) was collected as outlined above. Human reference plasma denoted SRM 1950 was purchased from the National institute of Standards and Technology (NIST). Plasma from these patients and volunteers was placed in 2 volumes of ice-cold methanol containing internal standards, and mediator levels assessed by LC-MS-MS as detailed above.

Whole blood was collected in heparin at determined time intervals during E. coli infections in mice. This was then placed in 4 volumes of ice-cold methanol containing internal standards, and mediator levels assessed by LC-MS-MS as detailed above.

Neutrophil-Endothelial Co-Incubations

Human umbilical endothelial cells (HUVEC; $8.5 \times 10^5$ cells/9.6 cm$^2$) were incubated with IL-1β (10 ng/ml) and TNF-α (10 ng/ml; 16 h, 37° C., 5% $CO_2$). Cells were then incubated with atorvastatin (30 nM-30 μM), celecoxib (25 μM), L-NAME (25 μM), 1400 W (10 μM) or vehicle (PBS containing 0.01% DMSO) followed by addition of n-3 DPA (1 μM, 1 h, 37° C., 5% $CO_2$). In select experiments, 30 min after n-3 DPA addition, human neutrophils ($1 \times 10^7$ cells/ml) were added and cells incubated for 60 min (37° C., 5% $CO_2$). Incubations were stopped with 2 volumes of ice-cold methanol and products extracted as detailed above. In determined experiments after the addition of human PMN, *E. coli* ($5 \times 10^5$ CFU/ml) were also added and cells incubated 60 min (37° C., 5% $CO_2$). Incubations were then stopped with 2 volumes ice-cold methanol and LM profiles assessed using LM-metabololipidomics.

Endothelial cells were transfected with control scrambled sh-RNA or human COX-2 sh-RNA (Origene) using jet-PEI®-HUVEC (PolyPlus) following manufacturer's instructions, and then incubated with IL-1β (10 ng/ml) and TNF-α (10 ng/ml; 16 h, 37° C., 5% $CO_2$). Cells were then incubated with n-3 DPA (1 μM, 37° C., 5% $CO_2$, in 0.1% EGM). Incubations were stopped with 2 volumes of ice-cold methanol and lipid mediators assessed by lipid mediator metabololipidomics.

Human Neutrophil and Macrophage Phagocytosis and ROS

Macrophages were prepared from peripheral blood mononuclear cells (PBMC) purchased from Children's Hospital Blood Bank, Boston, and phagocytosis was assessed as in[31]. Briefly, macrophages ($5 \times 10^4$ cells/well) were incubated with RvT1 (1 pM-10 nM), 1:1 mixture RvT2 and RvT3 (1 pM-10 nM), RvT4 (1 pM-10 nM) or vehicle (0.1% EtOH in DPBS) for 15 min at 37° C., then fluorescent labeled apoptotic cells were added and cells incubated 45 min at 37° C. Extracellular fluorescence was quenched using Trypan blue (1:15 dilution) and phagocytosis assessed using an M3 SpectraMax plate reader (Molecular Devices). In select experiments, macrophages (prepared as detailed above, $5 \times 10^4$ cells/well) or neutrophils ($1 \times 10^5$ cells/well), obtained from human healthy volunteers and isolated as in [31] in accordance with Partners Human Research Committee Protocol (number 1999P001297), were incubated with H$_2$DCFDA (5 μM, 30 min, 37° C.), excess dye was washed off and cells incubated with RvT1 (1 pM-10 nM), 1:1 mixture RvT2 and RvT3 (1 pM-10 nM), RvT4 (1 pM-10 nM) or vehicle (0.1% EtOH in DPBS, 15 min, 37° C.), then incubated with *E. coli* (1:50 leukocytes to *E. coli*, 45 min, 37° C.). Intracellular reactive oxygen species were determined by measuring fluorescence using an M3 SpectraMax plate reader. To assess bacterial phagocytosis, macrophages ($5 \times 10^4$ cells/well) or neutrophils ($1 \times 10^5$ cells/well) were incubated with RvT1 (1 pM-10 nM), 1:1 mixture RvT2 and RvT3 (1 pM-10 nM), RvT4 (1 pM-10 nM) or vehicle (0.1% EtOH in DPBS, 15 min, 37° C.), then incubated with BacLight Green (Molecular Probes) labeled *E. coli* (1:50 leukocytes to *E. coli*, 45 min, 37° C.). Extracellular fluorescence was then quenched using Trypan blue (1:15 dilution), and phagocytosis was assessed using an M3 SpectraMax plate reader.

Human Macrophage Caspase 1, IL-1β and Lactate Dehydrogenase

Human macrophages ($1.5 \times 10^4$ cells/well) were incubated with RvT1 (10 pM-10 nM), 1:1 mixture RvT2 and RvT3 (10 pM-10 nM), RvT4 (10 pM-10 nM) or vehicle (0.1% EtOH in DPBS, 15 min, 37° C.), then *E. coli* ($7.5 \times 10^5$ cells/well, in DPBS, 16 h, 37° C.). Caspase 1 levels were assessed in macrophages by flow cytometry after cell fixing and permeabilization, staining with an anti-caspase 1 (Abcam; 4° C., 30 min) and anti-rabbit-Alexa 488 conjugated antibody (Molecular Probes; 4° C., 30 min). IL-1β levels were determined in cell-free supernatants using an anti-human IL-1β ELISA (eBiosciences) following manufacturer's instructions. Lactate dehydrogenase activity was measured in cell-free supernatants assessing the formation of NADH from NAD+ using a Lactate Dehydrogenase Assay kit (Sigma) following manufacturer's instructions.

Recombinant Enzyme Incubations

Human recombinant COX-2 (10 units; Cayman Chemicals; in 0.1 M Tris-HCl, pH 8.0, 20 μM porcine hematin, 0.67 mM phenol as in [33]) was incubated with the indicated concentrations of AA or n-3 DPA (1 h, RT) and absorbance at 235 nM was investigated at 1 min intervals using a Cary UV-Vis Spectrophotometer (Agilent).

In designated experiments, n-3 DPA was incubated with hrCOX2, hrCOX-2 that was previously incubated with S-nitrosoglutathione (30 min RT), prepared by incubating 100 mM glutathione with 100 mM sodium nitrite in 200 mM hydrochloric acid at RT as in [34] or S-nitrosoglutathione. After 20 min the incubations were quenched with methanol and 13-HDPA levels were assessed using LC-MS-MS-based LM metabololipidomics.

COX-2 S-nitrosylation was assessed using a Pierce Western Blot S-nitrosylation Kit (Thermo Fisher) following manufacturer's instructions, and total COX-2 levels were determined using a rabbit anti-COX-2 (Cell Signaling) antibody and a goat anti-rabbit-HRP conjugated antibody (eBioscience).

Anti-Bacterial Actions

Neutrophil-endothelial cell isolates, RvT1 (10 μM), RvT2 plus RvT3 (10 μM), RvT4 (10 μM) or ampicillin (1 or 10 mM) were placed on GF-C filters (Waters) that were then transferred onto LB agar plates containing *E. coli* ($1 \times 10^7$ CFU). The zone of clearance was assessed after overnight incubation at 37° C.

Statistics

All results are expressed as means±s.e.m. We assumed normality and equal distribution of variance between the different groups analyzed. Differences between groups were compared using Student's t test (2 groups) or 1-way ANOVA (multiple groups) followed by post hoc Bonferroni test. Survival in mouse experiments was demonstrated with Kaplan-Meier curves and analyzed using log-rank (Mantel-Cox). Investigators were not blinded to group allocation or outcome assessment. Sample sizes for each experiment were determined on the variability observed in preliminary experiments and prior experience with the experimental systems. The criterion for statistical significance was $p < 0.05$.

Results and Discussion

Figure 2:
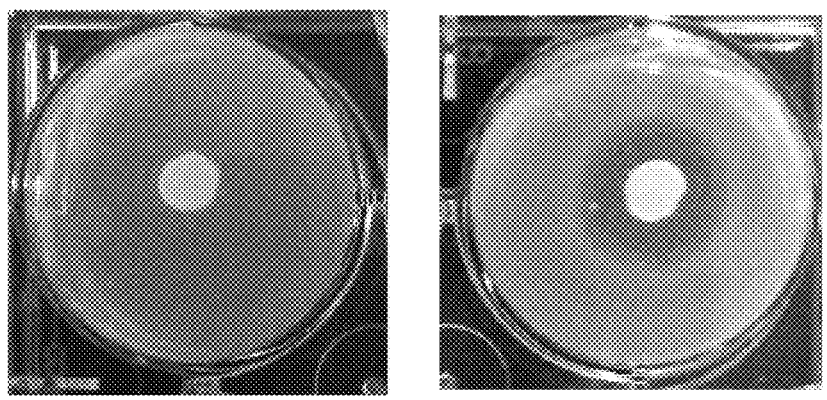
FIG. 2: Neutrophil-endothelial cell products do not display direct antibacterial actions. (a) Fractions were extracted from human (h) neutrophil (PMN)-endothelial cell (EC) co-incubations (see methods). These products or ampicillin (1 mM) were placed on GF-C filters then on LB agar plates containing $E.\ coli$ ($1 \times 107$ CFU). The zone of clearance was assessed after overnight incubation at 37° C. Results are representative of three independent experiments. (b) Proposed structures and biosynthetic scheme for 13-series resolvins (RvT).
Figure 2:
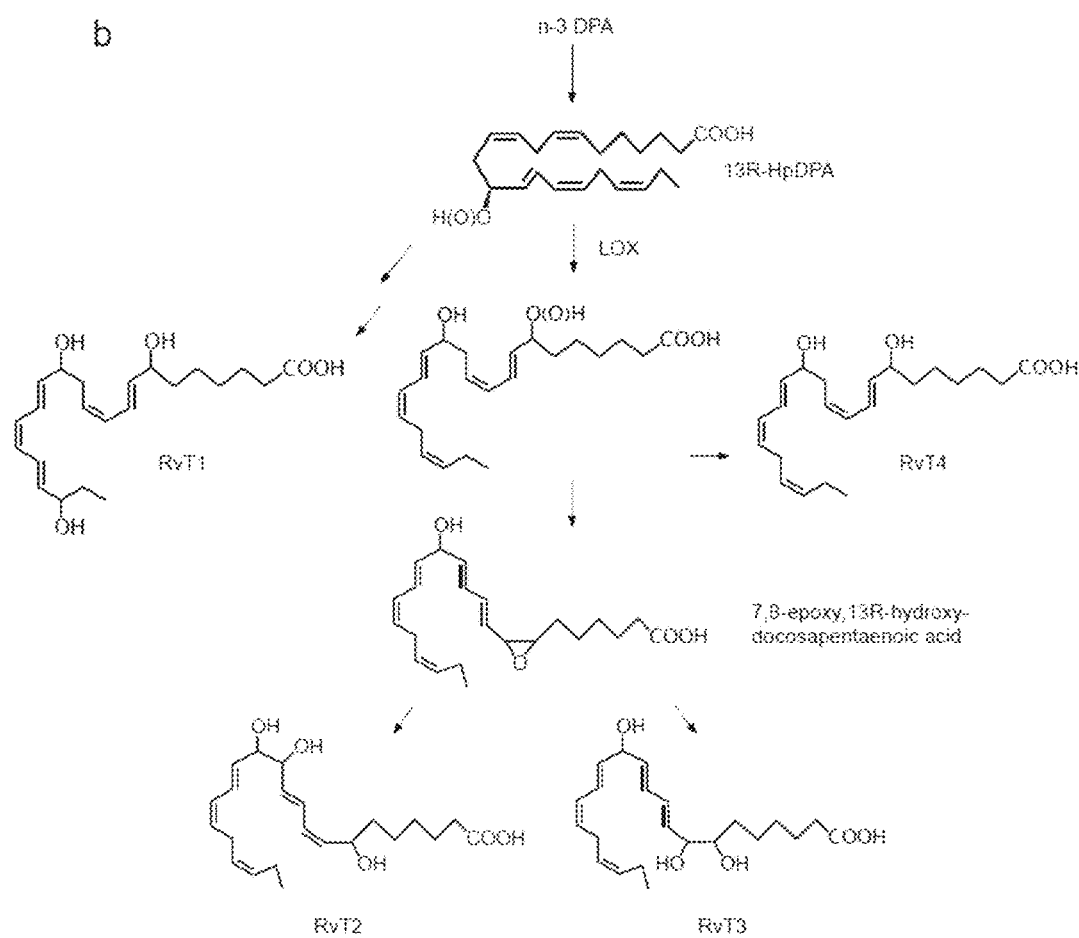

Neutrophils are the first line of defense against invading pathogens[10,11]. They are rapidly recruited from the vasculature to site(s) of infection and participate in bacterial containment and clearance[8]. One of the first steps in recruitment is neutrophil capture onto the vascular endothelium[10]. To identify new molecules that may exert host protective actions produced during this key step and since resolvins and protectins enhance the host clearance of bacterial infections[8], we obtained fractions from co-incubations of these cell types using C18 solid phase extraction (see methods). Given that *E. coli* infections are an urgent worldwide health concern with at least ~270,000 new cases reported per year in the United states alone[12] we next the assessed the actions of these fractions in *E. coli* infections in mice. When administered intravenously immediately prior to *E. coli* inoculation isolates from these human neutrophil-endothelial cell co-incubations significantly enhanced survival from lethal *E. coli* infections (FIG. 1a; p<0.05) and did not display direct antibacterial activity (FIG. 2a).

Figure 3:
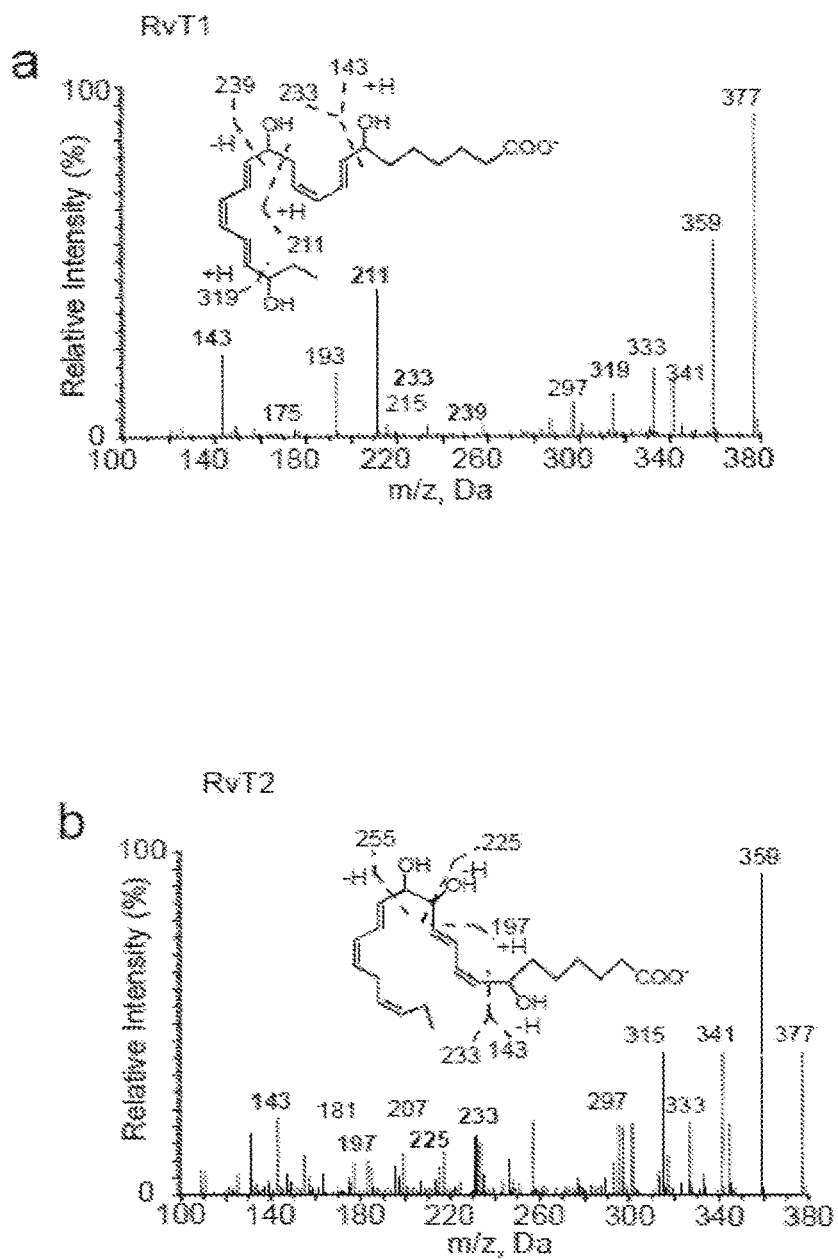
FIG. 3: Identification of novel n-3 docosapentaenoic acid derived 13-series resolvins in neutrophil endothelial co-incubations. (a-d) Fractions were extracted from human neutrophil (hPMN)-endothelial cell (hEC) co-incubations (see methods). Mediators were profiled using lipid mediator (LM) metabololipidomics. MS-MS fragmentation spectra employed for identification of (a) 13-series resolvin (RvT) 1, (b) RvT2, (c) RvT3 and (d) RvT4. Results are representative of n=4 independent cell incubations. (e) hEC were incubated with IL-1β and TNF-α (10 ng/ml each, 16 h, 37° C.), then with vehicle (PBS plus 0.01% EtOH), 1 μM EPA, n-3 DPA or DHA (15 min, 37° C.) and human neutrophils (hPNM; $1 \times 107$ cells/ml, 60 min, 37° C.). Fractions were extracted using solid phase extraction columns, identified and quantified using LC-MS-MS (see methods for details). Results are mean±s.e.m. n=3 cell preparations from two independent experiments. *p<0.05, **p<0.01 vs hPMN-EC incubations. (f) hEC), hPMN and hPMN-EC were incubated with n-3 DPA (see methods for details) and RvT identified and quantified using LC-MS-MS based LM metabololipidomics. RvT1, RvT2, RvT3 and RvT4 levels identified in neutrophil-endothelial cell co-cultures. Results are mean±s.e.m. n=4 cell preparations per group from four independent experiments. *p<0.05 vs. amounts in hEC.
Figure 3:
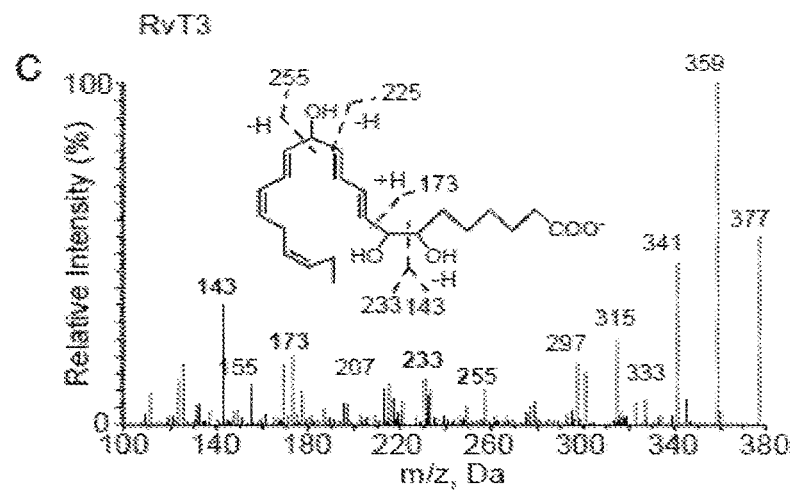
Figure 3:
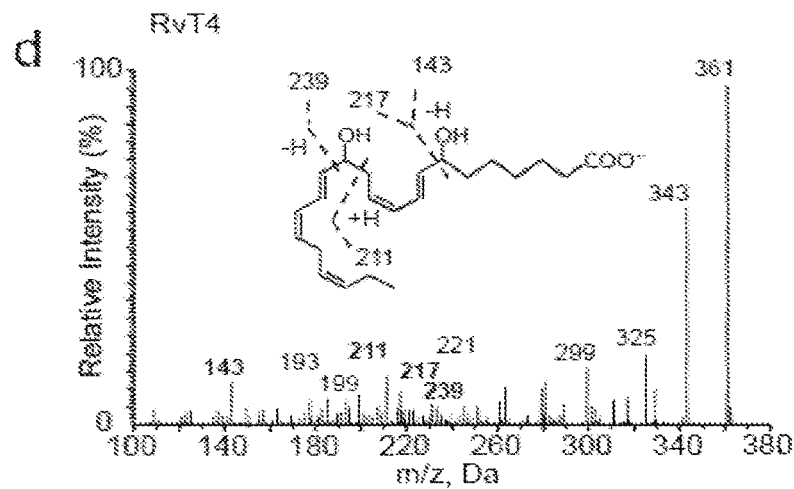
Figure 3:
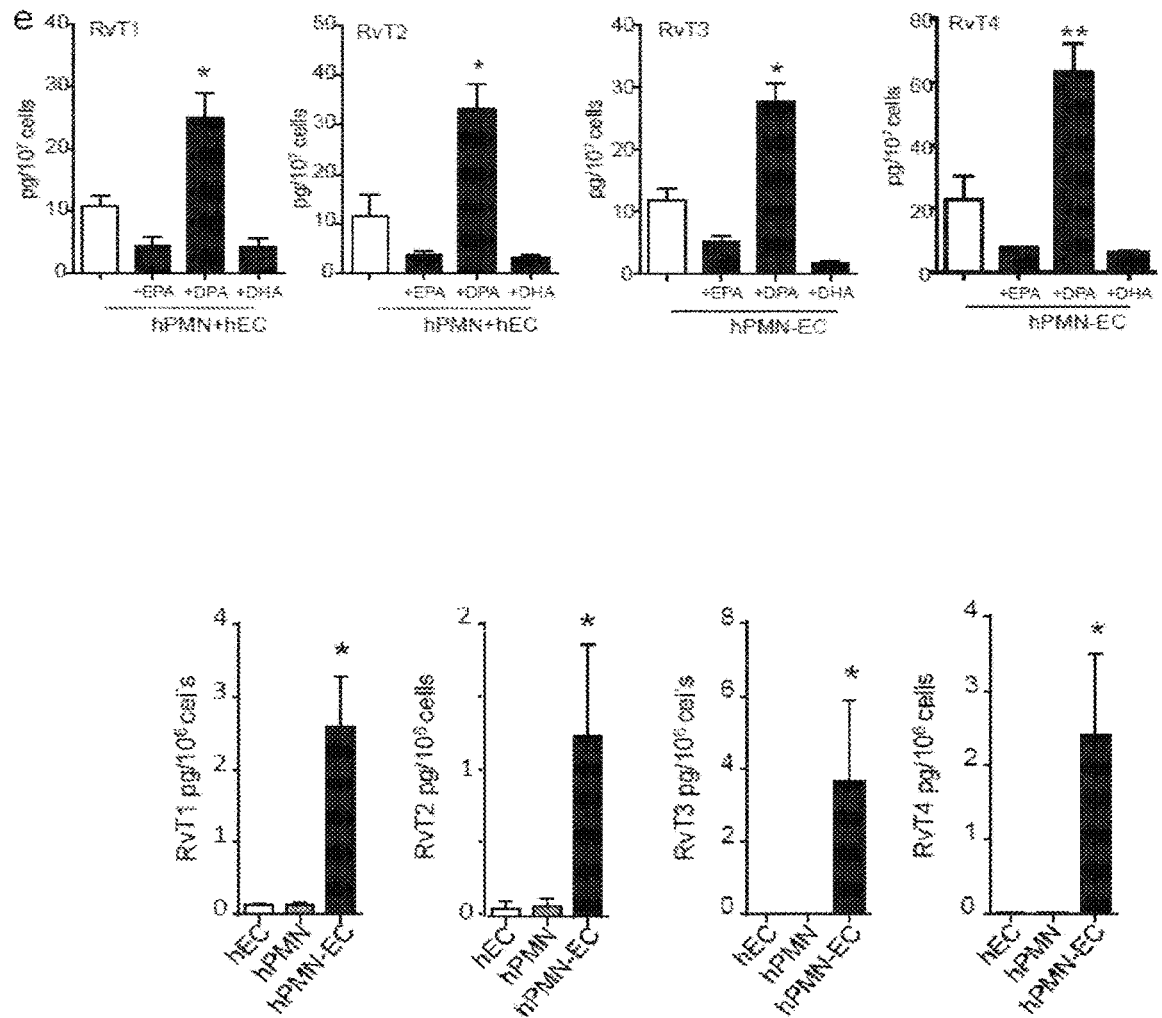

To characterize and elucidate bioactive molecule(s) within these fractions and deduce their structure(s), the inventors initially used liquid chromatography tandem mass-spectrometry (LC-MS-MS) based lipid mediator (LM)-metabololipidomics. Along with classic eicosanoids and SPM, identified also were previously unknown molecules in fractions that showed activity from neutrophil-endothelial cell co-incubations. These gave four distinct MS-MS spectra and retention times characteristic of a 22-carbon backbone with five double bonds suggesting DPA was the precursor[7]. Using MS-MS fragmentations structures were deduced of these new n-3 DPA derived bioactive molecules as: 7,13,20-trihydroxy-docosapentaenoic acid, 7,8,13-trihydroxy-docosapentaenoic, 7,12,13-trihydroxy-docosapentaenoic acid and 7,13-dihydroxy-docosapentaenoic acid (FIG. 1b and FIGS. 2b and 3a-d). Their assignments were confirmed using physical characteristics including MS-MS of different chemical derivatives and reactivity (i.e. $^{18}O_2$ incorporation, acid methanol trapping and methyl ester vide infra and online methods) for each product. Co-incubations of neutrophil-endothelial cells with n-3 DPA, but neither DHA nor EPA precursors to SPM[4,9], increased their amounts 30-50% (FIG. 3e). Thus these new bioactive structures were denoted 13-series resolvins (RvT), RvT1, RvT2, RvT3 and. RvT4 respectively, since each carried a carbon-13 position alcohol from their biosynthetic origin (FIG. 2b).

Since in humans exercise leads to a self-resolving inflammatory state marked by increases in plasma lipid mediators[13], RvT production was investigated in healthy volunteers during exercise. Significant increases in peripheral blood RvT were obtained when compared to pre-exercise levels (FIG. 1c, Table 1a; p<0.05). Their amounts were comparable in magnitude to those from the AA, EPA or DHA bioactive-metabolomes, namely prostaglandins, leukotriene $B_4$, resolvins, protectins and maresins (Table 1b). RvT were also present in human peripheral blood from sepsis patients (FIG. 1d, Table 2a) and when compared to amounts in plasma from healthy volunteers and those in a human plasma composite obtained from the National Institutes for Standards and Technologies (SRM1950). Resolvins and lipoxins were also increased in sepsis patient plasma when compared to both healthy volunteer plasma and the SRM1950 plasma composite (Table 2b).

TABLE 1

Peripheral blood lipid mediator profiles pre and post-exercise in healthy Volunteers 1a

| Sex | Age (years) | Weight (Kg) | BMI (Kg/m$^2$) |
|---|---|---|---|
| 2 M/2 F | 30-46 | 64.8 ± 5.4 | 22.7 ± 0.7 |

1b

| | Pre-Exercise (pg/ml) | Post-Exercise (pg/ml) |
|---|---|---|
| DHA Bioactive Metabolome | | |
| RvD1 | 1.0 ± 0.3 | 4.6 ± 0.3 |
| RvD2 | 1.1 ± 0.3 | 1.5 ± 0.4 |

TABLE 1-continued

Peripheral blood lipid mediator profiles pre and post-exercise in healthy Volunteers

| | | |
|---|---|---|
| RvD3 | 0.4 ± 0.2 | 0.5 ± 0.2 |
| RvD5 | 0.7 ± 0.2 | 0.9 ± 0.7 |
| RvD6 | 37.8 ± 12.3 | 56.0 ± 23.3 |
| MaR1 | * | * |
| PD1 | 0.3 ± 0.1 | 0.5 ± 0.2 |
| n-3 DPA Bioactive Metabolome | | |
| RvT1 | 1.8 ± 0.8 | 3.6 ± 0.4 |
| RvT2 | 0.6 ± 0.1 | 2.7 ± 0.8 |
| RvT3 | 0.8 ± 0.4 | 1.8 ± 0.5 |
| RvT4 | 0.8 ± 0.4 | 1.8 ± 0.5 |
| EPA Bioactive Metabolome | | |
| RvE1 | 0.6 ± 0.2 | 1.5 ± 0.9 |
| RvE2 | 39.1 ± 19.3 | 32.5 ± 23.4 |
| RvE3 | 29.1 ± 11.1 | 69.3 ± 14.6 |
| AA Bioactive Metabolome | | |
| $LXA_4$ | 3.6 ± 1.7 | 8.0 ± 5.3 |
| $LXB_4$ | 7.4 ± 4.0 | 19.3 ± 8.4 |
| 5,15-diHETE | 74.0 ± 22.6 | 89.1 ± 52.7 |
| $LTB_4$ | 4.5 ± 1.7 | 14.4 ± 7.0 |
| $PGD_2$ | 6.5 ± 2.7 | 31.2 ± 16.8 |
| $PGE_2$ | 115.2 ± 59.8 | 148.4 ± 78.5 |
| $PGF_{2\alpha}$ | 4.4 ± 1.5 | 12.9 ± 10.3 |
| 8-iso-$PGF_{2\alpha}$ | 6.6 ± 5.4 | 3.9 ± 2.3 |
| $TxB_2$ | 4.8 ± 4.1 | 36.2 ± 9.9 |
| 12-HHT | 109.0 ± 68.1 | 177.6 ± 55.1 |

(a) Healthy volunteer demographics
(b) Peripheral blood was collected from healthy volunteers pre- and post-exercise (see methods) and lipid mediator levels quantified using MRM monitoring of the parent ion in Q1 and a characteristic fragment ion in Q3.
Results are expressed as mean ± s.e.m.
n = 4 healthy volunteers from four independent experiments.
* = below limits; limits ~0.1 pg.
Numbers denoted in bold are p < 0.05 vs. pre-exercise values.

TABLE 2

Comparison of SPM and Eicosanoids versus novel RvT in plasma from healthy volunteers and sepsis patients 2a

| Samples | Sex | Age (years) | Blood Culture |
|---|---|---|---|
| Sepsis Patients | 5 F/5 M | 57-96 | 1/10 *Salmonella* sp |
| | | | 1/10 *Streptococcus pyogenes* |
| | | | 2/10 *Staphylococcus hominis* |
| | | | 3/10 *Corynebacterium* sp. |
| | | | 1/10 *S. infantarius* |
| | | | 1/10 *S. viridans* |
| | | | 1/10 *S maltophilla* |
| Healthy | 3 F/3 M | 33-65 | N/A |
| SRM 1950 | 50 M/50 F | 40-50 | N/A |

2b

| | Reference Plasma | Healthy Volunteer | Sepsis Patients Plasma (pg/ml) |
|---|---|---|---|
| DHA Bioactive Metabolome | | | |
| RvD1 | 0.8 ± 0.4 | 1.8 ± 1.4 | 4.6 ± 2.1 |
| RvD2 | 0.9 ± 0.3 | 1.5 ± 1.0 | 3.7 ± 1.3 |
| RvD3 | * | * | 10.5 ± 5.5 |
| RvD5 | 0.8 ± 0.3 | 0.9 ± 0.5 | 17.0 ± 6.9 |
| RvD6 | 1.5 ± 0.2 | 27.6 ± 7.2 | 121.8 ± 31.8 |

TABLE 2-continued

Comparison of SPM and Eicosanoids versus novel RvT in plasma from healthy volunteers and sepsis patients

| | | | |
|---|---|---|---|
| MaR1 | * | * | 7.4 ± 3.4 |
| PD1 | * | 1.2 ± 0.8 | 1.5 ± 0.7 |
| n-3 DPA Bioactive Metabolome | | | |
| RvT1 | 5.0 ± 1.7 | 2.9 ± 0.6 | 6.6 ± 1.1 |
| RvT2 | 2.2 ± 1.3 | 1.2 ± 0.3 | 10.0 ± 1.8 |
| RvT3 | 1.0 ± 0.2 | 0.9 ± 0.4 | 17.5 ± 3.2 |
| RvT4 | 7.3 ± 3.1 | 1.4 ± 0.6 | 15.2 ± 3.3 |
| EPA Bioactive Metabolome | | | |
| RvE1 | * | 2.2 ± 1.2 | 11.0 ± 5.3 |
| RvE2 | * | 3.7 ± 0.9 | 24.7 ± 11.2 |
| RvE3 | 1.5 ± 0.5 | 8.9 ± 2.6 | 361.3 ± 241.5 |
| AA Bioactive Metabolome | | | |
| LXA$_4$ | * | 0.8 ± 0.4 | 5.5 ± 2.4 |
| LXB$_4$ | 8.7 ± 2.7 | 3.2 ± 1.5 | 56.7 ± 20.5 |
| 5,15-diHETE | 4.2 ± 1.7 | 6.2 ± 1.1 | 87.1 ± 55.7 |
| LTB$_4$ | 25.2 ± 3.1 | 3.7 ± 2.2 | 3.3 ± 1.2 |
| PGD$_2$ | 7.3 ± 1.2 | 9.8 ± 4.4 | 79.4 ± 24.1 |
| PGE$_2$ | 17.8 ± 5.1 | 24.1 ± 9.7 | 132.1 ± 22.2 |
| PGF$_{2a}$ | 1.7 ± 0.7 | 4.2 ± 0.6 | 51.0 ± 10.2 |
| 8-iso-PGF$_{2a}$ | 4.5 ± 1.0 | 1.9 ± 1.0 | 11.8 ± 5.3 |
| TxB$_2$ | 6.3 ± 3.2 | 10.5 ± 6.3 | 185.4 ± 96.5 |
| 12-HHT | 21.8 ± 1.0 | 39.6 ± 13.8 | 127.7 ± 89.9 |

(a) healthy volunteer demographics and patient demographics and cultures.
(b) Plasma was obtained from the NIST repository (reference plasma; d = 3); collected from healthy volunteers (n = 4) or patients diagnosed with sepsis (n = 9), and lipid mediator levels quantified using MRM monitoring of the parent ion in Q1 and a characteristic fragment ion in Q3.
Results are expressed as mean ± s.e.m. from two independent experiments.
*below limits; limits ~0.1 pg.
Numbers denoted in bold are $p < 0.05$ vs reference plasma values.

The temporal regulation of RvT was then assessed during bacterial infections in mice. FVB mice challenged with *E. coli* $10^5$ CFU *E. coli*/mouse had a self-resolving (i.e. self-limited) inflammatory response with PMN numbers reaching a maximum at ~12 h followed by their decline[8]. RvT were rapidly formed during the initiation phase of inflammation with amounts in peripheral blood reaching a maximum at 4 h that subsequently declined (FIG. 1e). By comparison, mediators derived from AA-, EPA- and DHA-derived mediators also increased at 4 h with the majority reaching maximum at 12 h. These included RvD2 and LXB$_4$ (Table 3). Notably, RvT were >60% lower in peripheral blood from mice challenged with a higher *E. coli* burden that was non-lethal but caused increased inflammation with delayed resolution ($10^7$ CFU/mouse; FIG. 1f and Table 4).

TABLE 3

Peripheral blood lipid mediator profiles during self-resolving infections in mice.

| | 0 h | 4 h | 12 h | 24 h | 48 h (pg/ml) |
|---|---|---|---|---|---|
| DHA Bioactive | | | | | |
| RvD1 | 5.5 ± 3.5 | 51.0 ± 22.8 | 27.6 ± 13.6 | 12.8 ± 2.8 | 15.5 ± 7.4 |
| RvD2 | 8.1 ± 3.2 | 16.0 ± 6.1 | 22.7 ± 5.2 | 4.0 ± 0.9 | 2.2 ± 0.9 |
| RvD3 | 2.6 ± 1.0 | 6.3 ± 3.4 | 2.7 ± 0.6 | 1.1 ± 0.3 | 6.1 ± 4.6 |
| RvD5 | 22.7 ± 4.4 | 16.9 ± 2.5 | 25.1 ± 8.1 | 8.7 ± 1.0 | 9.2 ± 1.7 |
| RvD6 | 51.4 ± 18.4 | 346.8 ± 82. | 435.8 ± 51.6 | 259.3 ± 49.3 | 219.4 ± 60.7 |
| MaR1 | * | * | * | * | * |
| PD1 | 1.8 ± 1.2 | 4.2 ± 1.8 | 4.1 ± 1.4 | 3.0 ± 0.8 | 3.9 ± 1.2 |
| n-3 DPA Bioactive Metabolome | | | | | |
| RvT1 | 6.4 ± 2.1 | 34.6 ± 3.3 | 12.6 ± 2.9 | 6.8 ± 2.6 | 10.3 ± 3.3 |
| RvT2 | 9.4 ± 3.2 | 50.3 ± 10. | 14.1 ± 2.3 | 5.2 ± 1.2 | 5.2 ± 0.8 |
| RvT3 | 11.5 ± 6.0 | 32.7 ± 4.6 | 16.4 ± 1.3 | 3.3 ± 1.1 | 5.2 ± 1.1 |
| RvT4 | 10.2 ± 1.5 | 45.5 ± 3.5 | 10.4 ± 1.7 | 5.1 ± 1.4 | 4.8 ± 0.5 |
| EPA Bioactive Metabolome | | | | | |
| RvE1 | 0.6 ± 0.4 | 0.2 ± 0.3 | 2.2 ± 2.6 | 0.6 ± 0.2 | 2.7 ± 1.2 |
| RvE2 | 14.0 ± 2.2 | 88.5 ± 26. | 139.0 ± 37.1 | 85.0 ± 27.9 | 44.4 ± 17.9 |
| RvE3 | 39.4 ± 4.5 | 229.4 ± 47. | 356.3 ± 51.7 | 155.7 ± 20.2 | 104.9 ± 40.5 |
| AA Bioactive Metabolome | | | | | |
| LXA4 | 12.6 ± 4.1 | 39.9 ± 23. | 70.7 ± 26.8 | 16.7 ± 5.3 | 46.0 ± 15.1 |
| LXB4 | 41.1 ± 13.5 | 73.9 ± 22. | 143.9 ± 59.7 | 37.2 ± 8.5 | 36.2 ± 7.0 |
| 5,15-diHETE | 95.0 ± 4.6 | 121.1 ± 19. | 51.6 ± 20.5 | 36.4 ± 9.1 | 19.2 ± 4.3 |
| LTB4 | 0.7 ± 0.4 | 100.3 ± 18. | 35.9 ± 6.7 | 12.0 ± 2.8 | 106.9 ± 42.0 |
| PGD2 | 7.7 ± 0.9 | 353.5 ± 11. | 273.4 ± 50.0 | 77.3 ± 20.6 | 106.3 ± 17.7 |
| PGE2 | 9.2 ± 1.4 | 1602.0 ± 517 | 1775.6 ± 302.8 | 323.0 ± 196.8 | 414.3 ± 117.2 |
| PGF2$_a$ | 3.3 ± 0.1 | 153.0 ± 64. | 57.5 ± 19.4 | 12.2 ± 3.3 | 26.7 ± 6.5 |
| 8-iso-PGF2$_a$ | 8.1 ± 0.9 | 227.6 ± 45. | 255.0 ± 96.6 | 64.5 ± 16.8 | 71.6 ± 25.3 |

TABLE 3-continued

Peripheral blood lipid mediator profiles during self-resolving infections in mice.

| | | | | | |
|---|---|---|---|---|---|
| TxB2 | 24.9 ± 9.5 | 1773.7 ± 514 | 471.4 ± 174.6 | 214.3 ± 26.0 | 176.5 ± 22.0 |
| 12-HHT | 89.8 ± 24.2 | 12598.1 ± 425 | 12879.5 ± 772.7 | 3208.8 ± 871.5 | 4237.5 ± 750.0 |

Mice were inoculated with *E. coli* ($1 \times 10^5$ CFU/mouse), blood was collected at the indicated intervals and lipid mediator levels quantified using MRM monitoring of the parent ion in Q1 and a characteristic fragment ion in Q3.
Results are expressed as mean ± s.e.m.
n = 4 mice per group from two independent experiments.
* = below limits limits ~0.1 pg.
Numbers denoted in bold are p < 0.05 vs. 0 h values.

TABLE 4

Mouse peripheral blood lipid mediator profiles during self-resolving and delayed-resolving infections.

| | Self-Resolving Infections | Delayed-Resolving Infections |
|---|---|---|
| BHA Bioactive Metabolome | | |
| RvD1 | 9.8 ± 1.1 | 3.5 ± 1.3 |
| RvD2 | 9.4 ± 2.6 | 7.4 ± 1.5 |
| RvD3 | 5.7 ± 1.2 | 1.3 ± 0.2 |
| RvD5 | 63.6 ± 13.8 | 113.2 ± 29.1 |
| RvD6 | 55.2 ± 3.7 | 20.6 ± 10.4 |
| MaR1 | 0.3 ± 0.1 | 0.2 ± 0.2 |
| PD1 | 4.2 ± 1.1 | 6.9 ± 3.0 |
| n-3 DPA Bioactive Metabolome | | |
| RvT1 | 40.6 ± 9.4 | 19.9 ± 3.6 |
| RvT2 | 55.8 ± 9.1 | 21.7 ± 2.9 |
| RvT3 | 41.8 ± 3.5 | 7.9 ± 1.8 |
| RvT4 | 36.4 ± 2.0 | 19.7 ± 3.9 |
| EPA Bioactive Metabolome | | |
| RvE1 | 21.5 ± 6.8 | 13.0 ± 2.6 |
| RvE2 | 5.2 ± 1.6 | 2.8 ± 0.9 |
| RvE3 | 39.0 ± 14.0 | 32.6 ± 8.7 |
| AA Bioactive Metabolome | | |
| LXA4 | 3.2 ± 1.1 | 2.6 ± 1.6 |
| LXB4 | 50.7 ± 5.7 | 25.1 ± 5.1 |
| 5,15-diHETE | 22.6 ± 6.4 | 29.2 ± 13.2 |
| LTB4 | 0.5 ± 0.0 | 2.3 ± 0.6 |
| PGD2 | 6.3 ± 2.3 | 14.3 ± 1.7 |
| PGE2 | 2.7 ± 0.8 | 6.7 ± 2.8 |
| PGF$_{2\alpha}$ | 2.1 ± 0.6 | 1.5 ± 0.4 |
| 8-iso-PGF$_{2\alpha}$ | 4.4 ± 2.2 | 20.1 ± 1.5 |
| TxB2 | 4.4 ± 2.2 | 21.6 ± 2.6 |
| 12-HHT | 12.3 ± 2.0 | 31.3 ± 3.8 |

Mice were inoculated with $1 \times 10^5$ CFU/mouse *E. coli* (self-resolving) or $1 \times 10^7$ CFU/mouse *E. coli* (delayed resolving), blood was collected after 4 h and lipid mediator levels quantified using MRM monitoring of the parent ion in Q1 and a characteristic fragment ion in Q3.
Results are expressed as mean ± s.e.m.
n = 5 mice per group from two independent experiments.
Numbers denoted in bold are p < 0.05 vs. self resolving values.

Figure 5:
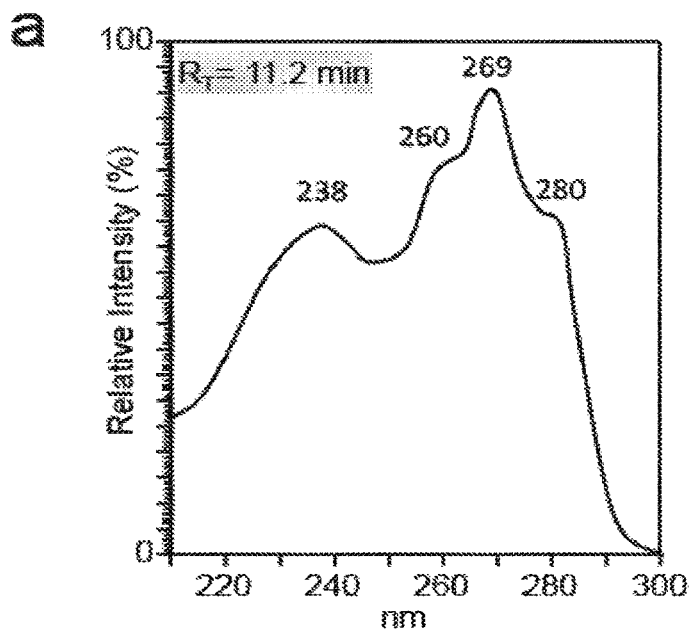
FIG. 5: Physical characteristics of RvT1, RvT2, RvT3 and RvT4. 13R-HDPA was incubated with potato 5-LOX (0.1 M phosphate buffer, pH 6.3, 0.03% Tween 20, 30 min); products were isolated using RP-UV-HPLC (see methods for details). (a-d) In phase, online UV-chromophores recorded for (a) RvT1, (b) RvT2, (c) RvT3, (d) RvT4. (e-h) Isolated products were incubated with diazomethane in ether (30 min, Room Temperature) and assessed by LM metabololipidomics. MS-MS fragmentation spectra for the sodium adducts of (e) RvT1-methyl ester, (f) RvT2-methyl ester, (g) RvT3-methyl ester and (h) RvT4-methyl ester. Results are representative of three independent experiments.
Figure 5:
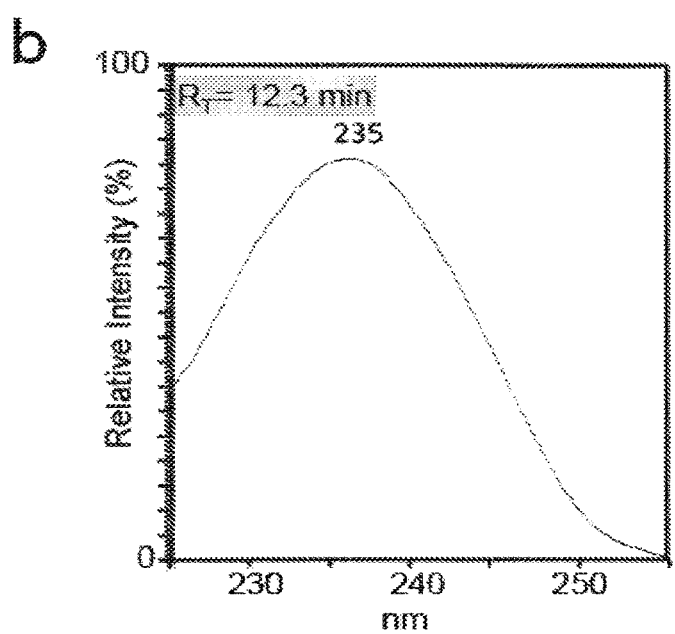
Figure 5:
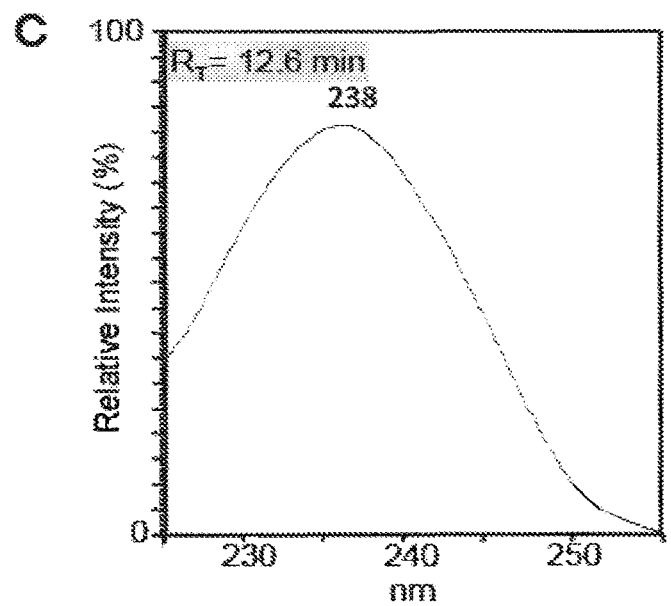
Figure 5:
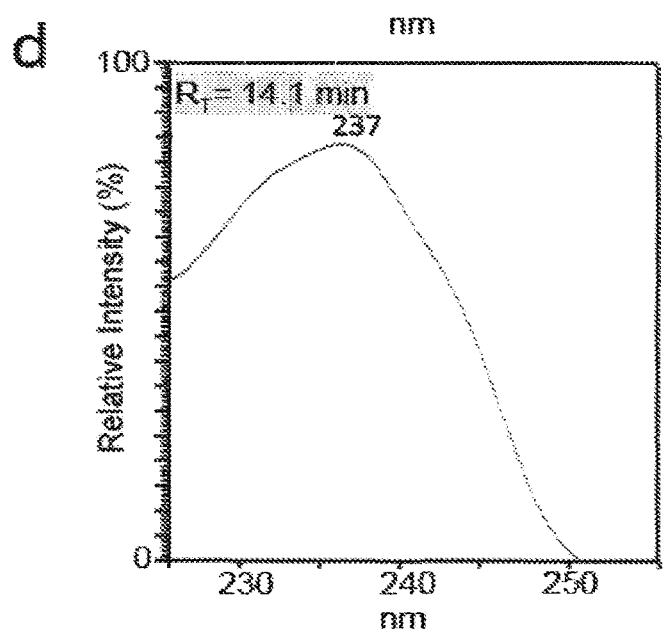
Figure 5:
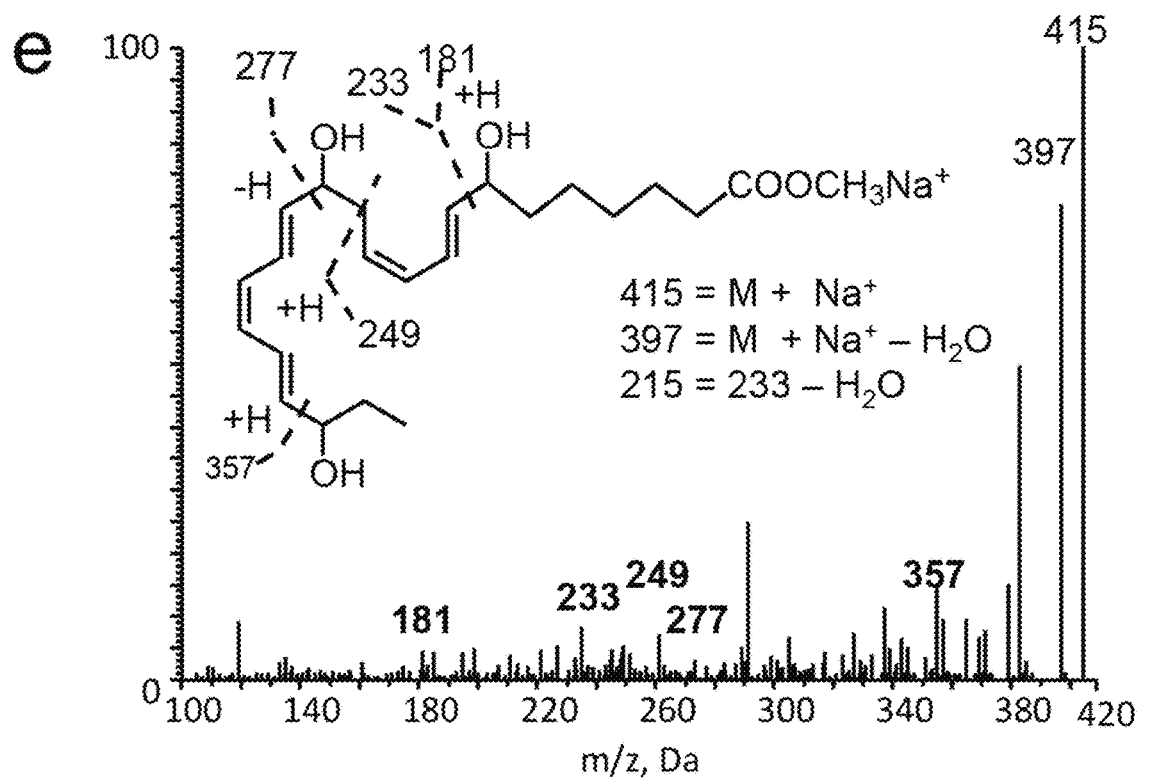
Figure 5:
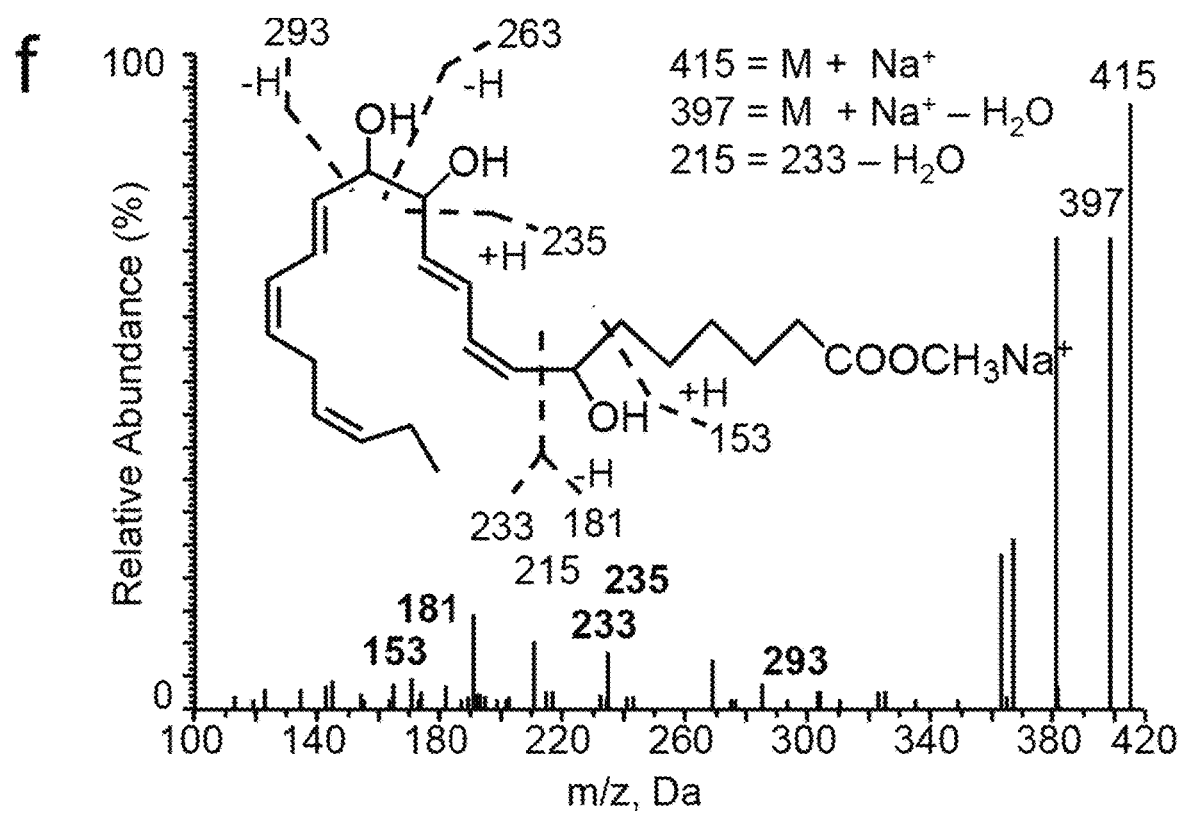
Figure 5:
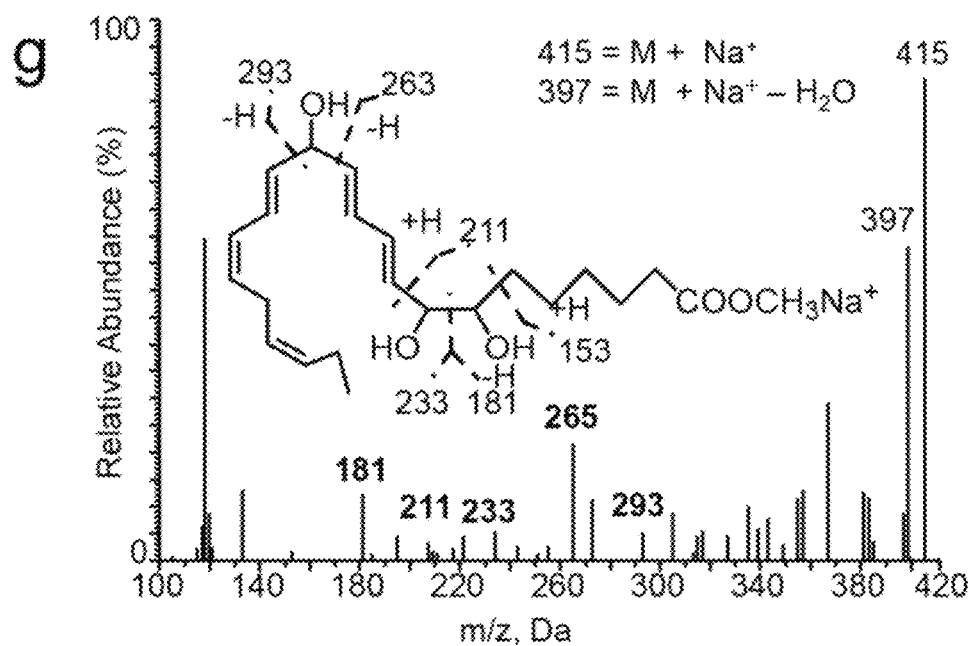
Figure 5:
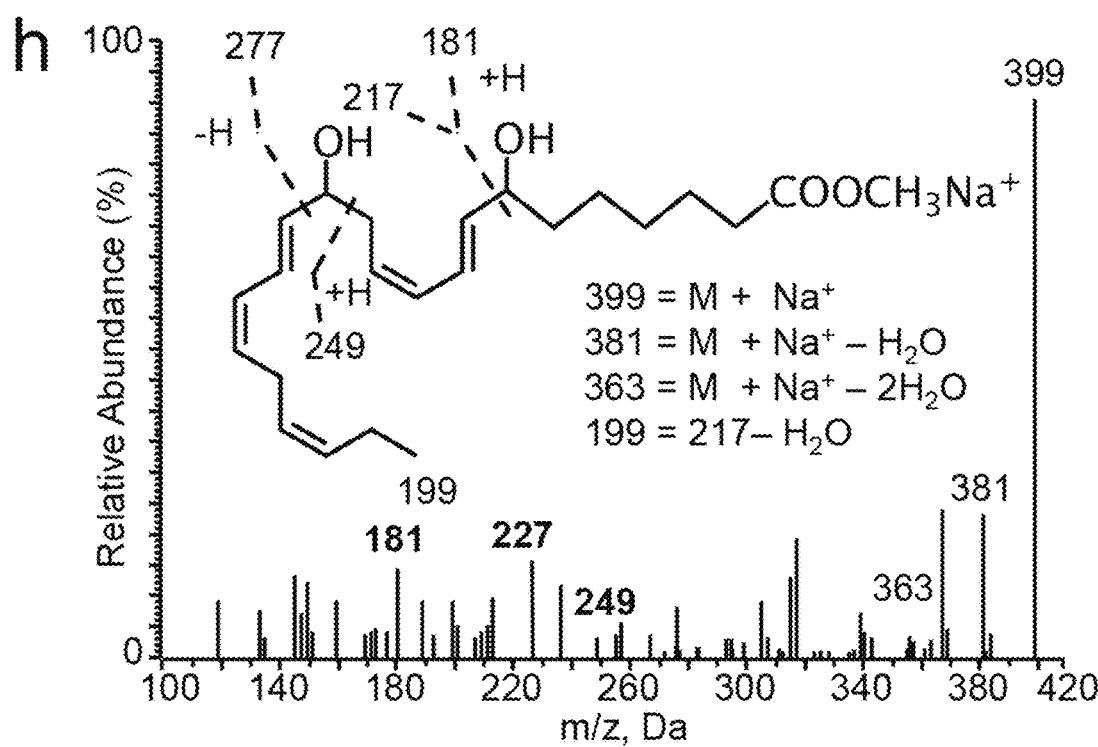
Figure 6:
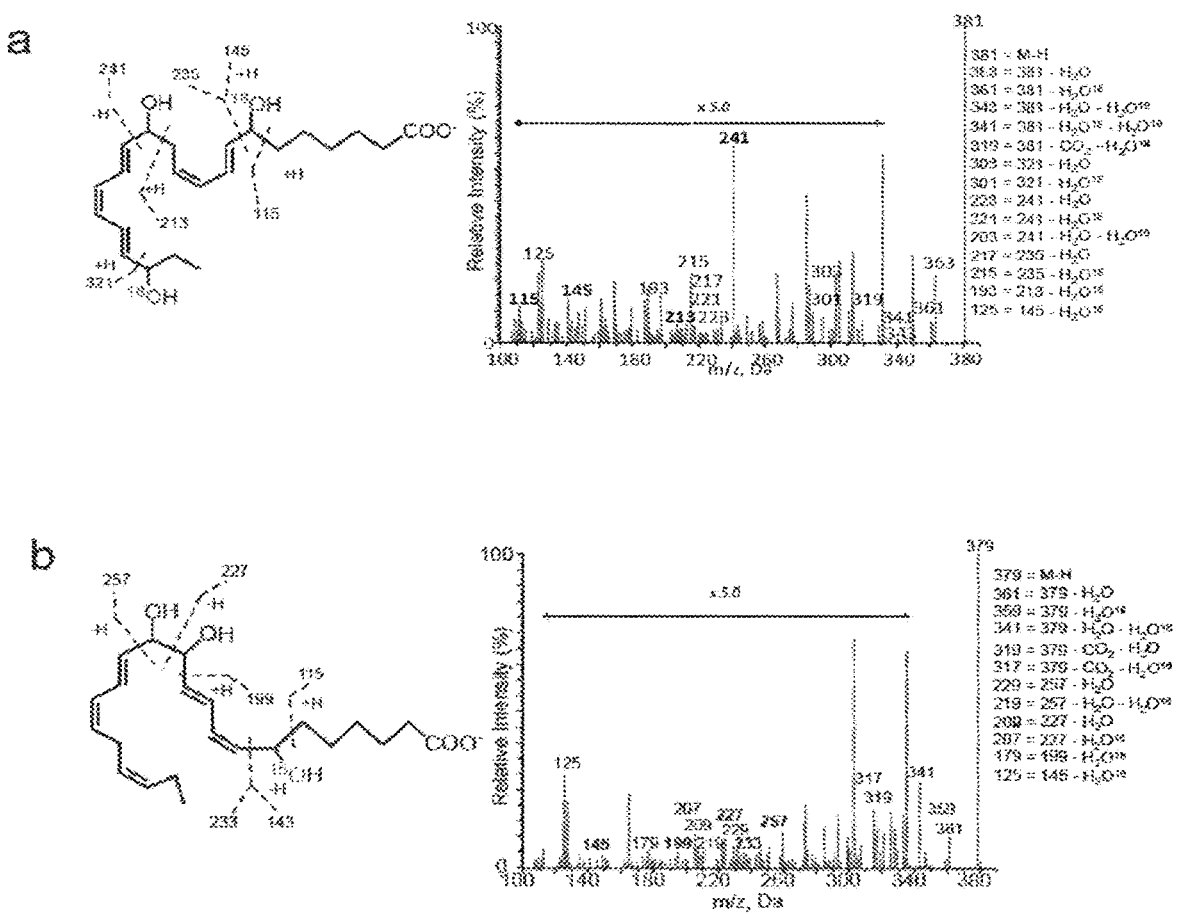
FIG. 6: Molecular oxygen incorporation demonstrates a role for neutrophil lipoxygenases in the biosynthesis of the novel RvT. Human peripheral blood neutrophils (5×107/ml) were incubated with 13-HPDA (75 ng/ml; PBS+/+; pH7.45) in an atmosphere enriched in $^{18}O_2$. E. coli were then added (2.5×109/ml), incubations quenched after 30 min (37° C.) using 2 volumes of ice-cold methanol and products reduced using sodium borohydride (1 µg/ml, 15 min, 4° C.). Products were extracted, and identified using LC-MS-MS. (a-d) Representative structures and MS-MS spectra employed in the identification of (a) RvT1, (b) RvT2, (c) RvT3 and (d) RvT4. Results are representative of 4 neutrophil preparations from four independent experiments.
Figure 6:
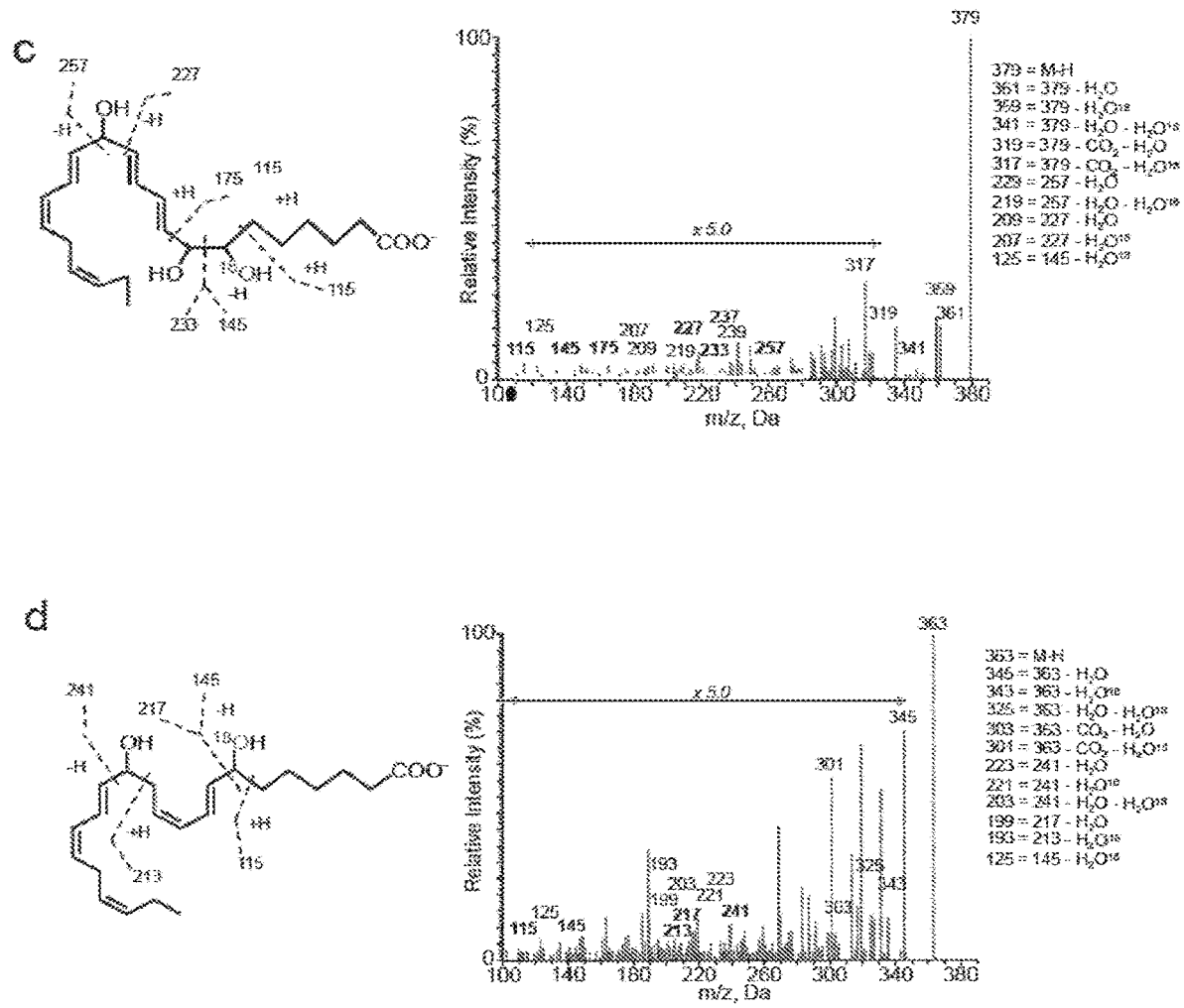
Figure 7:
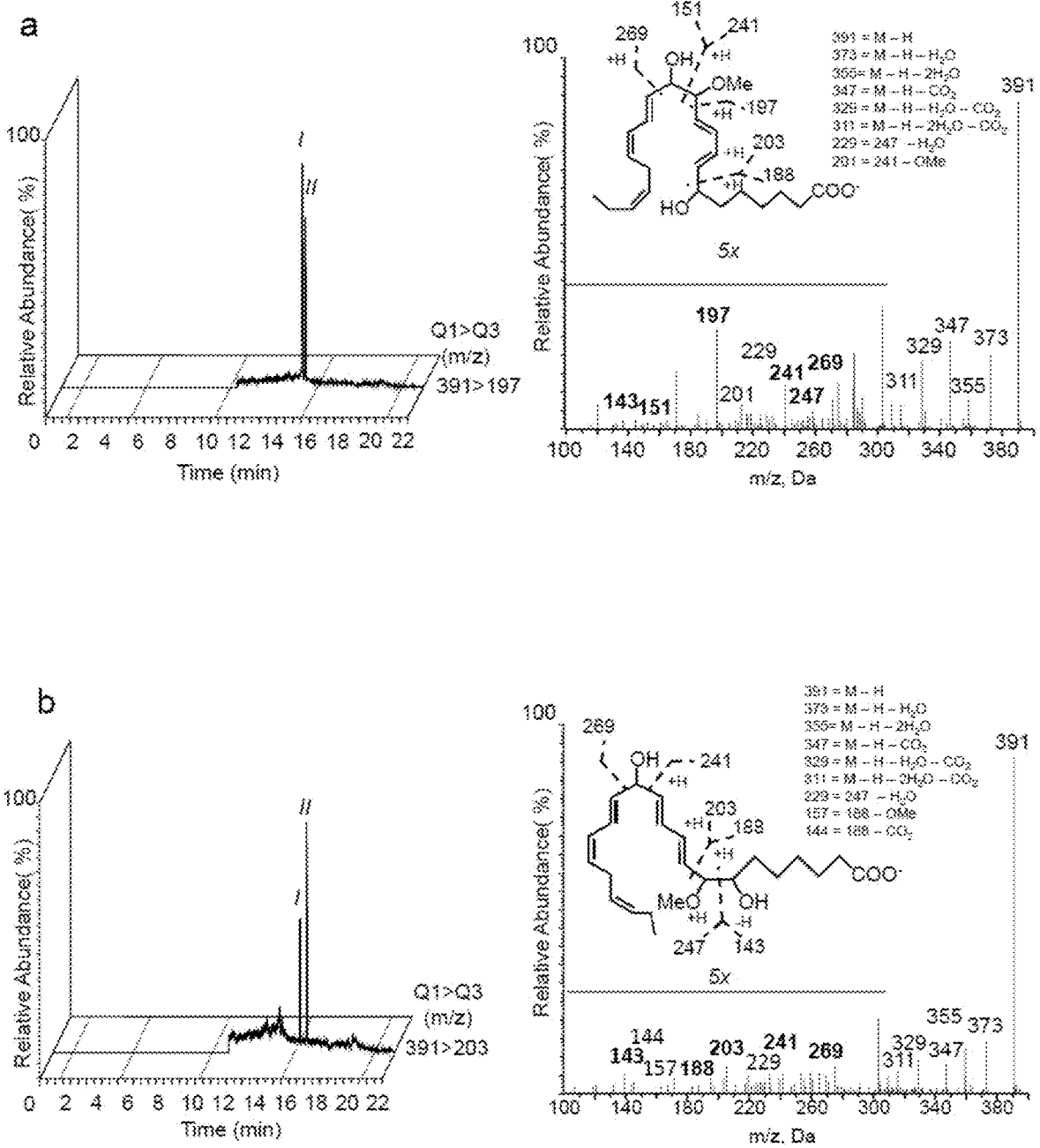
FIG. 7: Trapping products indicate the formation of an epoxide intermediate in RvT2 and RvT3 biosynthesis. Human neutrophils (5×107 cells/ml) were incubated with 13R-HDPA (1 µM, 37° C., PBS pH 7.45) and E. coli (1×109 CFU/ml, 2 min, 37° C.). Incubations were stopped with 2 volumes of acidified methanol (apparent pH 3), the products extracted and profiled using LM metabololipidomics. (a) MRM chromatogram for the methoxy-trapping products of RvT2 (left panel) and MS-MS spectra (right panel). (b) MRM chromatogram for the methoxy-trapping products of RvT3 (left panel) and MS-MS spectra (right panel). Results are representative of three independent experiments.

Based on human neutrophil-endothelial cell co-incubations it was speculated that RvT were products of transcellular biosynthesis because these co-incubations gave appreciable amounts of RvT1, RvT2, RvT3 and RvT4 (FIG. 3F). Chiral LC-MS-MS demonstrated that endothelial cells incubated with n-3 DPA gave increased 13R-hydroxy-7Z,10Z,14Z,16Z,19Z-docosapentaenoic acid (13R-HDPA, FIG. 4a-d) when compared to cells kept in culture medium alone. Since IL-1β and TNF-α up-regulate endothelial COX-2 expression[14], which converts DHA to 13-hydroxy-docosahexaenoic acid[9], it was questioned whether endothelial COX-2 also converts n-3 DPA to produce 13-HDPA. Incubations of endothelial cells with celecoxib, a COX-2 selective inhibitor, or transfection of endothelial cells with shRNA targeting COX-2, each led to significant reductions in endothelial cell derived 13-HDPA (Supplementary FIGS. 3e,f; p<0.05), indicating a role for COX-2 in 13-HDPA production. Incubations of n-3 DPA with human recombinant COX-2 gave 13R-HDPA (FIG. 4g) with $K_M$=3.1±1.3 μM (Supplementary FIG. 3h), suggesting that n-3 DPA is converted to 13R-HpDPA by endothelial COX-2. This intermediate or its reduced alcohol form may then be donated to neutrophils that convert the intermediate(s) to RvT. This proposed biosynthetic route and the RvT structures were corroborated by assessing UV chromophores, MS-MS fragmentation spectra for methyl-ester derivatives (FIG. 5), molecular oxygen ($^{18}O_2$) incorporation (FIG. 6) and acid-alcohol trapping of epoxide intermediates (FIG. 7). These results indicate that COX-2 derived 13-HDPA is converted via lipoxygenation in human neutrophils to RvT1, RvT2, RvT3 and RvT4.

Figure 8:
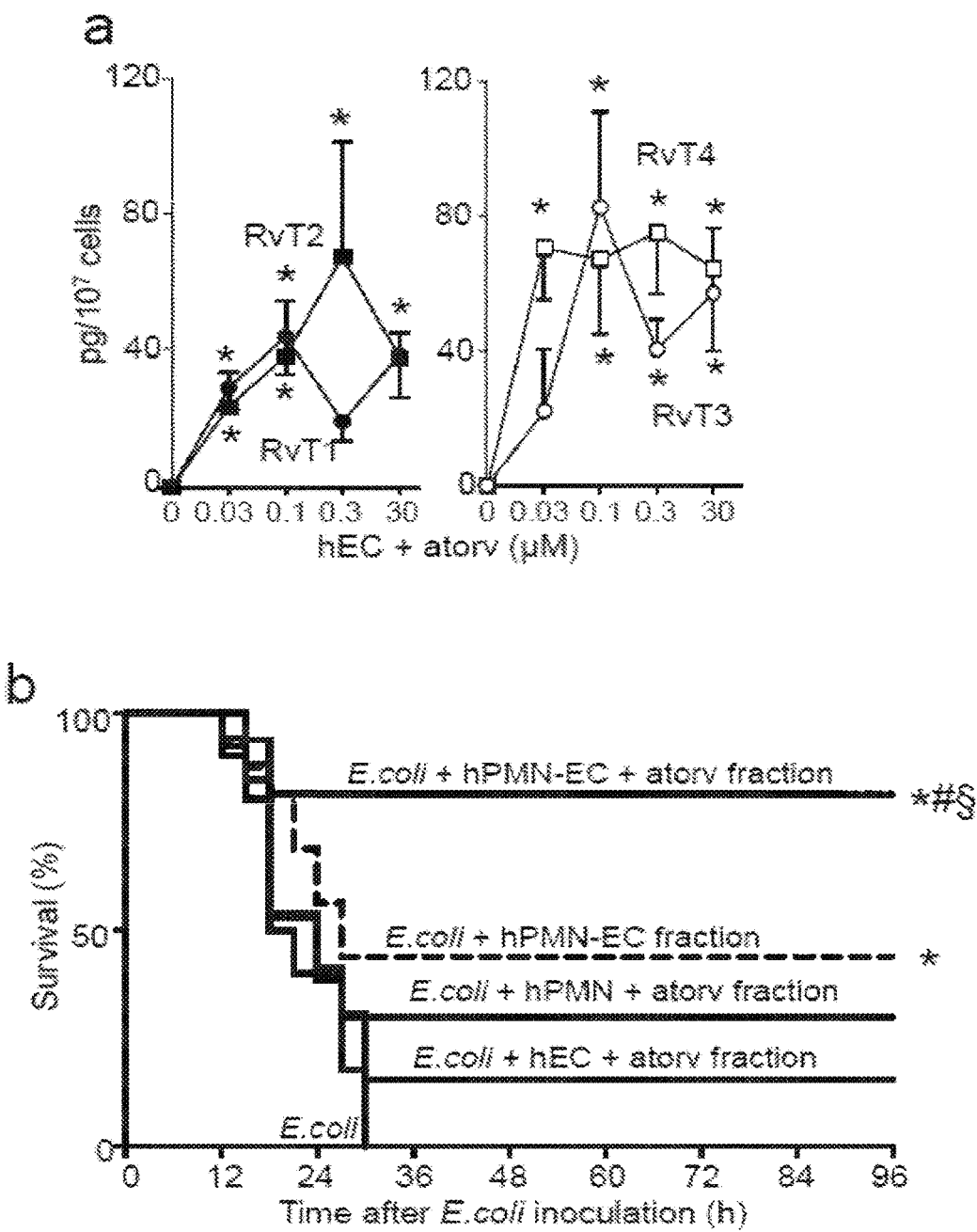
FIG. 8: Atorvastatin increases protective actions of neutrophil-endothelia cell fractions during mouse infections and promotes RvT formation via S-nitrosylated COX-2, (a) RvT in human neutrophil-endothelial cells co-incubations with or without atorvastatin. Mean±s.e.m.; n=4 independent cell preparations. Four independent experiments. *p<0.05 vs. EC group. (b) Fractions extracted using C18 SPE (see methods) were administered to mice (i.v.) 5 min prior to E. coli (2.5×10⁷ CFU/mouse) inoculation and survival assessed. n=14-17 mice/group. Three independent experiments. *p<0.05 vs. E. coli, #p<0.05 vs. E. coli plus hPMN-EC, § p<0.05 vs. E. coli plus hPMN plus atorv or E. coli plus hEC plus atorv. (c,d) Endothelial cells were incubated with IL-1β and TNF-α then vehicle, celecoxib and/or atorvastatin followed by n-3 DPA and hPMN. (c-d) Fractions were extracted (c) profiled using LM metabololipidomics. Mean±s.e.m. n=4 independent cell preparations/group. Three independent experiments. *p<0.05, **p<0.01 vs. incubations with IL-1β plus TNT-α alone #p<0.05 vs incubations with IL-1β plus TNF-α and atorvastatin. (d) administered prior to E. coli (2.5×10⁷ CFU/mouse) and survival assessed. n=1.0 mice/group. Two independent experiments. *p<0.05 vs. E. coli; #p<0.05 vs. E. coli plus hPMN-EC plus atorv. (e-f) Mice were inoculated with E. coli (1×10⁵ CFU/mouse), 1 h later L-NAME (24 mg/kg) or vehicle (saline) was administered followed by atorvastatin (5 µg/mouse, i.v., 5 h) or vehicle (saline plus 0.01% EtOH). (e) Plasma RvT were quantified using LM metabololipidomics, (f) exudate cell numbers were enumerated. Mean±s.e.m. n=4 mice/group. Two independent experiments. *p<0.05 vs. E. coli #p<0.05 vs. E. coli plus atorvastatin. (g) Conversion of n-3 DPA by human recombinant (hr) COX-2 and S-nitrosylated (SNO) hr-COX2. Mean±s.e.m. n=3 incubations. Three independent experiments.
Figure 8:
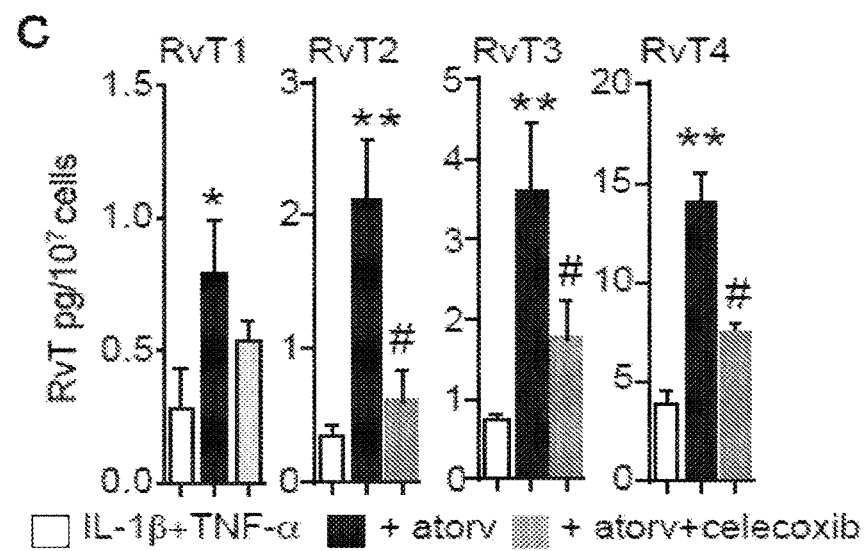
Figure 8:
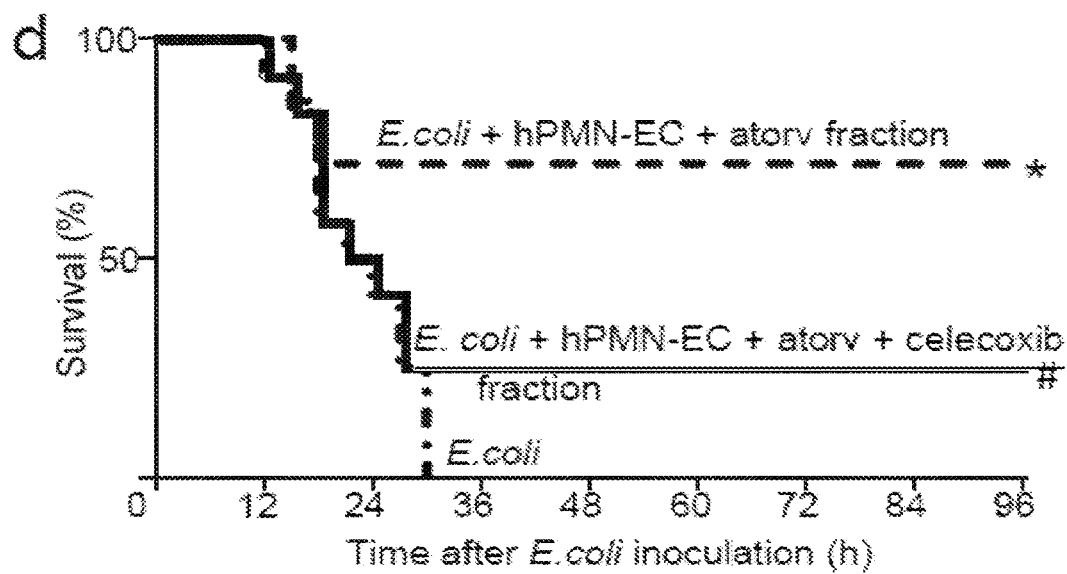
Figure 8:
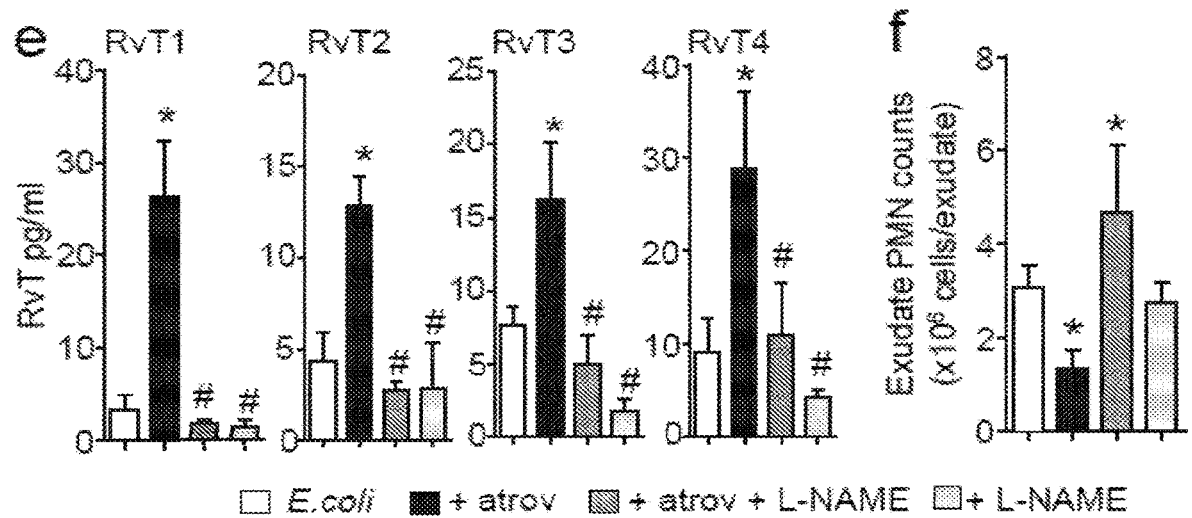
Figure 8:
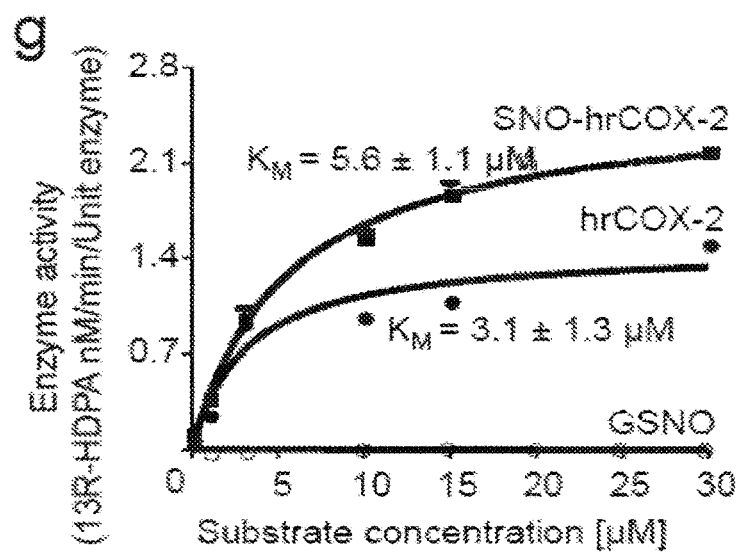

Atorvastatin is protective in bacterial infections in mice[15] and regulates COX-2[16]. Hence it was next questioned whether this statin regulates RvT biosynthesis. Incubation of neutrophil-endothelial cell co-cultures with atorvastatin, at concentrations (0.03-30 μM) relevant to those reached in humans[17], led to dose-dependent increases in RvT (FIG. 8a and Table 5). Fractions from these co-incubations significantly increased survival in mice during *E. coli* infections when compared to fractions from neutrophil-endothelial cell co-cultures without atorvastatin (FIG. 2b; p<0.05) and those from either neutrophil or endothelial cells incubated separately with atorvastatin (FIG. 8b). Celecoxib significantly reduced RvT in these incubations (FIG. 8c; p<0.05) and abolished the protective actions of isolated fractions obtained from neutrophil-endothelial cell co-incubations with atorvastatin (FIG. 8c).

TABLE 5

Supplementary Table 5: Lipid mediator levels in human endothelial cell incubations and neutrophil-endothelial cell co-incubations.

| | Endothelial cells | Neutrophil-endothelial cells | Neutrophil-endothelial cells plus Atorvastatin |
|---|---|---|---|
| DHA Bioactive Metabolome | | | |
| RvD1 | 2.5 ± 1.7 | 1.8 ± 1.8 | 0.3 ± 0.1 |
| RvD2 | 6.4 ± 0.9 | 4.3 ± 0.9 | 6.4 ± 1.9 |
| RvD3 | 11.8 ± 2.8 | 7.5 ± 1.2 | 8.9 ± 3.2 |
| RvD5 | 11.3 ± 1.4 | 10.7 ± 1.7 | 8.2 ± 1.4 |
| RvD6 | 84.5 ± 14.7 | 108.2 ± 29.7 | 122.8 ± 16.0 |
| MaR1 | 7.1 ± 2.2 | 4.8 ± 1.6 | 6.8 ± 2.0 |
| PD1 | 0.7 ± 0.5 | 0.2 ± 0.1 | 0.2 ± 0.0 |
| n-3 DPA | | | |

TABLE 5-continued

Supplementary Table 5: Lipid mediator levels in human endothelial cell incubations and neutrophil-endothelial cell co-incubations.

|  | Endothelial cells | Neutrophil-endothelial cells | Neutrophil-endothelial cells plus Atorvastatin |
|---|---|---|---|
| Bioactive Metabolome |  |  |  |
| RvT1 | 1.7 ± 0.5 | 8.4 ± 1.0 | 13.4 ± 0.9 |
| RvT2 | 1.3 ± 0.8 | 3.2 ± 1.6 | 17.7 ± 3.0 |
| RvT3 | 2.5 ± 0.8 | 8.8 ± 1.8 | 15.9 ± 4.2 |
| RvT4 | 3.0 ± 0.3 | 11.3 ± 1.7 | 13.7 ± 1.3 |
| EPA Bioactive Metabolome |  |  |  |
| RvE1 | 0.0 ± 0.0 | 0.5 ± 0.4 | 2.0 ± 1.5 |
| RvE2 | 42.0 ± 24.2 | 32.7 ± 8.6 | 71.7 ± 20.8 |
| RvE3 | 18.1 ± 1.8 | 27.5 ± 9.1 | 25.4 ± 6.3 |
| AA Bioactive Metabolome |  |  |  |
| LXA$_4$ | 33.1 ± 6.1 | 26.8 ± 5.8 | 21.0 ± 2.8 |
| LXB$_4$ | 4.5 ± 2.6 | 13.5 ± 9.1 | 10.1 ± 7.0 |
| 5,15-diHETE | 17.8 ± 3.5 | 20.8 ± 4.1 | 21.2 ± 1.5 |
| LTB$_4$ | 0.4 ± 0.2 | 50.8 ± 9.9 | 63.8 ± 11.3 |
| PGD$_2$ | 35.1 ± 8.2 | 132.1 ± 30.5 | 120.0 ± 40.4 |
| PGE$_2$ | 46.7 ± 6.8 | 481.0 ± 114.6 | 414.0 ± 193.5 |
| PGF$_{2\alpha}$ | 790.7 ± 152.0 | 1115.4 ± 76.6 | 1064.2 ± 168.8 |
| 8-iso-PGF$_{2\alpha}$ | 13.3 ± 4.0 | 22.0 ± 1.3 | 21.9 ± 10.8 |
| TxB$_2$ | 367.5 ± 82.7 | 1680.8 ± 252.2 | 1367.0 ± 420.1 |
| 12-HHT | 102.0 ± 21 | 819.0 ± 318.9 | 1005.3 ± 459.2 |

Human endothelial cells were incubated with IL1β and TNF-α (10 ng/ml each, 16 h, 37° C.), then vehicle (PBS containing 0.01% EtOH) or atorvastatin (Atorv; 30 min), for 30 min followed by n-3 DPA (1 μM, 15 min, 37° C.) and human neutrophils (1 × 10$^7$ cells/ml, 60 min, 37° C.) or PBS. Products were profiled using LM metabololipidomics and quantified using MRM monitoring of the parent ion in Q1 and a characteristic fragment ion in Q3. Results are mean ± s.e.m.
n = 4 independent cell preparations per group from four independent experiments.
Numbers denoted in bold are p < 0.05 vs. endothelial cell incubations alone.

Figure 9:
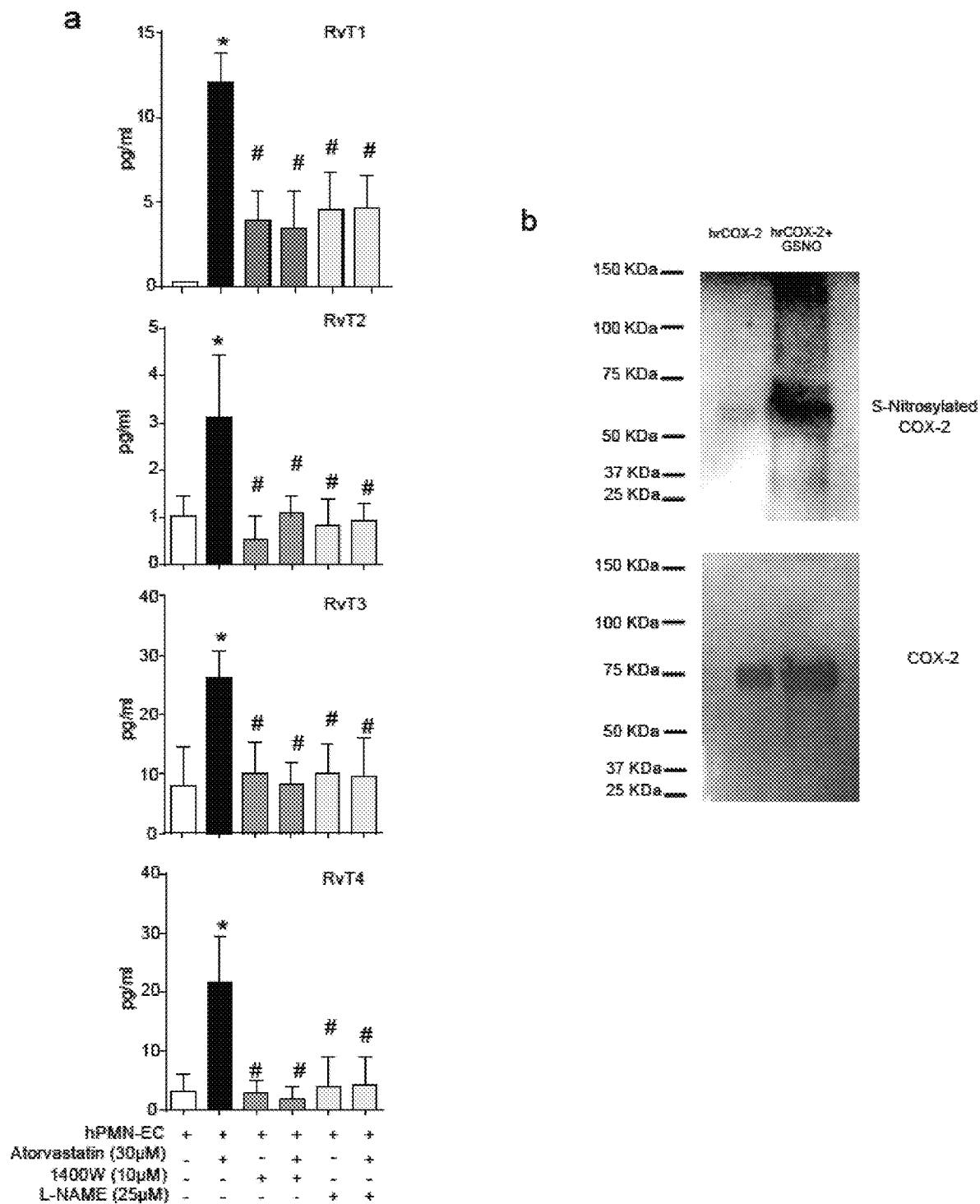
FIG. 9: Inhibition of nitric oxide synthase reverts atorvastatin mediated increases in RvT. (a) Human (h) endothelial cells (EC) were incubated with IL-1β and TNF-α (10 ng/ml each, 16 h, 37° C.), vehicle (PBS containing 0.01% DMSO), L89 NAME (25 µM) or 1400 W (10 µM, 25 min, 37° C.). Atorvastatin (atorv; 30 µM, 30 min), n-3 DPA (1 µM, 15 min, 37° C.) and PMN (1×107 cells/ml, 60 min, 37° C.) were then added, fractions were isolated and profiled using LM metabololipidomics. Results are mean±s.e.m. n=4 independent incubations from four independent experiments. *p<0.05, vs. hPMN-EC incubations. #p<0.05 vs hPMN-EC plus atorvastatin incubations. (b) Human recombinant COX-2 was incubated without (COX-2) or with S95 nitrosoglutathione (COX-2+GSNO) prepared as detailed in the methods section for 30 min (Room Temperature). S-nitrosylation was then assessed using Western blotting (see methods for details). Results are representative of n=6 incubations and three independent experiments.

Administration of L-NG-Nitroarginine Methyl Ester (L-NAME) prior to atorvastatin significantly reversed atorvastatin-mediated increases in plasma RvT (FIG. 8e; p<0.05) and increased neutrophil recruitment to the peritoneum during mouse infections (FIG. 8f). With human endothelial cells NOS inhibitors (L-NAME and 1400 W) also significantly reduced atorvastatin-mediated RvT increases by 70-90% (FIG. 9a; p<0.05). In addition, incubation of human recombinant COX-2 (hrCOX-2) with S-nitrosoglutathione, which S-nitrosylates COX-2[18] (FIG. 9b), gave increased 13R-HDPA and hrCOX-2 catalytic activity (FIG. 8g) compared to native COX-2. These results indicated that atorvastatin increased RvT production via S-nitrosylation of endothelial COX-2.

Figure 10:
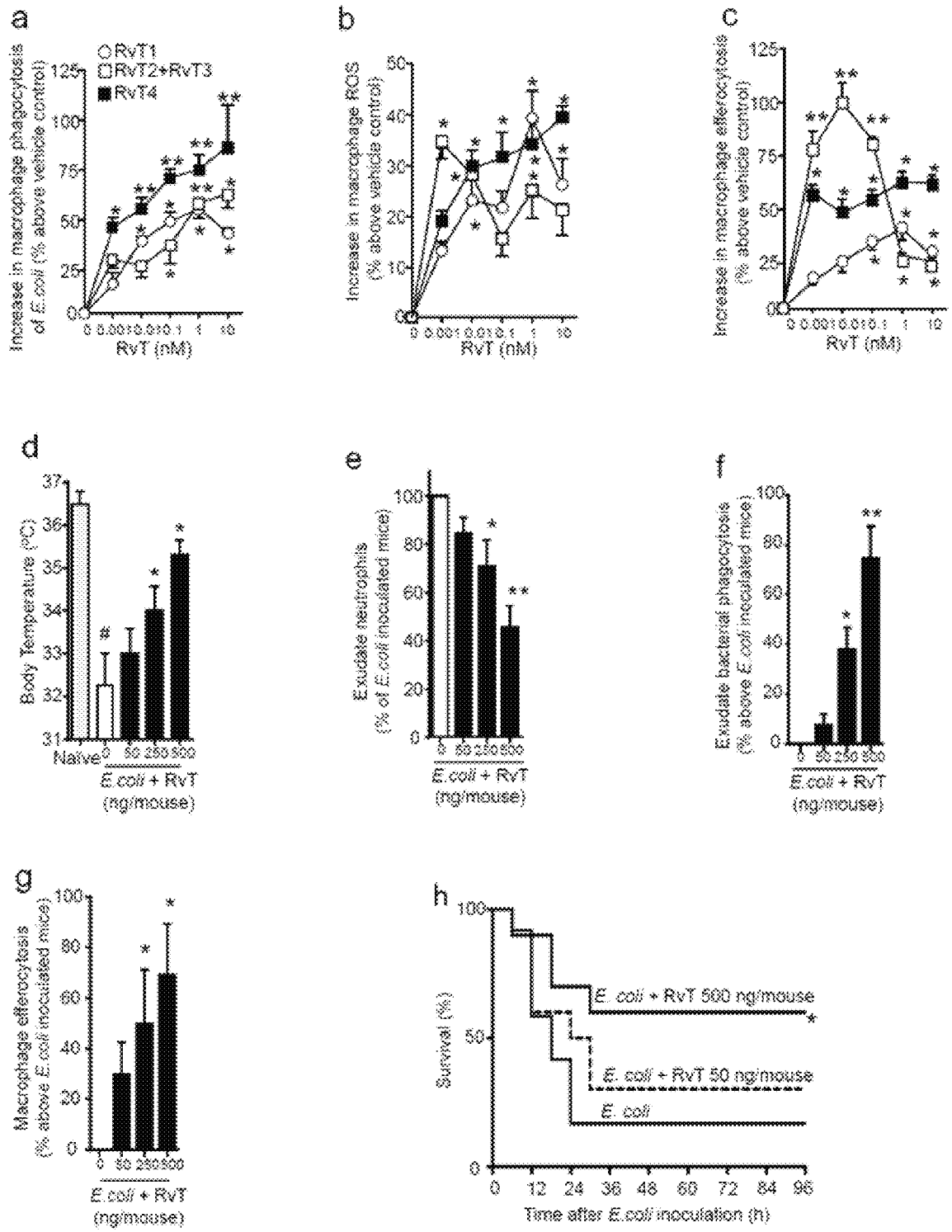
FIG. 10: RvT regulate leukocyte responses and promote survival in infections. (a) Macrophages (5×10⁴ cells/well) were incubated with the indicated concentrations of RvT1, RvT2 plus RvT3 (1:1 ratio), RvT4 or vehicle (PBS containing 0.01% EtOH; 15 min, 37° C., pH 7.45) then fluorescently labeled $E.\ coli$ ($2.5 \times 10^6$ CFU/well). (b) Macrophages ($5 \times 10^4$ cells/well) were incubated with $H_2$DCFDA (5 µM, 30 min, 37° C., pH 7.45); cells were washed, incubated with the indicated concentrations of RvT1, RvT2 plus RvT3 (1:1 ratio), RvT4 or vehicle (15 min, 37° C., pH 7.45), $E.\ coli$ ($2.5 \times 10^6$ CFU/well) were added and intracellular ROS levels determined. (c) Macrophages ($5 \times 10^4$ cells/well) were incubated as in (a) with RvT, fluorescently-labeled apoptotic PMN ($2.5 \times 10^5$ cells/well) were added and uptake assessed (see methods). Mean±s.e.m. n=4 donors. Three independent experiments. $*p<0.05$, $**p<0.01$ vs. macrophages plus vehicle. (d-g) Mice were given vehicle (saline containing 0.1% EtOH) or combination of RvT1, RvT2, RvT3 and RvT4 (ratio 2:1:1:8), each isolated and quantified by RP-UV-HPLC (see methods), via i.p. injection ~5 min prior to $E.\ coli$ ($1 \times 10$ CFU/mouse) inoculation. 12 h later (d) body temperatures, (e) peritoneal exudate neutrophil counts, (f) bacterial phagocytosis by peritoneal leukocytes (% $E.\ coli^+$ of total $CD11b^+$ population), (g) Macrophage efferocytosis in peritoneal exudates were assessed. Mean±s.e.m. n=5 mice/group. Two independent experiments. $*p<0.05$, $**p<0.01$ vs. $E.\ coli$ mice, #p<0.05 vs. naive mice. (h) Mice were inoculated with $E.\ coli$ ($2.5 \times 10^7$ CFU/mouse); 2 h later vehicle (saline+0.1% EtOH) or RvT (as in d-g; 50 ng/mouse or 500 ng/mouse) were administered via i.p. injection and survival assessed. n=10 mice per group. Two independent experiments $*p<0.05$ vs. $E.\ coli$ mice.
Figure 11:
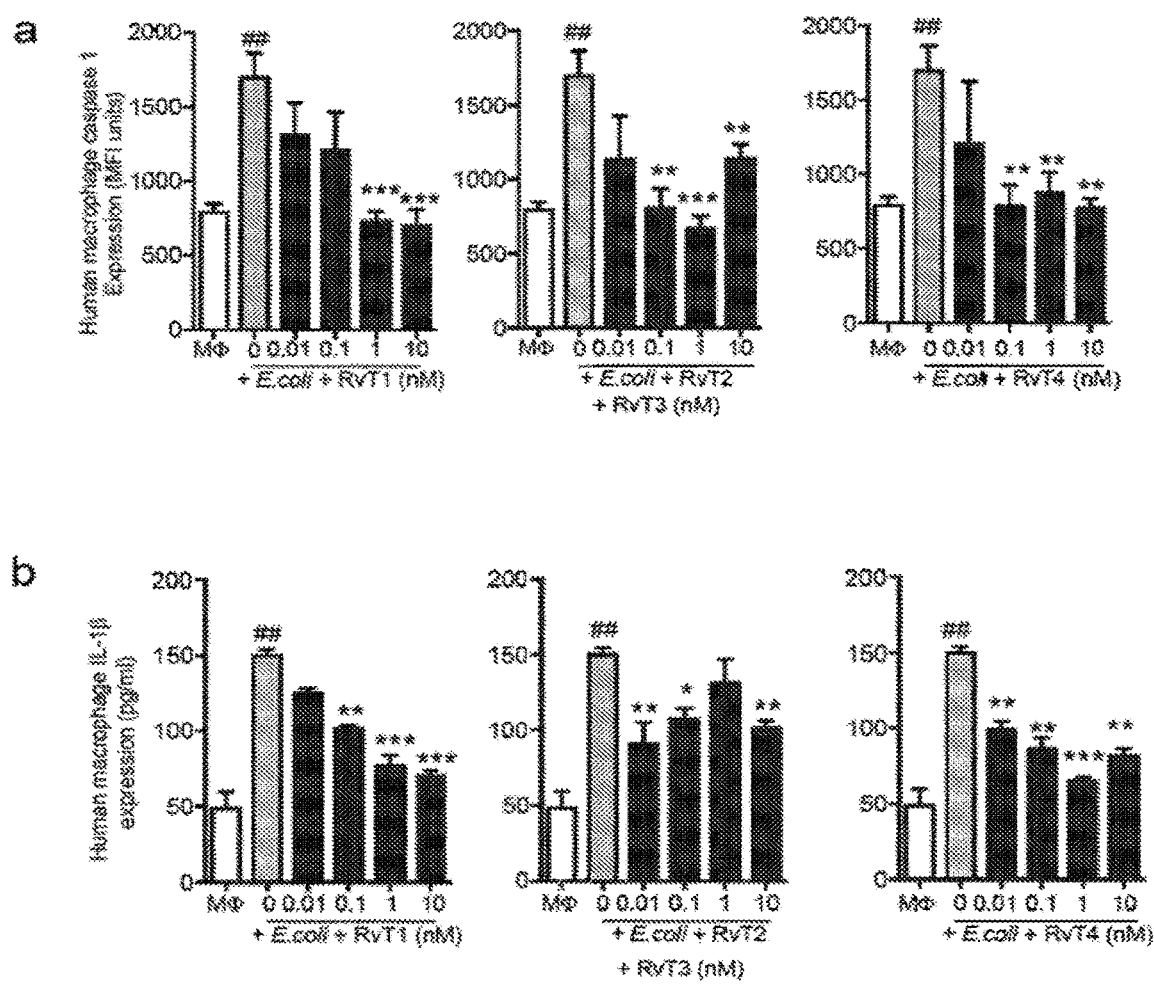
FIG. 11: RvT regulate inflammasome components in human macrophages and mice during $E.\ coli$ infections. Macrophages (Mφ; $1.5 \times 10^5$ cells/well) were incubated with the indicated concentrations of RvT1, RvT2 plus RvT3 (1:1 ratio), RvT4 or vehicle (PBS containing 0.01% EtOH; 15 min, 37° C., pH 7.45), $E.\ coli$ were added ($1.5 \times 10^7$ CFU/well, 16 h, 37° C. pH 7.45) and (a) caspase 1 levels assessed by flow cytometry; (b) IL-1β levels and (c) LDH activity were measured in the supernatants. Results are expressed as mean±s.e.m. n=4 donors from three independent experiments. $*p<0.05$, $p<0.01$, $*<0.001$ vs. macrophages plus $E.\ coli$, ##p<0.01 vs. macrophages alone. Mice were given vehicle (saline containing 0.1% EtOH) or a combination of RvT1, RvT2, RvT3 and RvT4 (at a ratio of 2:1:1:8), which were each isolated and quantified by RP-UV-HPLC (see methods for details) via i.p. injection 2 h post. $E.\ coli$ ($1 \times 10^7$ CFU/mouse) inoculation; 12 h later (d) exudate monocyte/macrophage caspase 1 expression, (e) exudate IL-1β levels, (f) exudate lactate dehydrogenase activity and (g) peripheral blood leukocyte-platelet aggregates were determined. Results are mean±s.e.m. n=5 mice per group from two independent experiments. $*p<0.05$, $**p<0.01$ vs. $E.\ coli$ mice.
Figure 11:
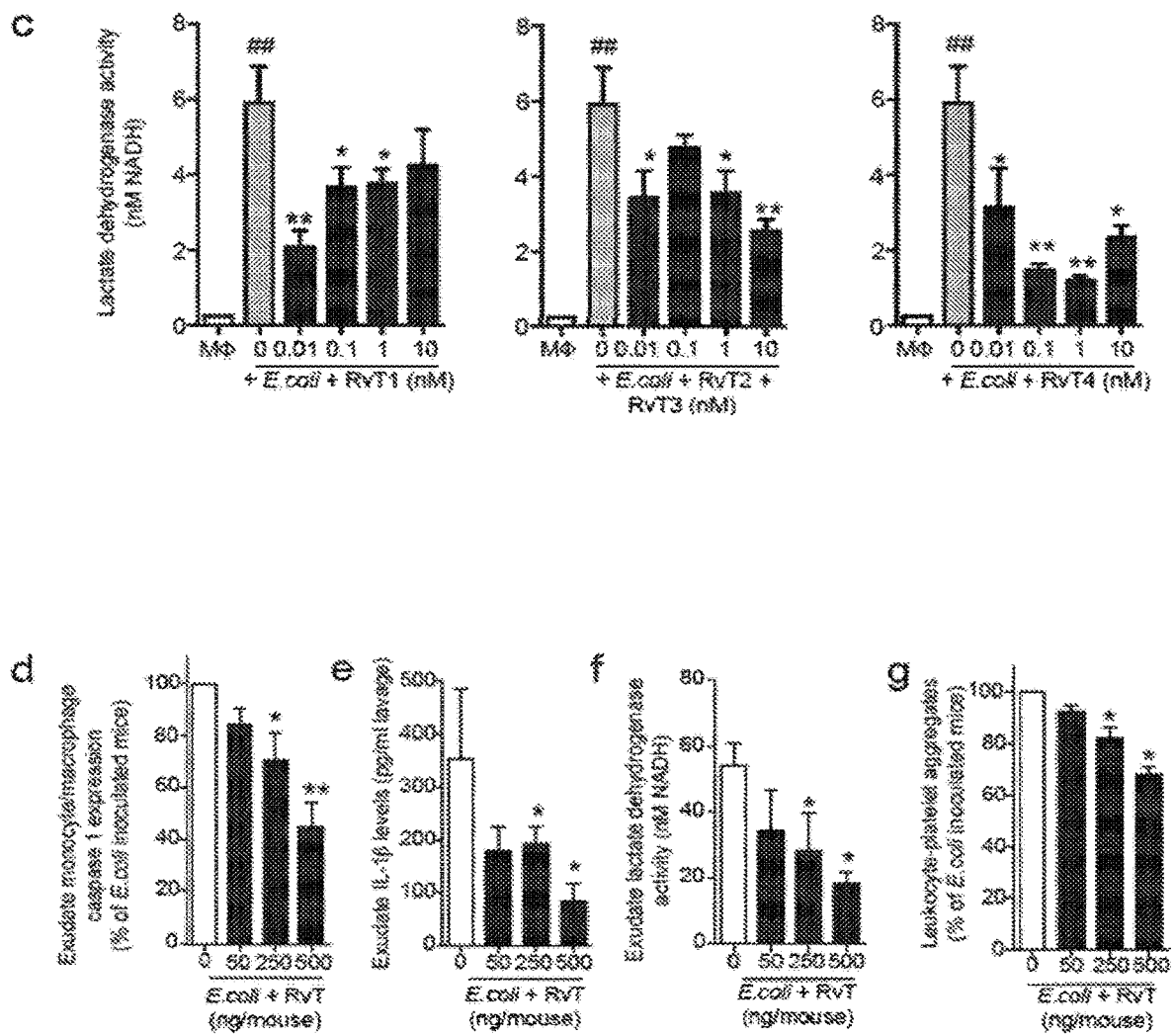

Next, the bioactions of these molecules were tested with human leukocytes. RvT were produced using recombinant enzymes and primary human neutrophils and isolated (see methods for details) using reverse phase high-pressure liquid chromatography (RP-HPLC). RvT1 and RvT4 were isolated to apparent homogeneity based on their appearance beneath a single RP-HPLC peak and characteristic UV chromophores. RvT2 and RvT3 were tested together since they eluted in the same RP-HPLC fractions. RvT1 (1 pM-10 nM) dose-dependently increased $E.$ $coli$ phagocytosis and production of intracellular reactive oxygen species (ROS) in human macrophages (FIG. 10a,b) as well as efferocytosis of apoptotic neutrophils (FIG. 10c), a key step in the resolution of inflammation[4]. Similar actions were obtained with human neutrophils, where RvT1 (1 pM-1.0 nM) dose-dependently increased $E.$ $coli$ phagocytosis (20-55%) and intracellular ROS (20-40%; n=4 donors). RvT1 (10 pM-10 nM) also dose-dependently blocked human macrophages activation of inflammasome components, decreasing caspase-1 and IL-1β expression and extracellular lactate dehydrogenase activity (LDH; FIG. 11a-c). Similar results were obtained with RvT4 and RvT2 plus RvT3 (FIG. 11a-c).

Figure 12:
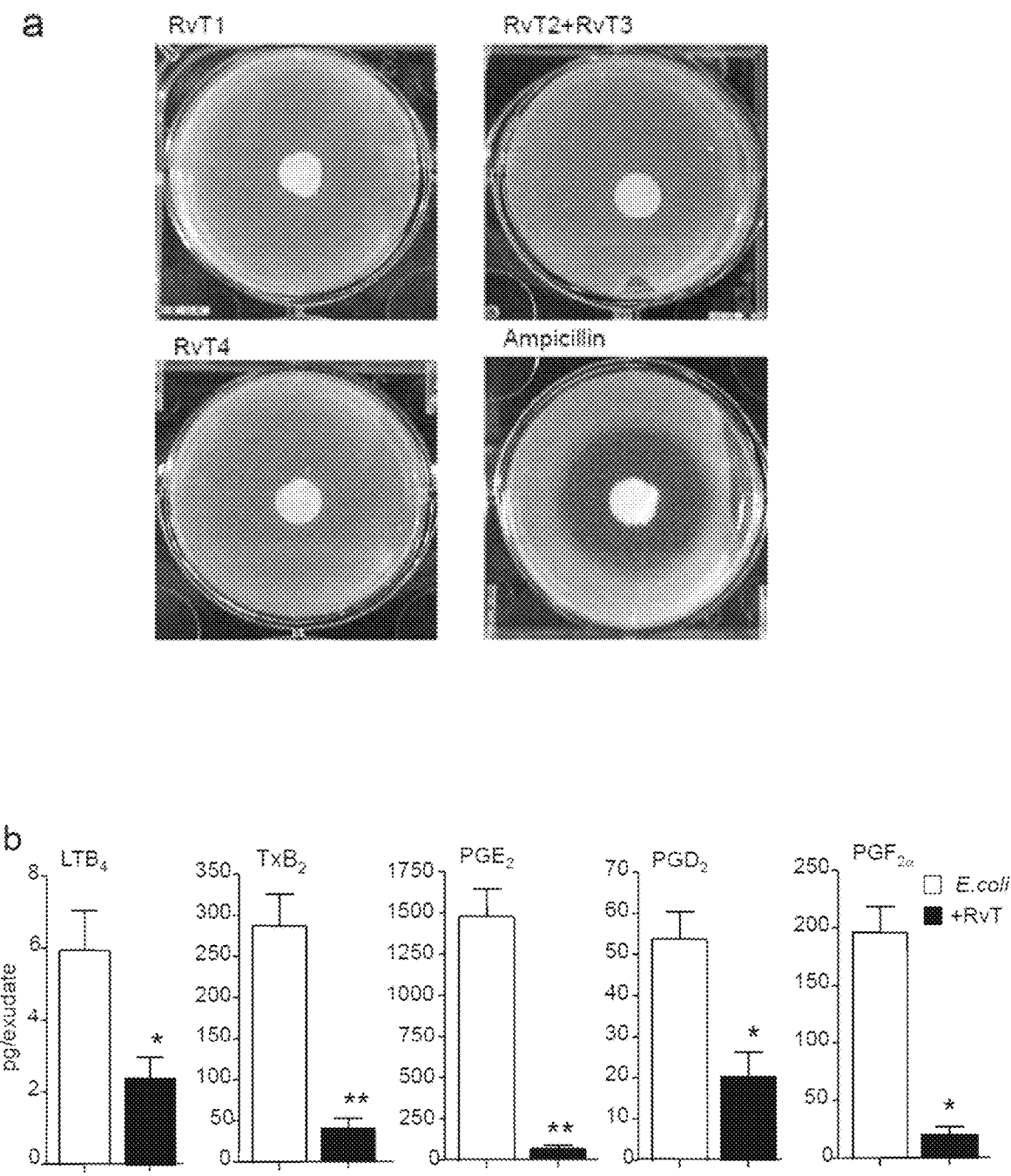
FIG. 12: RvT regulate exudate eicosanoids and do not display antibacterial actions at bioactive concentrations. (a) RvT were isolated and quantified using RP-UV-HPLC. RvT1, RvT2 plus RvT3, RvT4 (10 µM) or ampicillin (10 mM) were placed on LB agar plates containing $E.\ coli$ ($1 \times 10^7$ CFU). The zone of clearance was assessed after overnight incubation at 37° C. Results are representative of three independent experiments. (b) Mice were given a combination of RvT1, RvT2, RvT3 and RvT4 (RvT; 125 ng each/mouse; i.p.); each was isolated and quantified using RP-LV-HPLC (see methods for details), then combined in a mixture or vehicle (saline containing 0.1% EtOH) 5 min prior to $E.\ coli$ ($1 \times 10^7$ CFU/mouse) inoculation; 12 h later peritoneal exudates were collected and LM profiled using LM metabololipidomics. Results are mean±s.e.m. n=4 mice per group from two independent 127 experiments. $*p<0.05$; $**p<0.01$ vs. $E.\ coli$ mice.

Given RvT were each identified in human and murine infections, their combined actions were assessed in $E.$ $coli$ infections in mice, administering a mixture of RvT1, RvT2, RvT3 and RvT4 (RvT1-4) immediately prior to intraperitoneal $E.$ $coli$ inoculation. Twelve hours later these molecules afforded dose-dependent protection against hypothermia, limited further neutrophil recruitment to sites of inflammation, increased bacterial phagocytosis by peritoneal leukocytes (FIG. 10d-f), and reduced monocyte/macrophage expression of caspase-1, IL-1β levels and LDH activity (FIG. 11d-f) without exerting direct antibacterial activities (FIG. 11a). RvT also reduced systemic inflammation as demonstrated by reduced platelet-leukocyte aggregates[7] (FIG. 11g). LM metabololipidomics of plasma from mice given RvT1-4 (500 ng/mouse) gave significant reductions in TxB$_2$, PGD$_2$ and PGE$_2$ (FIG. 12b; p<0.05) that are elevated by inflammasome activation (i.e. eicosanoid storm) during infections[19]. RvT also significantly increased exudate macrophage efferocytosis (FIG. 10g; p<0.05). Moreover, administration of RvT1-4 2 h after $E.$ $coli$ inoculation dose-dependently increased mice survival (FIG. 10i).

Prolonged statin use is linked with a number of adverse effects including inflammasome activation[20], diabetes[21], as well as, nasopharyngitis, arthralgia, diarrhea, pain in the extremities, urinary tract infection, dyspepsia, nausea, musculoskeletal pain, muscle spasms, myalia, insomnia, and pharyngolaryngia pain[35]. Therefore it was next tested whether RvT could reduce the effective dose of atorvastatin needed to clear $E.$ $coli$ infections thus reducing statin exposure. Co-administration of RvT1-4, (~12.5 ng/mouse each), and a sub-threshold dose of atorvastatin (0.5 μs/mouse) immediately prior to $E.$ $coli$ inoculation significantly protected mice from hypothermia, reduced neutrophil recruitment (~50%; p<0.05), local and systemic bacterial loads, exudate IL-1β levels (~45%, p<0.05) and LDH activity (~40%; Supplementary FIG. 10a-e; p<0.05). This co-treatment also significantly increased bacterial phagocytosis by exudate leukocytes (~90%; p<0.05) and efferocytosis by exudate macrophages (~90%; FIG. 13f,g; p<0.05). Thus suggesting that RvT may reduce the exposure to atorvastatin therapy potentially limiting some of the unwanted side effects of statins observed at higher statin doses[20,21].

In order to assess whether this treatment regime was also protective in a therapeutic setting, mice were treated with atorvastatin (0.5 μg/mouse) and/or a mixture of RvT1-4 (50 ng/mouse) 2 h after $E.$ $coli$ inoculation. Co-administration of atorvastatin and RvT significantly reduced neutrophil recruitment to the peritoneum and reduced exudate bacterial loads (FIG. 13h; p<0.05). To gain insight into potential mechanism(s) activated by atorvastatin and RvT, expression of host protective[22,23] and pro-inflammatory factors[24] regulated by atorvastatin was investigated. In mice given 0.5 μg/mouse statin alone, increases were measured in host-protective PGI$_2$ and 15-deoxy-Δ-$^{12,14}$-PGJ$_2$, (FIG. 13i) whereas in endothelin-1 and plasminogen activator inhibitor-1 were reduced, molecules associated with a pro-inflammatory status (FIG. 13j). RvT administration (50 ng/mouse) regulated some of these molecules, although to a lesser extent (~30-60% lower) than atorvastatin. Co-administration of atorvastatin and RvT1-4 significantly reduced these molecules when compared to vehicle- or RvT-treated mice (FIG. 13j,k; p<0.05). Peripheral blood eicosanoids were also reduced upon RvT1-4 administration (FIG. 13k), effects that were only in part shared with atorvastatin.

Figure 4:
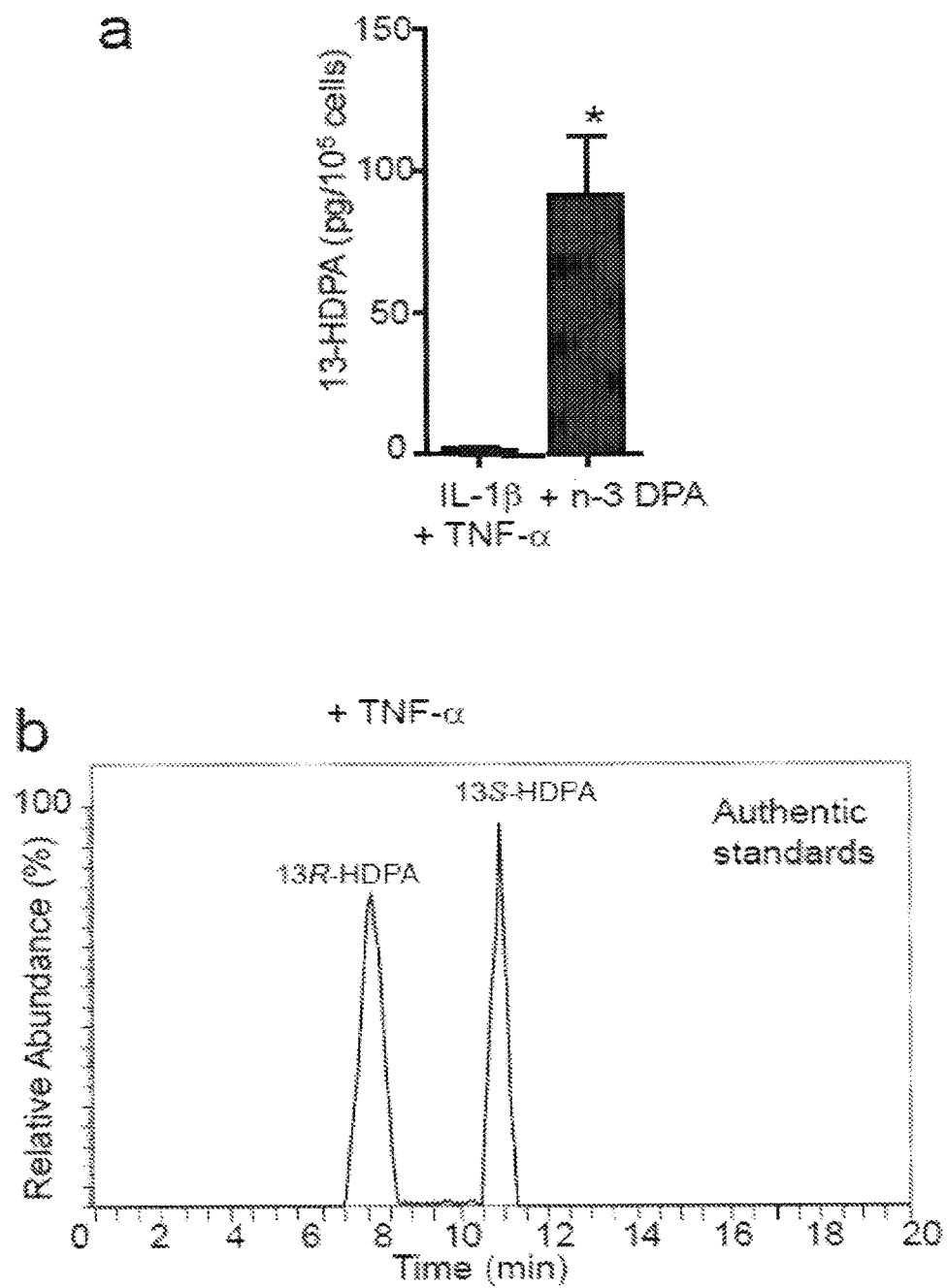
FIG. 4: Human COX-2 converts n-3DPA to 13R-HDPA in endothelial cells. (a) Human endothelial cells (hEC) were incubated with IL-1β and TNF-α (10 ng/ml each, 16 h, 37° C.) followed by vehicle (PBS containing 0.01% EtOH) or n-3 DPA (1 µM, 60 min, 37° C.) Fractions were extracted (see methods) and 13-HDPA was profiled using LM metabololipidomics. Results are mean±s.e.m. n=4 cell preparations from four independent experiments. *p<0.05 vs. hEC plus vehicle cells. (b) MRM chromatograms for standard 13R-HDPA and 13S-HDPA from chiral LC-MS-MS. (c,d) hEC were incubated as in (a) and 13-HDPA was assessed by chiral LM metabololipidomics. (c) MRM chromatogram for ion pair m/z 345>195 (d) MS-MS spectrum employed in the identification of 13R-HDPA. Results for (c,d) are representative of n=4 cell preparations from four independent experiments. (e) hEC were incubated with IL-1β and TNF-α (10 ng/ml each, 16 h, 37° C.) followed by vehicle (PBS containing 0.01% DMSO) or celecoxib (25 µM, 25 min, 37° C.); n-3 DPA (1 µM, 60 min, 37° C.) was then added, products extracted and 13-HDPA levels determined by LM metabololipidomics. (f) Endothelial cells were transfected with control scrambled (CS) or human COX-2 shRNA; cells were then incubated with IL-1β and TNT-α (10 ng/ml each, 16 h, 37° C.) and n-3 DPA (1 µM, 60 min, 37° C.). 13-HDPA levels were determined by LM metabololipidomics. Results for (e,f) are mean±s.e.m. n=4 cell preparations from four independent experiments. For (e) *p<0.05 vs. IL-1β plus TNF-α incubations alone. For (f) *p<0.05 vs. CS-shRNA plus IL-1β and TNF-α incubations. (g-h) Human recombinant (hr) COX-2 was incubated with n-3 DPA or AA (0.1 M Tris-HCl, pH8.0, 20 µM porcine hematin, 0.67 mM phenol, Room Temperature, 60 min) at the indicated concentrations and product formation was assessed (see methods) using (g) chiral LM metabololipidomics for hrCOX-2 products from n-3 DPA. (h) Michaelis Menten kinetics. Results for (g) are representative of n=6 incubations; (h) are mean±s.e.m. n=6 incubations from three independent experiments.
Figure 4:
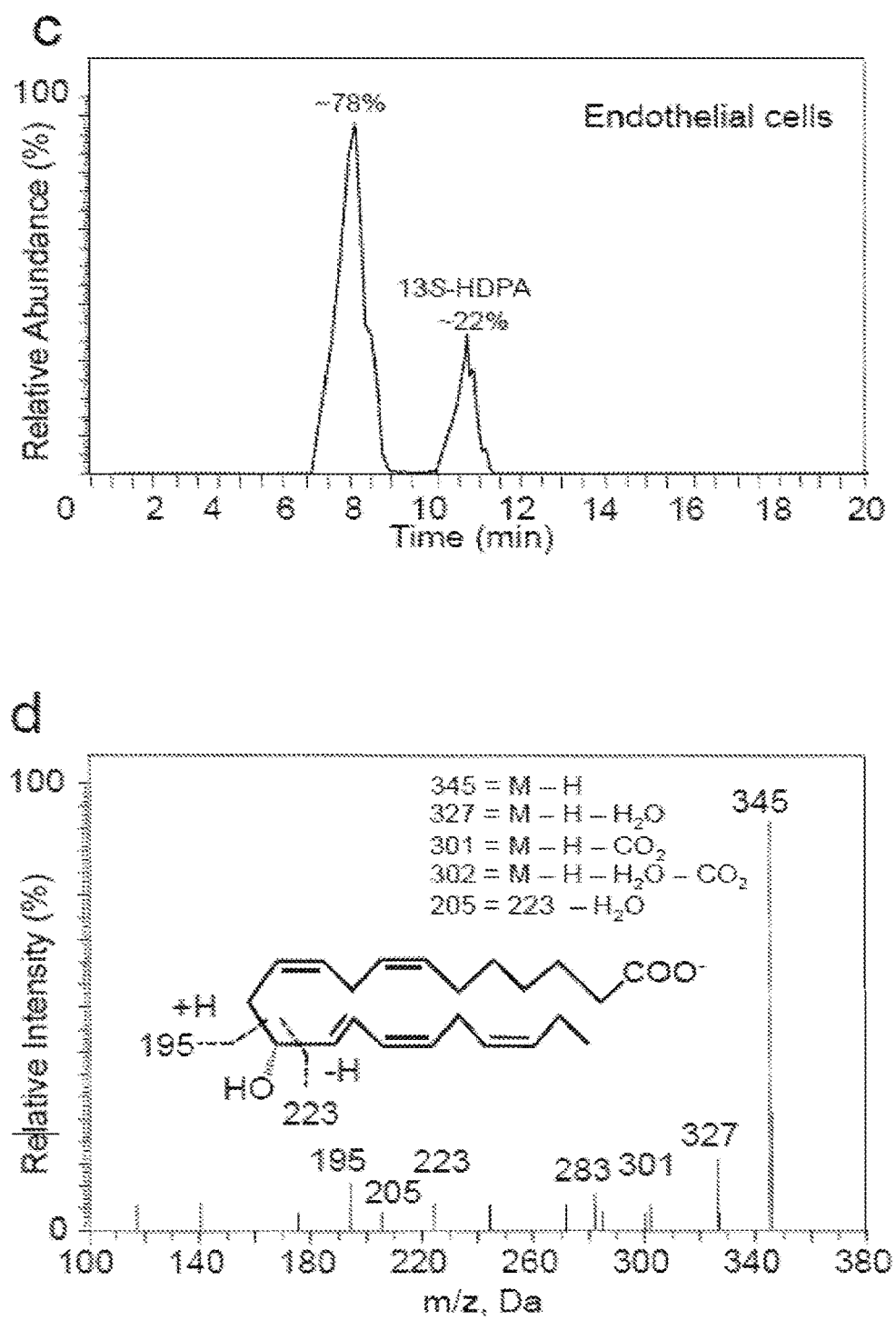
Figure 4:
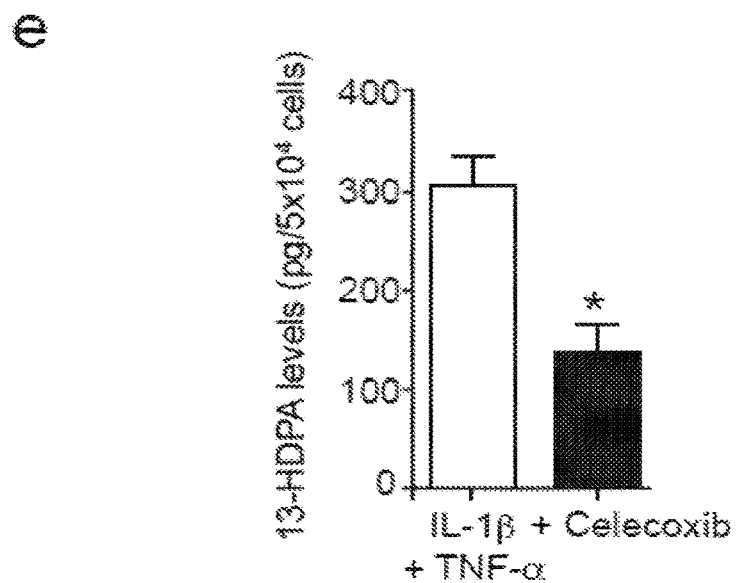
Figure 4:
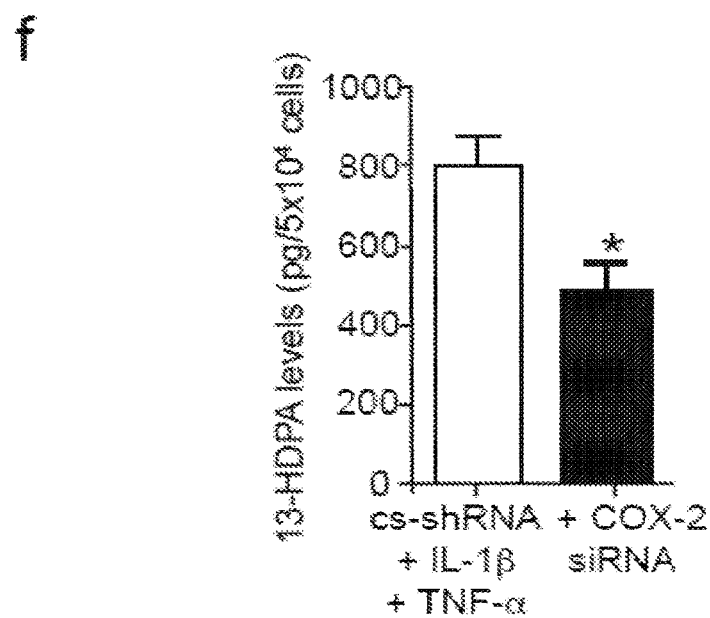
Figure 4:
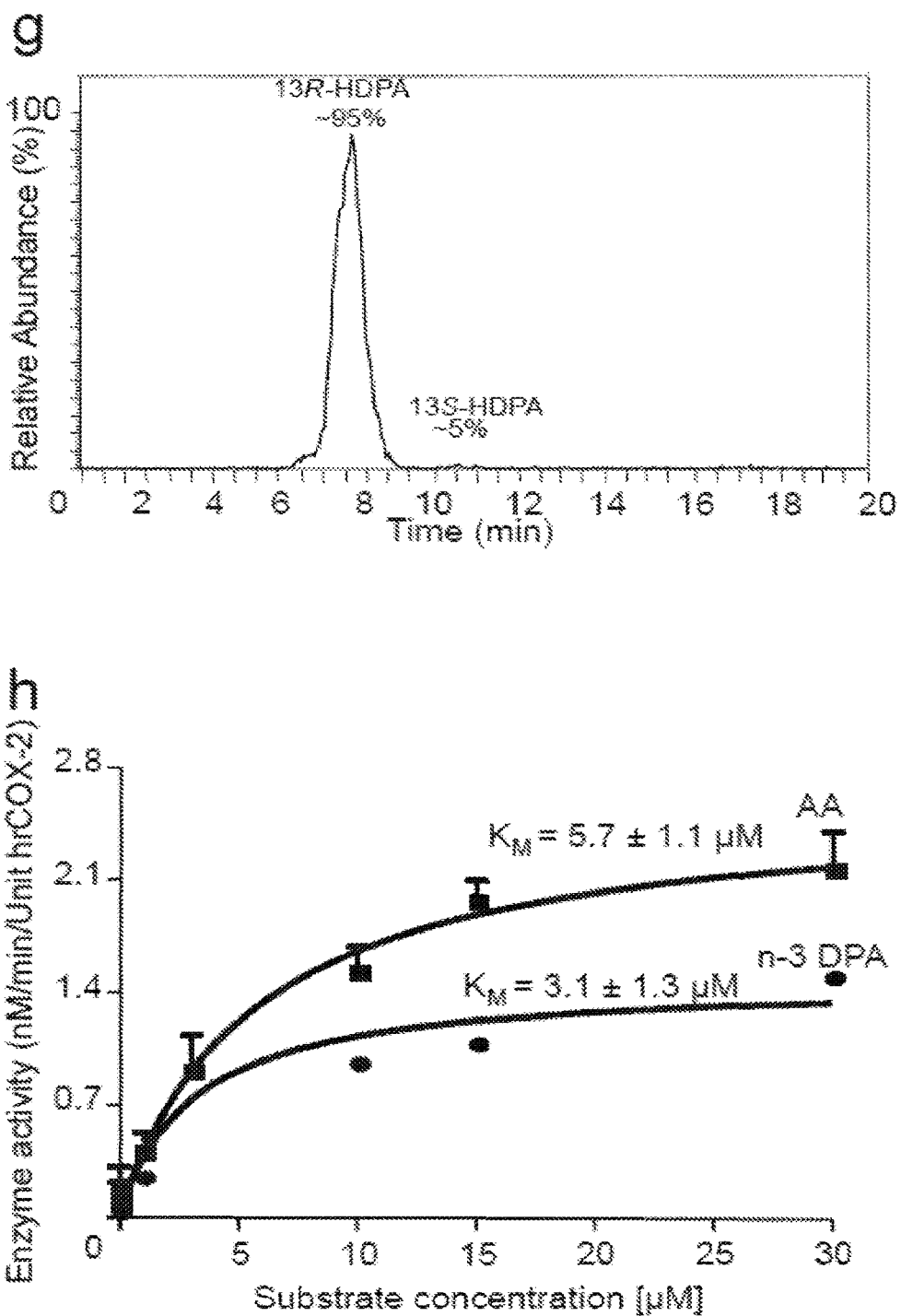
Figure 13:
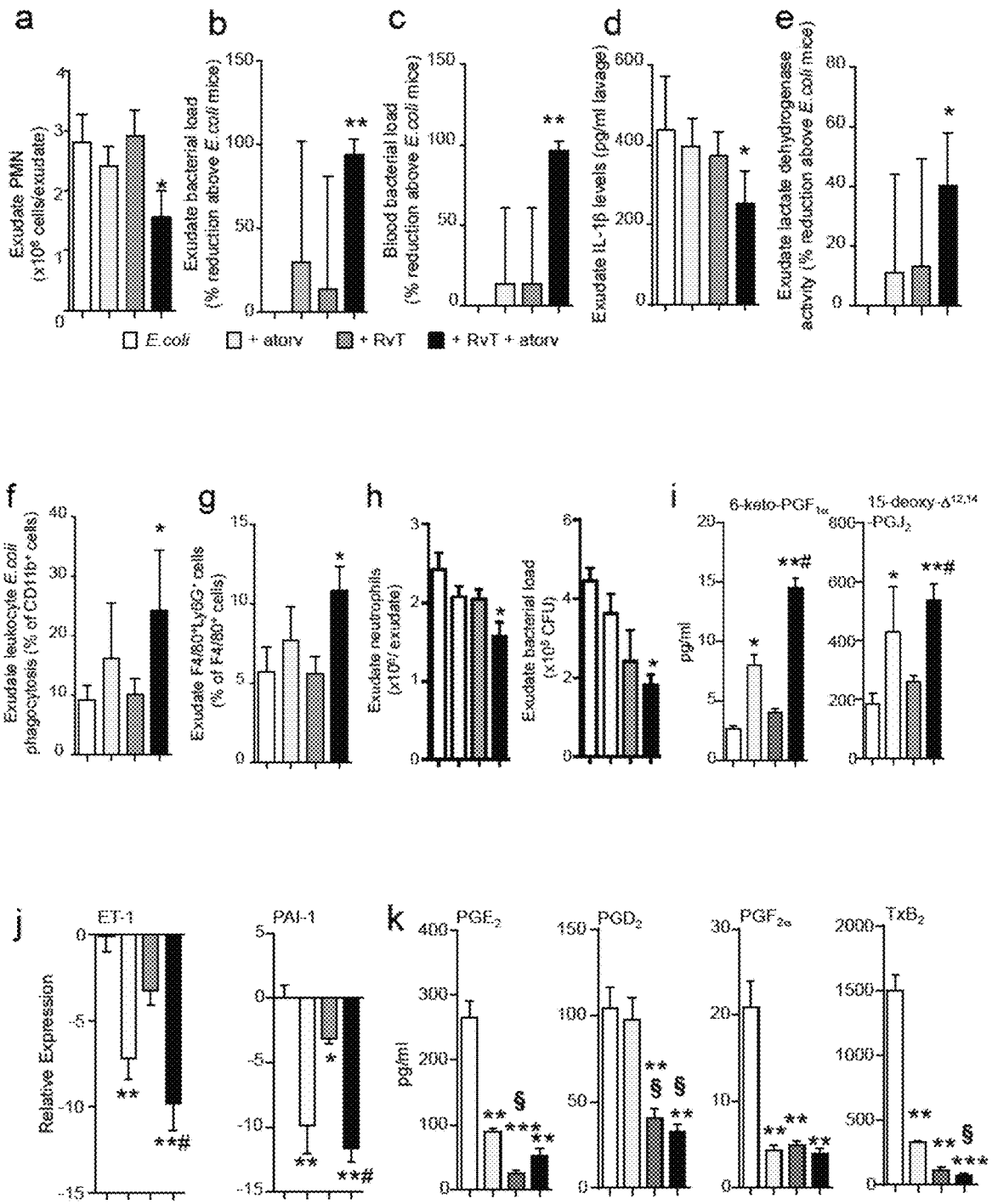
FIG. 13: Atorvastatin and RvT reduce local and systemic inflammation in murine infections. Mice were administered a combination of RvT1, RvT2, RvT3 and RvT4 (RvT~12.5 ng/mouse each); each was isolated and quantified using RP-UV-HPLC (see methods for details) and/or atorvastatin (atorv; 0.5 µg/mouse i.p.) or vehicle (saline containing 0.1% EtOH) 5 min prior to $E.\ coli$ inoculation ($1 \times 10^7$ CFU/mouse; i.p). Twelve hours later (a) peritoneal exudate neutrophil counts, (b) exudate bacterial loads, (c) peripheral blood bacterial loads, (d) exudate IL-1β levels, (e) exudate lactate dehydrogenase activity, (f) bacterial phagocytosis by peritoneal leukocytes, and (g) macrophage efferocytosisin peritoneal exudates were measured. Results are mean±s.e.m. n=4 mice per group, from two independent experiments. $*p<0.05$, $**p<0.01$ vs. $E.\ coli$ mice. (h-k) Mice were inoculated with $E.\ coli$ ($1 \times 10^7$ CFU/mouse; i.p.); 2 h later administered RvT1, RvT2, RvT3 and RvT4; each was isolated and quantified using RP-UV-HPLC (see methods for details), then combined in a mixture at a ratio of 2:1:1:8 (RvT; total 50 ng/mouse) and/or atorvastatin (atorv; 0.5 µg/mouse i.p.) or vehicle (saline containing 0.1% EtOH). (h) Twelve hours later, peritoneal exudate neutrophil counts (left panel) and exudate bacterial loads were measured (right panel). (i-k) Six hours after $E.\ coli$ administration (i, k), peripheral blood eicosanoid levels were measured using LC-MS-MS or ELISA; (j) Lung mRNA levels of endothelin (ET)-1 and plasminogen activator inhibitor (PAI) were measured using qRT-PCR. $*p<0.05$, $p<0.01$, $*p<0.001$ vs. $E.\ coli$ mice; #p<0.05 vs. $E.\ coli$ plus RvT mice; § p<0.05 vs. $E.\ coli$ plus atorvastatin mice. Results for a-e are mean±s.e.m. n=5 mice per group from two independent experiments.
Figure 14:
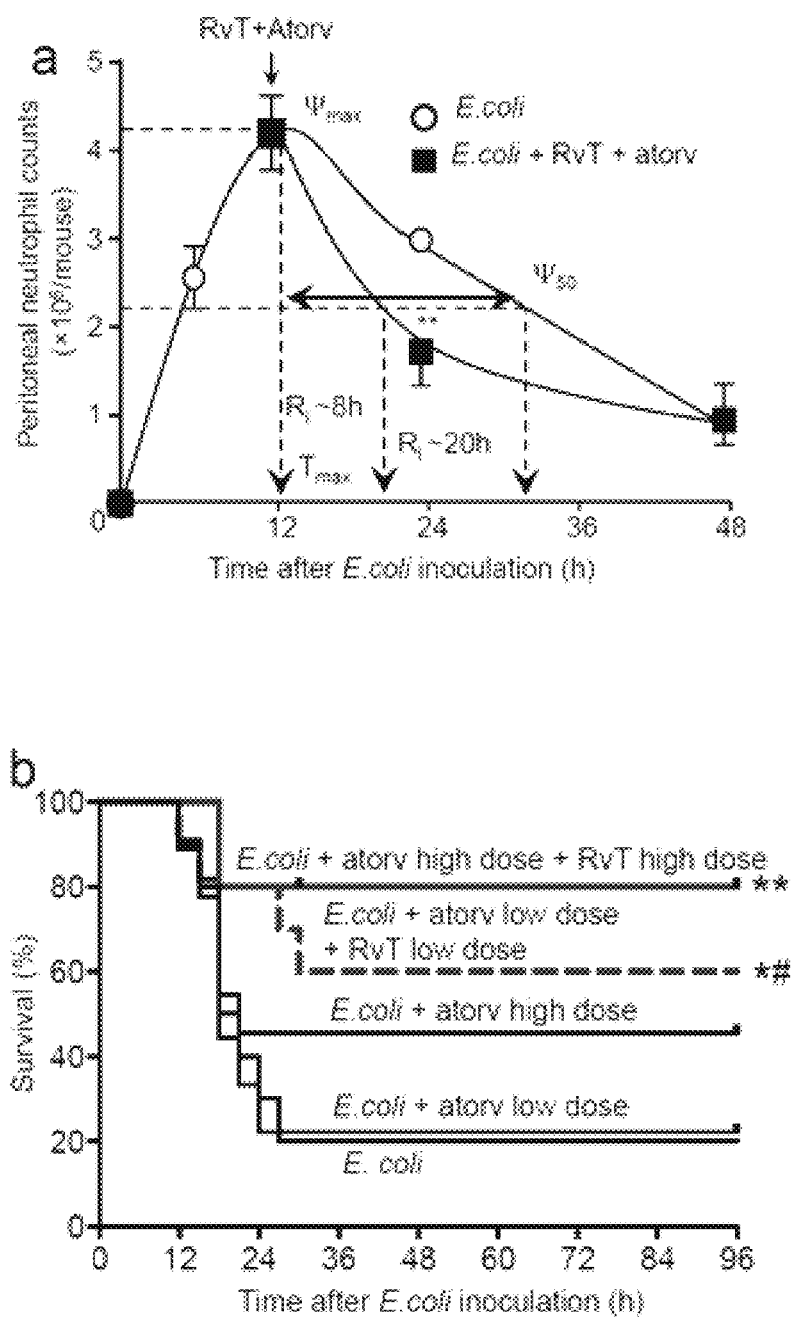
FIG. 14 (FIG. 4): Atorvastatin and RvT accelerate resolution of infections and promote survival in bacterial infections in mice. (a) Mice were inoculated with $E.\ coli$ ($1 \times 10^5$ CFU/mouse) plus RvT (combination of RvT1, RvT2, RvT3 and RvT4, ratio of 1:1:1:1, isolated and quantified by RP-UV-HPLC, total 50 ng/mouse). Atorvastatin (0.5 µg/mouse; i.p.) or vehicle (saline containing 0.1% EtOH) was administered and exudate neutrophil counts ($CD11b^+$ $Ly6G^+$) assessed at the indicated time points using light microscopy and flow cytometry. Results are mean±s.e.m. n=4 mice per group from two independent experiments. $**p<0.01$ vs. 24 h vehicle group. (b) Mice were inoculated with $E.\ coli$ ($2.5 \times 10^7$ CFU/mouse); after 3 h administered vehicle (Saline+0.1% EtOH), 0.5 µg/mouse (atorv low dose), 5 µg/mouse (atorv high dose) atorvastatin, 0.5 µg/mouse atorvastatin plus 50 ng/mouse RvT (atorv low dose plus RvT low dose) or 5 µg/mouse atorvastatin plus 500 ng/mouse RvT (atorv high dose plus RvT high dose); each of the RvT was isolated as in panel (a) and survival assessed. n=10 mice per group from three independent experiments. $*p<0.05$, $**p<0.01$ vs. $E.\ coli$ mice. #p<0.05 vs. $E.\ coli$ plus atorv low dose mice.

Given these protective actions the inventors assessed whether co-administration of RvT and atorvastatin could accelerate resolution of infections. Administration of RvT1-4 (50 ng/mouse) together with atorvastatin (0.5 μg/mouse) at peak neutrophil infiltration (12 h) significantly accelerated exudate neutrophil clearance, increased bacterial phagocytosis by exudate leukocytes (~50%; p<0.05), accelerated resolution of inflammation, shortening the resolution interval from ~20 h to ~8 h (FIG. 14a and FIG. 13). Co-administration of RvT1-4 with atorvastatin at both high (500 ng RvT plus 5 μg atorvastatin) and low doses (50 ng RvT plus 0.5 μg atorvastatin) increased survival of mice compared to treatment with atorvastatin alone (FIG. 4b). Together these results suggest that during infections RvT lower the effective dose of atorvastatin.

In summary, using LC-MS-MS based lipid mediator-metabololipidomidics, the inventors elucidated the structures of four new bioactive molecules termed RvT formed by transcellular biosynthesis [4,9,14] during human neutrophil-endothelial cell interactions (Table 6 and FIG. 2b). RvT production was elevated during self-resolving inflammatory challenge in humans and mice, and down-regulated in mice during delayed resolution of infections. These 13-series resolvins from n-3 DPA exerted both anti-inflammatory and potent pro-resolving activities regulating host responses during E. coli infections in mice and phagocytosis by isolated human cells, thereby fulfilling criteria as immunoresolvents[4]: namely, they stimulate the cardinal signs of resolution including expurgatio reliquiorum (clearance of debris), expurgatio contagionem agentis (clearance of infective agents), doloris absentia (analgesia) and muneris lucrum (gain of function)[4]. Given the extensive size of the vascular-endothelial system in humans and the abundance of neutrophils within the circulation, RvT formation during early stages of self-resolving acute inflammation and their regulation by atorvastatin, could provide a molecular basis for the development of new treatment strategies for infectious-inflammation. In addition, RvT may also serve as statin-markers and mediators of their actions during resolution responses.

TABLE 6

Evidence for the structure, biosynthesis, and actions 13-series resolvins

| | Biological system identified | For structural elucidation | Biosynthesis | Bioactions | |
| --- | --- | --- | --- | --- | --- |
| | | | | In vivo | In vitro |
| RvT1 | Human healthy volunteer whole blood Human sepsis patient plasma Mouse plasma during E. coli infections Human neutrophil and endothelial cell co-incubations | Retention time in liquid chromatography 11.2 min UV chromophore $\lambda_{max}$#269 and 238 nm MS-MS spectrum of natural product m/z 377, 359, 341, 333, 319, 297, 239, 233, 215, 211, 193, 175, 143 MS-MS spectrum of methyl ester sodium adduct m/z 415, 397, 357, 277, 249, 233, 181 MS-MS spectrum of product containing $O^{18}$: mz 381, 363, 361, 343, 341, 319, 303, 301, 241, 223, 221, 217, 215, 213, 193, 145, 125, 115 | Addition of n-3 docosapentaenoic acid to neutrophil-endothelial co-incubations increased compound 1 levels COX-2 specific inhibitor and shRNA to human COX-2 reduced 13R-hydroxy-7Z,10Z,14,16Z,19Z-docosapentaenoic acid levels COX-2 specific inhibitor reduced compound 1 levels in human neutrophil-endothelial cell co-incubations $O^{18}$ incorporation | Protects against infection induced hypothermia* Limits neutrophil recruitment during infections* Stimulates murine leukocyte phagocytosis of E. coli* Stimulates macrophage efferocytosis of apoptotic neutrophils* Reduces exudate pro-inflammatory eicosanoid levels during infections* Reduces levels of inflammasome components* Reduces pyroptosis Elaborates the protective actions of atorvastatin in infections* Reduces circulating platelet-leukocyte aggregates* Downregulation of ET-1 and PAI-1 at lung tissue* | Stimulates human macrophage efferocytosis of apoptotic neutrophils Stimulates human macrophage and neutrophil phagocytosis of E. coli Stimulates human macrophage and neutrophil intra-phagolysosomal ROS production Reduces E. coli induced inflammasome components in human macrophages Reduces E. coli induced macrophage pyroptosis |
| RvT2 | Human healthy volunteer whole blood Human sepsis patient plasma Mouse plasma during E. coli infections Human neutrophil and endothelial cell co-incubations | Retention time in liquid chromatography 12.3 min UV chromophore $\lambda_{max}$#235 nm MS-MS spectrum m/z 377, 359, 341, 333, 315, 297, 233, 225, 207, 197, 181, 143 MS-MS spectrum of methyl ester sodium adduct m/z 415, 397, 293, 235, 233, 181, 153 MS-MS spectrum of product containing $O^{18}$: m/z 379, 361, 359, 319, 317, 257, 233, 229, 227, 219, 209, 207, 199, 179, 145, 125 | Addition of n-3 docosapentaenoic acid to neutrophil-endothelial co-incubations increased compound 1 levels COX-2 specific inhibitor and shRNA to human COX-2 reduced 13R-hydroxy-7Z,10Z,14,16Z,19Z-docosapentaenoic acid levels COX-2 specific inhibitor reduced compound 1 levels in human neutrophil-endothelial cell co-incubations | Protects against infection induced hypothermia* Limits neutrophil recruitment during infections* Stimulates murine leukocyte phagocytosis of E. coli* Stimulates macrophage efferocytosis of apoptotic neutrophils* Reduces exudate pro-inflammatory eicosanoid levels during infections* Reduces levels of inflammasome components* Reduces pyroptosis Elaborates the protective actions of atorvastatin in | Stimulates human macrophage efferocytosis of apoptotic neutrophils Stimulates human macrophage and neutrophil phagocytosis of E. coli Stimulates human macrophage and neutrophils intra-phagolysosomal ROS production Reduces E. coli induced inflammasome components in human macrophages |

TABLE 6-continued

Evidence for the structure, biosynthesis, and actions 13-series resolvins

| Biological system identified | For structural elucidation | Biosynthesis | Bioactions In vivo | Bioactions In vitro |
|---|---|---|---|---|
| | | Incubation of 13R-hydroxy-7Z,10Z,14Z,16Z,19Z-docosapentaenoic acid with neutrophils and acid methanol gave trapping products that were consistent with the formation of an epoxide intermediate $O^{18}$ incorporation | infections* Downregulation of ET-1 and PA1-1 in lung tissue Reduces circulating platelet-leukocyte aggregates* | Reduces *E. coli* induced macrophage pyroptosis |
| RvT3 Human healthy volunteer whole blood Human sepsis patient plasma Mouse plasma diaing *E. coli* infections Human neutrophil and endothelial cell co-incubations | Retention time in liquid chromatography 12.6 min UV chromophore ё$_{max\ \#}$ 238 nm MS-MS spectrum 377, 359, 341, 333, 315, 297, 255, 233, 207, 155, 143 MS-MS spectrum of methyl ester sodium adduct m/z 415, 397, 293, 265, 233, 211, 181 MS-MS Spectrum of product containing $O^{18}$: m/z 379, 361, 359, 341, 319, 317, 257, 239, 237, 233, 227, 219, 209, 207, 175, 145, 125, 115 | Addition of n-3 docosapentactroic acid to neutrophil-endothelial co-incubations increased compound 1 levels COX-2 specific inhibitor and shRNA to human COX-2 reduced 13R-hydroxy 7Z,10Z,14Z,16Z,19Z-docosapentaenoic acid levels COX-2 specific inhibitor reduced compound 1 levels in human neutrophil-endothelial cell co-incubations Incubation of 13R-hydroxy-7Z,10Z,14Z,16Z,19Z-docosapentaenoic acid with neutrophils and acid methanol gave trapping products that were consistent with the formation of an epoxide intermediate $O_{18}$ incorporation | Protects against infection induced hypothermia* Limits neutrophil rererecruitment recruitment during infections* Stimulates murine leukocyte Phagocytosis of *E. coli*\* Stimulates macrophage efferocytosisof apoptotic neutrophils* Reduces exudate pro-inflammatory eicosanoid levels during infections* Reduces levels of inflammasome components* Reduces pyroptosis Elaborates the protective actions of atorvastatin in infections* Reduces circulating platelet-leukocyte aggregates* Downregulation of ET-1 and PAI-1 in lung tissue | Stimulates human macrophage efferocytosis of apoptotic neutrophils Stimulates human macrophage and neutrophil phagocytosisof *E. coli* Stimulates human macrophage and neutrophil intra-phagolysosomal ROS production Reduces *E. coli* induced inflammasome components in human macrophages Reduces *E. coli* induced macrophage pyroptosis |
| RvT4 Human healthy volunteer whole blood Human sepsis patient plasma Mouse plasma during *E. coli* infections Human neutrophil and endothelial cell co-incubations | Retention time in liquid chromatography 14.1 min UV chromophore ё$_{max\ \#}$ 237 nm MS-MS spectrum m/z 361, 343, 325, 299, 221, 239, 217, 211, 199, 193, 143 MS-MS spectrum of methyl ester sodium adduct m/z 399, 381, 363, 249, 227, 199, 181 MS-MS spectrum of product containing $O^{18}$: m/z 363, 345, 343, 325, 303, 301 241, 233, 221, 217, 213, 203, 199, 193, 145, 125, 115 | Addition of n-3 docosapentanoic acid to neutrophil-endothelial co-incubations increased compound 1 levels COX-2 specific inhibitor and shRNA to human COX-2 reduced 13R-hydroxy-7Z,10Z,14Z,16Z,19Z-docosapentaenoic acid levels COX-2 specific inhibitor reduced compound 1 levels in human neutrophil-endothelial cell co-incubations $O_{18}$ incorporation | Protects against infection induced hypothermia* Limits neutrophil recruitment during infections* Stimulates murine leukocyte phagocytosisof *E. coli*\* Stimulates macrophage efferocytosisof apoptotic neutrophils* Reduces exudate pro-inflammatory eicosanoid levels during infections* Reduces levels of inflammasome components* Reduces pyroptosis Elaborates the protective actions of atorvastatin in infections* Reduces circulating platelet-leukocyte aggregates* Downregulation of ET-1 and PA1-1 in lung tissue* | Stimulates human macrophage efferocytosis of apoptotic neutrophils Stimulates human macrophage and neutrophil phagocytosis of *E. coli* Stimulates human macrophage and neutrophil intra-phagolysosomal ROS production Reduces *E. coli* induced inflammasome components in human macrophages Reduces *E. coli* induced macrophage pyroptosis |

All publications and patents specifically mentioned herein are incorporated by reference for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 through 15 provide for various additional aspects of the present invention. In one embodiment, in a first paragraph:

1. A compound having the formula:

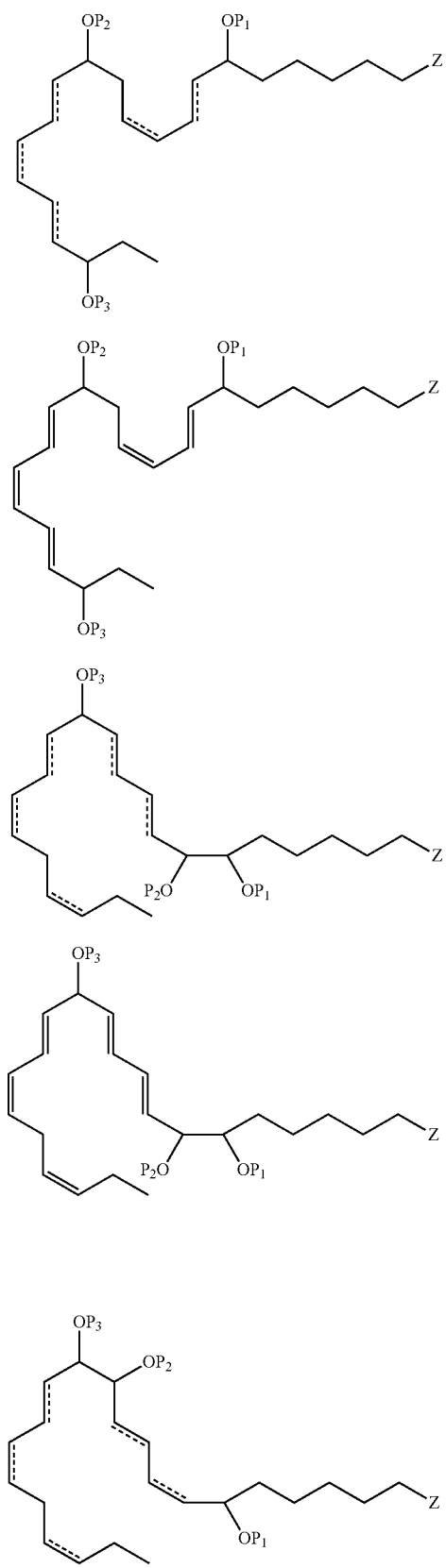

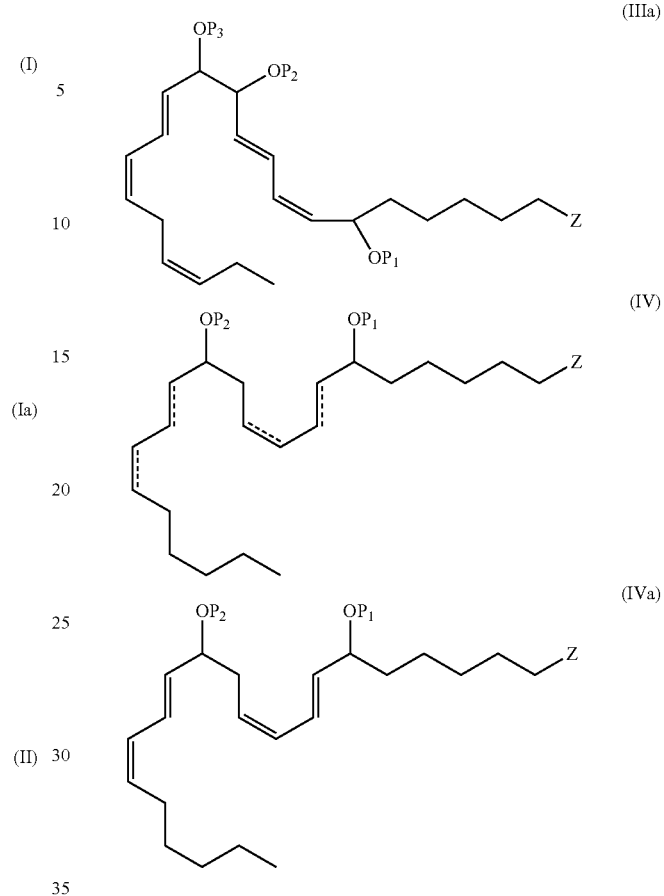

wherein each of $P_1$, $P_2$ and $P_3$, when present, individually is a protecting group or a hydrogen atom;

= = = = =, when present, represents a double bond and each double bond is independently in either the Z or the E configuration;

Wherein the carbon at the 7 and 13 positions or 8, 12 or 20, when present, is independently in the R or S configuration;

Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, C(NR$^a$)NR$^c$R$^c$, —C(NOH)R$^a$, —C(NOH)NR$^c$R$^c$, —OC(O)R$^c$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$; or a pharmaceutically acceptable salt thereof.

2. The compound of paragraph 1, wherein when Z is —C(O)OR$^d$, then R$^d$ for Z is not a hydrogen when P$_1$, P$_2$ and/or P$_3$, when present, are all hydrogen atoms.

3. A purified compound of paragraphs 1 and 2, wherein one or more of P$_1$, P$_2$ and/or P$_3$, are hydrogen atoms, Z is —C(O)OR$^d$ and R$^d$ of Z is a hydrogen atom.

4. The compound of either of paragraphs 1, 2 or 3, wherein the compound is a pharmaceutically acceptable salt of the carboxylic acid.

5. The compound of any of paragraphs 1 through 4, further comprising a carrier to provide a composition.

6. A method of treating or preventing inflammasome activation, diabetes, nasopharyngitis, arthralgia, diarrhea, pain in the extremities, bacterial infection, dyspepsia, nausea, musculoskeletal pain, muscle spasms, myalgia, insomnia, pharyngolaryngia pain, inflammation, tissue degeneration, arterial inflammation, arthritis, psoriasis, urticara, vasculitis, asthma, ocular inflammation, pulmonary inflammation, pulmonary fibrosis, seborrheic dermatitis, pustular dermatosis, cardiovascular diseases, recruitment of neutrophils, leukocytes and/or cytokines, allergy, Alzheimer's disease, asthma, atherosclerosis, cancer, cardiovascular diseases, diabetes, genitourinary disorders, hypertension, infectious diseases, neuromuscular disorders, renal disorders, oral infections or periodontal disease comprising the step of administering an effective amount of one or more of the compounds as claimed in any of claims 1 through 5 to a subject in need thereof, such that the disease or condition is treated or prevented.

7. A method to treat or prevent one or more of inflammasome activation, diabetes, nasopharyngitis, arthralgia, diarrhea, pain in the extremities, bacterial infection, dyspepsia, nausea, musculoskeletal pain, muscle spasms, myalgia, insomnia, pharyngolaryngia pain, inflammation, arterial inflammation, arthritis, psoriasis, urticara, vasculitis, asthma, ocular inflammation, pulmonary inflammation, pulmonary fibrosis, seborrheic dermatitis, pustular dermatosis, cardiovascular diseases, recruitment of neutrophils, leukocytes and/or cytokines, allergy, Alzheimer's disease, asthma, atherosclerosis, cancer, cardiovascular diseases, diabetes, genitourinary disorders, hypertension, infectious diseases, neuromuscular disorders, renal disorders, oral infections or periodontal disease comprising the step of administering an effective amount of one or more of compounds having the formulae:

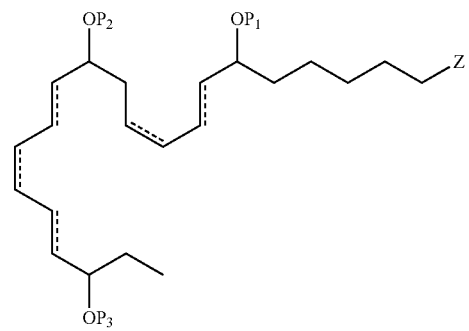
(I)

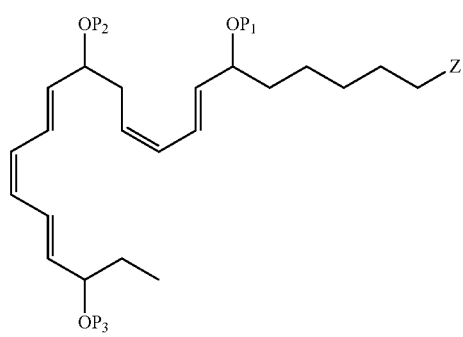
(Ia)

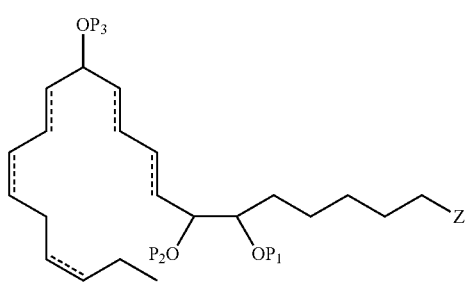
(II)

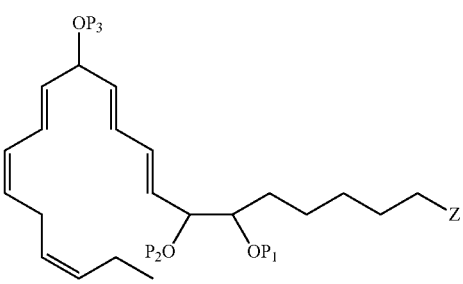
(IIa)

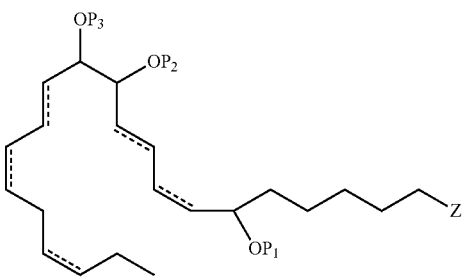
(III)

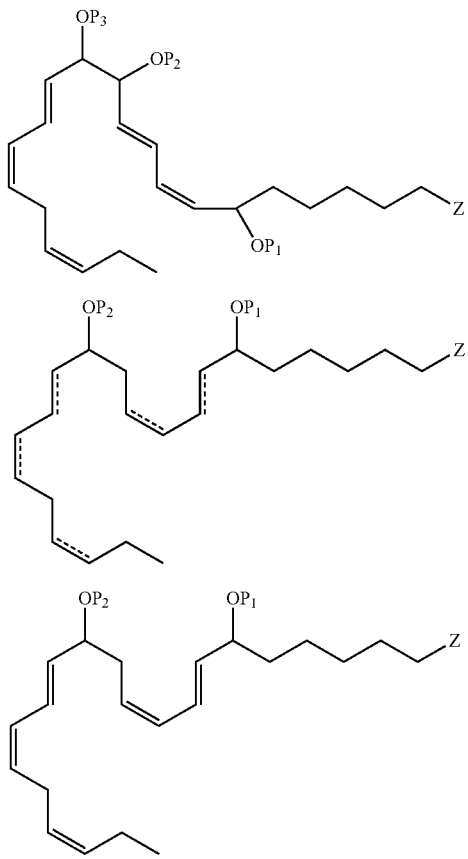

wherein each of $P_1$, $P_2$ and/or $P_3$, when present, individually is a protecting group or a hydrogen atom;

──────, when present, represents a double bond; and wherein each double bond is independently in the Z or the E configuration;

Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroaryl alkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$NR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof, provided when Z is —C(O)OR$^d$, then R$^d$ for Z is not a hydrogen when $P_1$, $P_2$ and $P_3$ are each hydrogen atoms, to a subject in need thereof, such that the disease or condition is treated or prevented.

8. The method of any of claims 1-7, wherein the compound is purified and when $P_1$, $P_2$ and $P_3$ are hydrogen atoms, Z is —C(O)OR$^d$ and R$^d$ of Z is a hydrogen atom.

9. The method of either of paragraphs 1 through 8, wherein the compound is a pharmaceutically acceptable salt of the carboxylic acid.

10. The method of any of paragraphs 1 through 9, further comprising a carrier to provide a composition.

11. A method to treat or prevent a bacterial infections comprising administering to a subject in need thereof a compound according to paragraphs 1-10 and a statin compound.

12. A method to augment statin therapy comprising providing to a subject in need thereof a therapeutically effective amount of a compound according to paragraphs 1-11 in addition to a statin compound to a subject in need of statin therapy.

13. A method to increase the survival rate of a subject suffering from bacterial infections comprising: administering to the subject a therapeutic amount of a compound according to any of paragraphs 1-12.

14. A method to promote phagocytosis, efferocytosis, wound healing and tissue regeneration in a subject in need thereof comprising, administering to a patient in need thereof a therapeutically effective amount of a compound according to any of paragraphs 1-13.

15. A method of stimulating reactive oxygen species production in leukocytes comprising administering to a subject in need of leukocyte stimulation a therapeutic amount of a compound according to any of paragraphs 1-14.

Various exemplary embodiments of devices and compounds as generally described above and methods according to this invention, will be understood more readily by reference to the following examples, which are provided by way of illustration and are not intended to be limiting of the invention in any fashion.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative not limiting. Various changes may be made without departing from the spirit and scope of the invention. therefore, the invention is intended to embrace all known or later-developed alternatives, modifications, variations, improvements and/or substantial equivalents of these exemplary embodiments.

REFERENCES

1. Ward, P. A. New approaches to the study of sepsis. *EMBO molecular medicine* 4, 1234-1243 (2012).
2. Magill, S. S., et al. Multistate point-prevalence survey of health care-associated infections. *The New England journal of medicine* 370, 1198-1208 (2014).

3. Fullerton, J. N., O'Brien, A. J. & Gilroy, D. W. Lipid mediators in immune dysfunction after severe inflammation. *Trends in immunology* 35, 12-21 (2014).

4. Serhan, C. N. Pro-resolving lipid mediators are leads for resolution physiology. *Nature* 510, 92-101 (2014).

5. Tabas, I. & Glass, C. K. Anti-inflammatory therapy in chronic disease: challenges and opportunities. *Science* 339, 166-172 (2013).

6. Lemaitre, R. N., et al. Genetic loci associated with plasma phospholipid n-3 fatty acids: a meta-analysis of genome-wide association studies from the CHARGE Consortium. *PLoS genetics* 7, e1002193 (2011).

7. Dalli, J., Colas, R. A. & Serhan, C. N. Novel n-3 immunoresolvents: structures and actions. *Sci Rep* 3, 1940 (2013).

8. Chiang, N., et al. Infection regulates pro-resolving mediators that lower antibiotic requirements. *Nature* 484, 524-528 (2012).

9. Serhan, C. N., et al. Resolvins: a family of bioactive products of omega-3 fatty acid transformation circuits initiated by aspirin treatment that counter proinflammation signals. *The Journal of experimental medicine* 196, 1025-1037 (2002).

10. Sadik, C. D., Kim, N. D. & Luster, A. D. Neutrophils cascading their way to inflammation. *Trends in immunology* 32, 452-460 (2011).

11. Borregaard, N. Neutrophils, from marrow to microbes. *Immunity* 33, 657-670 (2010).

12. Mead, P. S., et al. Food-related illness and death in the United States. *Emerg Infect Dis* 5, 607-625 (1999).

13. Markworth, J. F., et al. Human inflammatory and resolving lipid mediator responses to resistance exercise and ibuprofen treatment. *American journal of physiology. Regulatory, integrative and comparative physiology* 305, R1281-1296 (2013).

14. Claria, J. & Serhan, C. N. Aspirin triggers previously undescribed bioactive eicosanoids by human endothelial cell-leukocyte interactions. *Proceedings of the National Academy of Sciences of the United States of America* 92, 9475-9479 (1995).

15. Kandasamy, K., et al. Atorvastatin prevents vascular hyporeactivity to norepinephrine in sepsis: role of nitric oxide and alpha(1)-adrenoceptor mRNA expression. *Shock* 36, 76-82. (2011).

16. Atar, S., et al. Atorvastatin-induced cardioprotection is mediated by increasing inducible nitric oxide synthase and consequent S-nitrosylation of cyclooxygenase-2. *American journal of physiology. Heart and circulatory physiology* 290, H1960-1968 (2006).

17. Lins, R. L., et al. Pharmacokinetics of atorvastatin and its metabolites after single and multiple dosing in hypercholesterolaemic haemodialysis patients. *Nephrology, dialysis, transplantation: official publication of the European Dialysis and Transplant Association—European Renal Association* 18, 967-976 (2003).

18. Samuelsson, B. Role of basic science in the development of new medicines: examples from the eicosanoid field. *The Journal of biological chemistry* 287, 10070-10080 (2012).

19. Ji, Y., Akerboom, T. P., Sies, H. & Thomas, J. A. S-nitrosylation and S-glutathiolation of protein sulfhydryls by S-nitroso glutathione. *Archives of biochemistry and biophysics* 362, 67-78 (1999).

20. von Moltke, J., et al. Rapid induction of inflammatory lipid mediators by the inflammasome in vivo. *Nature* 490, 107-111 (2012).

21. Henriksbo, B. D., et al. Fluvastatin causes NLRP3 inflammasome-mediated adipose insulin resistance. *Diabetes* (2014).

22. Cederberg, H., et al. Increased risk of diabetes with statin treatment is associated with impaired insulin sensitivity and insulin secretion: a 6 year follow-up study of the METSIM cohort. *Diabetologia* 58, 1109-1117 (2015).

23. Gryglewski, R. J. & Mackiewicz, Z. Vane's blood-bathed organ technique adapted to examine the endothelial effects of cardiovascular drugs in vivo. *Pharmacological reports: PR* 62, 462-467 (2010).

24. Ye, Y., et al. Activation of peroxisome proliferator-activated receptor-gamma (PPAR-gamma) by atorvastatin is mediated by 15-deoxy-delta-12,14-PGJ2. *Prostaglandins & other lipid mediators* 84, 43-53 (2007).

25. Morikawa, S., et al. The effect of statins on mRNA levels of genes related to inflammation, coagulation, and vascular constriction in HUVEC. Human umbilical vein endothelial cells. *Journal of atherosclerosis and thrombosis* 9, 178-183 (2002).

26. Ye, Y., et al. Phosphorylation of 5-lipoxygenase at ser523 by protein kinase A determines whether pioglitazone and atorvastatin induce proinflammatory leukotriene B4 or anti-inflammatory 15-epi-lipoxin a4 production. *Journal of immunology* 181, 3515-3523 (2008).

27. Chiang, N., et al. Infection regulates pro-resolving mediators that lower antibiotic requirements. *Nature* 484, 524-528 (2012).

28. Serhan, C. N., et al. Resolvins: a family of bioactive products of omega-3 fatty acid transformation circuits initiated by aspirin treatment that counter proinflammation signals. *The Journal of experimental medicine* 196, 1025-1037 (2002).

29. Colas, R. A., Shinohara, M., Dalli, J., Chiang, N. & Serhan, C. N. Identification and signature profiles for pro-resolving and inflammatory lipid mediators in human tissue. *American journal of physiology. Cell physiology* (2014).

30. Oh, S. F., Pillai, P. S., Recchiuti, A., Yang, R. & Serhan, C. N. Pro-resolving actions and stereoselective biosynthesis of 18S E-series resolvins in human leukocytes and murine inflammation. *The Journal of clinical investigation* 121, 569-581 (2011).

31. Corey, E. J. Bakshi, R. K. & Shibata, S. Highly Enantioselective Borane Reduction of Ketones Catalyzed by Chiral Oxazaborolidines. Mechanism and Synthetic Implications. *J Am Chem Soc* 109, 5551-5553 (1987).

32. Gangemi, S., et al. Physical exercise increases urinary excretion of lipoxin A4 and related compounds. *Journal of applied physiology* 94, 2237-2240 (2003).

33. Hemler, M. E. & Lands, W. E. Protection of cyclooxygenase activity during heme-induced destabilization. *Archives of biochemistry and biophysics* 201, 586-593 (1980).

34. Ji, Y., Akerboom, T. P., Sies, & Thomas, J. A. S-nitrosylation and S-glutathiolation of protein sulfhydryls by S-nitroso glutathione. *Archives of biochemistry and biophysics* 362, 67-78 (1999).

35. http://www.rxlist.com/lipitor-drug/side-effects-interactions.htm

What is claimed is:

1. A resolvin compound having the formula:

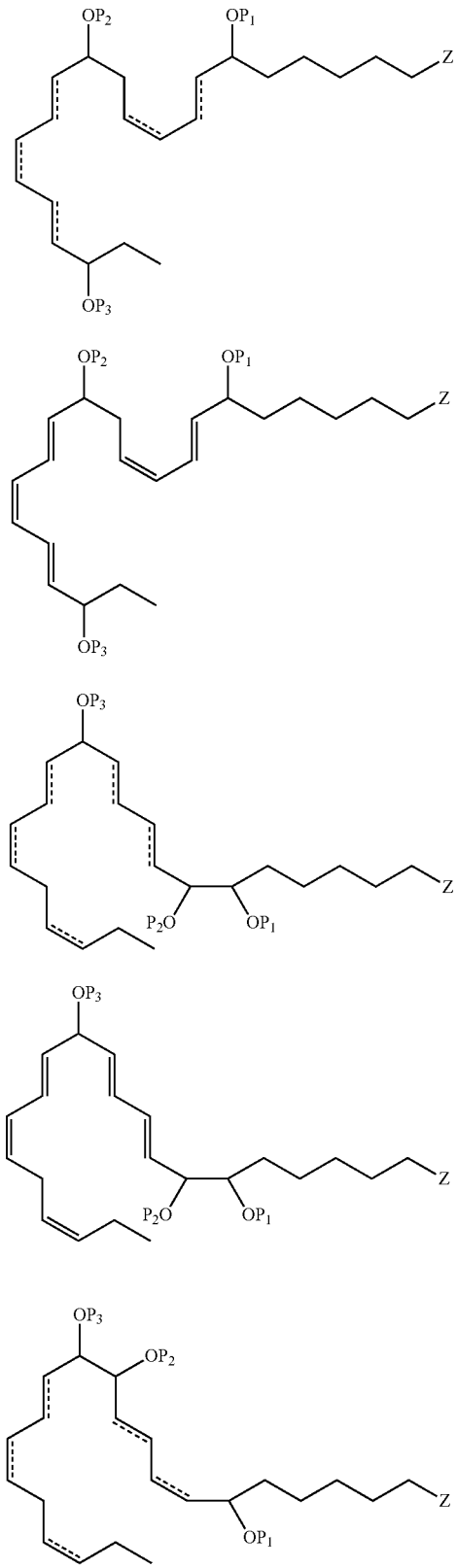

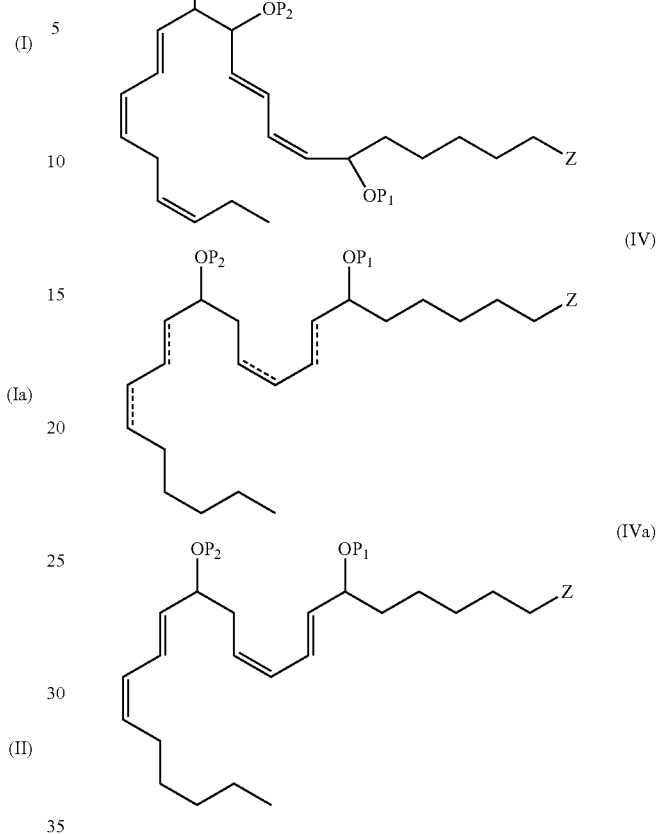

wherein each of $P_1$, $P_2$ and $P_3$, when present, individually is a protecting group or a hydrogen atom;

╌╌╌╌╌, when present, represents a double bond and each double bond is independently in either the Z or the E configuration;

wherein the carbon at the 7 and 13 positions or 8, 12 or 20, when present, is independently in the R or S configuration;

Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)

$R^d$, $-S(O)_2R^d$, $-S(O)_2OR^d$, $-S(O)NR^cR^c$, $-S(O)_2NR^cR^c$, $-OS(O)R^d$, $-OS(O)_2R^d$, $-OS(O)_2OR^d$, $-OS(O)_2NR^cR^c$, $-C(O)R^d$, $-C(O)OR^d$, $-C(O)NR^cR^c$, $-C(NH)NR^cR^c$, $-C(NR^a)NR^cR^c$, $-C(NOH)R^a$, $-C(NOH)NR^cR^c$, $-OC(O)R^d$, $-OC(O)OR^d$, $-OC(O)NR^cR^c$, $-OC(NH)NR^cR^c$, $-OC(NR^a)N R^cR^c$, $-[NHC(O)]_nR^d$, $-[NR^aC(O)]_nR^d$, $-[NHC(O)]_nOR^d$, $-[NR^aC(O)]_nOR^d$, $-[NHC(O)]_n NR^cR^c$, $-[NR^aC(O)]_nNR^cR^c$, $-[NHC(NH)]_nNR^cR^c$ or $-[NR^aC(NR^a)]_nNR^cR^c$;

each n, independently is an integer from 0 to 3; and each $R^d$, independently is a protecting group or $R^a$;

provided when Z is $-C(O)OR^d$, then $R^d$ for Z is not a hydrogen or a pharmaceutically acceptable salt thereof when $P_1$, $P_2$ and/or $P_3$, when present, are all hydrogen atoms.

2. The resolvin compound of claim 1, wherein the compound is a pharmaceutically acceptable salt of the carboxylic acid.

3. A composition comprising the resolvin compound of claim 2 and a carrier.

* * * * *